(12) United States Patent
Pairet et al.

(10) Patent No.: US 7,776,315 B2
(45) Date of Patent: *Aug. 17, 2010

(54) PHARMACEUTICAL COMPOSITIONS BASED ON ANTICHOLINERGICS AND ADDITIONAL ACTIVE INGREDIENTS

(75) Inventors: Michel Pairet, Biberach (DE); Michael P. Pieper, Biberach (DE); Christopher John Montague Meade, Maselheim (DE); Richard Reichl, Gau-Algesheim (DE); Christel Schmelzer, Ingelheim (DE); Birgit Jung, Laupheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 1501 days.

This patent is subject to a terminal disclaimer.

(21) Appl. No.: 11/006,940

(22) Filed: Dec. 8, 2004

(65) Prior Publication Data

US 2005/0148562 A1  Jul. 7, 2005

Related U.S. Application Data

(63) Continuation-in-part of application No. 10/776,757, filed on Feb. 11, 2004, which is a continuation of application No. 10/086,145, filed on Oct. 19, 2001, now abandoned, application No. 11/006,940, which is a continuation-in-part of application No. 10/775,901, filed on Feb. 10, 2004, now abandoned, which is a continuation of application No. 10/027,662, filed on Dec. 20, 2001, now abandoned, application No. 11/006,940, which is a continuation-in-part of application No. 10/613,783, filed on Jul. 3, 2003, now abandoned, which is a continuation of application No. 10/093,240, filed on Mar. 7, 2002, now abandoned, application No. 11/006,940, which is a continuation-in-part of application No. 10/763,894, filed on Jan. 23, 2004, now abandoned, which is a continuation of application No. 10/419,358, filed on Apr. 21, 2003, now Pat. No. 6,696,042, which is a continuation of application No. 10/092,116, filed on Mar. 6, 2002, now Pat. No. 6,620,438, application No. 11/006,940, which is a continuation-in-part of application No. 10/413,065, filed on Apr. 14, 2003, now abandoned, which is a continuation of application No. 10/100,659, filed on Mar. 18, 2002, now Pat. No. 6,608,054, application No. 11/006,940, which is a continuation-in-part of application No. 10/824,391, filed on Apr. 14, 2004, now abandoned, which is a continuation of application No. 10/007,182, filed on Oct. 19, 2001, now abandoned, application No. 11/006,940, which is a continuation-in-part of application No. 10/465,921, filed as application No. PCT/EP01/14579 on Dec. 12, 2001, application No. 11/006,940, which is a continuation-in-part of application No. 10/360,064, filed on Feb. 7, 2003, now abandoned.

(60) Provisional application No. 60/257,220, filed on Dec. 21, 2000, provisional application No. 60/253,613, filed on Nov. 28, 2000, provisional application No. 60/257,221, filed on Dec. 21, 2000, provisional application No. 60/281,857, filed on Apr. 5, 2001, provisional application No. 60/281,653, filed on Apr. 5, 2001, provisional application No. 60/281,874, filed on Apr. 5, 2001, provisional application No. 60/314,599, filed on Aug. 24, 2001, provisional application No. 60/369,213, filed on Apr. 1, 2002.

(51) Int. Cl.
A61K 9/14 (2006.01)
A61K 9/12 (2006.01)
A61K 9/00 (2006.01)
A61K 31/415 (2006.01)
A61K 31/44 (2006.01)

(52) U.S. Cl. .......................... 424/46; 424/45; 424/400; 424/489; 514/393; 514/291

(58) Field of Classification Search ................. 424/400, 424/489, 45, 46; 514/393, 291
See application file for complete search history.

(56) References Cited

U.S. PATENT DOCUMENTS

| | | | |
|---|---|---|---|
| 4,042,700 A | | 8/1977 | Banholzer et al. |
| 4,232,002 A | | 11/1980 | Nogrady |
| 4,313,931 A | * | 2/1982 | Walther et al. ............... 424/45 |
| 4,608,377 A | | 8/1986 | Banholzer et al. |
| 4,783,534 A | | 11/1988 | Banholzer et al. |
| 5,610,163 A | * | 3/1997 | Banholzer et al. .......... 514/291 |
| 5,654,314 A | | 8/1997 | Banholzer et al. |
| 5,655,523 A | | 8/1997 | Hodson et al. |
| 5,770,738 A | | 6/1998 | Banholzer et al. |
| 5,824,669 A | | 10/1998 | Garvey et al. |
| 5,934,272 A | | 8/1999 | Lloyd et al. |
| 5,952,505 A | | 9/1999 | Banholzer et al. |
| 5,962,464 A | * | 10/1999 | Handley et al. ............. 514/290 |
| 6,045,778 A | | 4/2000 | Jager et al. |
| 6,107,281 A | * | 8/2000 | Jones et al. ................... 514/17 |
| 6,114,333 A | | 9/2000 | Davis et al. |
| 6,136,824 A | | 10/2000 | MacLeod et al. |
| 6,197,824 B1 | | 3/2001 | Schromm et al. |
| 6,284,287 B1 | | 9/2001 | Sarlikiotis et al. |
| 6,299,861 B1 | * | 10/2001 | Banholzer et al. ............. 424/45 |
| 6,403,580 B1 | | 6/2002 | Himmelsbach et al. |
| 6,433,027 B1 | | 8/2002 | Bozung et al. |
| 6,455,524 B1 | | 9/2002 | Bozung et al. |
| 6,475,467 B1 | | 11/2002 | Keller et al. |
| 6,482,429 B1 | | 11/2002 | Etzler |
| 6,486,321 B2 | | 11/2002 | Banholzer et al. |
| 6,506,900 B1 | | 1/2003 | Banholzer et al. |
| 6,552,029 B1 | | 4/2003 | Davis et al. |
| 6,608,054 B2 | | 8/2003 | Meade et al. |
| 6,653,305 B2 | | 11/2003 | Himmelsbach et al. |
| 6,656,946 B2 | | 12/2003 | Himmelsbach et al. |
| 6,740,651 B2 | | 5/2004 | Himmelsbach et al. |
| 2001/0041702 A1 | | 11/2001 | Crocker et al. |
| 2002/0052312 A1 | | 5/2002 | Reiss et al. |
| 2002/0082270 A1 | | 6/2002 | Himmelsbach et al. |
| 2002/0115680 A1 | | 8/2002 | Meissner et al. |
| 2002/0115681 A1 | | 8/2002 | Bozung et al. |
| 2002/0137764 A1 | | 9/2002 | Drechsel et al. |
| 2002/0169180 A1 | | 11/2002 | Himmelsbach et al. |
| 2002/0173509 A1 | | 11/2002 | Himmelsbach et al. |
| 2002/0183292 A1 | | 12/2002 | Pairet et al. |
| 2002/0193392 A1 | | 12/2002 | Schmelzer et al. |
| 2003/0018019 A1 | | 1/2003 | Meade et al. |
| 2003/0119859 A1 | | 6/2003 | Gavin |

FOREIGN PATENT DOCUMENTS

| | | |
|---|---|---|
| DE | 42 03 306 A | 8/1993 |
| DE | 198 35 346 A1 | 5/1998 |
| EP | 05040112 A2 | 5/1992 |
| EP | 1 040 829 A2 | 10/2000 |
| WO | WO 95 20045 A1 | 7/1995 |
| WO | WO 96 13292 | 5/1996 |
| WO | WO 96 30347 A1 | 10/1996 |
| WO | WO 96 32386 A1 | 10/1996 |
| WO | WO 96 33980 A1 | 10/1996 |
| WO | WO 97 02266 A1 | 1/1997 |
| WO | WO 9705136 A1 * | 2/1997 |
| WO | WO 97 32865 A1 | 9/1997 |
| WO | WO 97 46243 A | 12/1997 |
| WO | WO 98 41256 A | 9/1998 |
| WO | WO 99 35146 A1 | 7/1999 |
| WO | WO 00 31048 A1 | 6/2000 |
| WO | WO 00 35428 | 6/2000 |
| WO | WO 01 46151 A1 | 6/2001 |
| WO | WO 01 57025 A1 | 8/2001 |
| WO | WO 01 61816 A1 | 8/2001 |
| WO | WO 01/78736 A1 | 10/2001 |
| WO | WO 01/78739 A1 | 10/2001 |
| WO | WO 01/78741 A1 | 10/2001 |
| WO | WO 01/78743 A1 | 10/2001 |
| WO | WO 02 09689 A1 | 2/2002 |
| WO | WO 03/011274 | 2/2003 |

OTHER PUBLICATIONS

West et al, "Solid Solutions, Solid State Chemistry and its Applications," John Wiley & Sons, 1986, pp. 358 and 365.*

Vippagunta et al. Advanced Drug Defivery Reviews, 2001, vol. 48, pp. 3-26.*

Ulrich, Kirk-Othmer Encyclopedia of Chemical Technology, John Wiley & Sons, 2002, Chapter 4 in Crystallization.*

Maesen, et al: "Tiotropium bromide, a new long-acting antimuscarinic bronchodilator: a pharmacodynamic study in patients with chronic obstructive pulmonary disease" 1995, p. 1508-1513, vol. 8, European respiratory Journals. Department of Respiratory diseases, De Wever Hospital , the Hague,and the department of Clinical Research , Boehringer Ingelheim, Alkmaar, The Netherlands.

Torphy, T.J., et al; Ariflo(SB207499), a Second Generation Phosphodiesterase 4 Inhibitor for the Treatment of Asthma and COPD: from Concept to Clinic; Pulmonary Pharmacology and Therapeutics (1999) 12, pp. 131-135.

Disse, Bernd, et al; Tiotropoum (SPIRIVA): Mechanistical Considerations and Clinical Profile in Obstructive Lung Disease; Life Sciences, vol. 64, Nos. 6/7 pp. 457-464, 1999.

Prescott, L.F.; Clinically Important Drug Interactions, Chapter VIII, Avery's Drug Treatment pp. 256-282, 1997.

Chemical Abstract: CA 119:167766; DE 42 03 306 A1, 1993.

Balzano, G. et al, "Effectiveness and Acceptabililty of a Domicilialry Multidrug Inhalation Treatment in Elderly Patients with Chronic Airflow Obstruction: Metered Dose Inhaler Versus Jet Nebulilzer", Journal of Aerosol Medicine, vol. 13, No. 1, 2000, pp. 25-33.

Rutgers, S. R., et al; "Short-term Treatment with Budesonide Does Not Improve Hyperresponsiveness to Adenosine 5-Monophosphate in COPD", American Journal of Respiratory and Critical Care Medicine, vol. 157, pp. 880-887, 1998.

van Schayck, C. P. et al; "Periodic Treatment Regimens with Inhaled Steroids in Asthma or Chronic Obstructive Pulmonary Disease", Journal of American Medical Association, Jul. 12, 1995, vol. 274, No. 2, pp. 161-164.

Barnes, P.J., "Nonantimicrobial Aspects of Therapy", Seminars in Respiratory Infections, Grune and Stratton, Orlando, US, Bd. 15, Nr. 1, 2000, Seiten 52-58 XP000911165, ISSN: 0882-0546, Seite 53, Spalte 1, Absatz 2—Seite 56, Spalte 1, Zeile 20-40.

Nishimura, et al; "Additive effect of oxitropium bromide in combination with inhaled corticosteroids in the treatment of elderly patients with chronic asthma"; Allergology International, Mar. 1999, pp. 85-88.

Chemical Abstract: CA 117:258239; EP 0 504 112 A2, 1992.

Gennaro, et al; Ed., Remington's Pharmaceutical Sciences, 18th Ed., 1990, pp. 1694-1699, 1706-1707, 1709.

Disse, B. et al: "BA 679 BR, A Novel Long-Acting Anticholinergic Bronchodilator", Life Sciences, Pergamon Press, Oxford, GB, Bd. 5/6, Nr. 52, 1993, Seiten 537-544, XP008002589 ISSN: 0024-3205.

Patent Abstracts of Japan; vol. 1999, No. 02, Feb. 26, 1999 & JP 10 298107 A, Taisho Pharm. Co., Nov. 10, 1998.

Tavakkoli, A., Rees, P.J.: "Drug Treatment of Asthma in the 1990s: Achievements and New Strategies", Drugs, Bd. 57, Nr. 1, 1999, Seiten 1-8 XP001098314 ISSN: 0012-6667 Seite 3, Spalte 2, Abstaz 2; Seite 4, Spalte 2, Abstaz 2.

Data Base WPI Derwent Publications Ltd., London, GB; AN 2001-626119 XP002212897 Matsumoto, Tatsumi, Tarui, Naoki et al.: "New and Know Furoisoquinoline Compounds as Phosphodiesterase IV Inhibitors".

Budavari, et al, The Merck Index, 12th Edition (1996), p. 1614, Abstract No. 9598.

Takahashi, et al, "Contraction of hyman airway smooth muscle by endothelin-1 and IRL 1620: effect of bosentan", E. J. of Pharmacology (1997), 324 (2,3), pp. 219-222 (See Abstract).

Hay, D. W. P.; "Chronic obstructive pulmonary disease: emerging therapies", Current Opinion in Chemical biology, Bd. 4, Nr. 4, 2000, pp. 412-419.

Naclerio, R. M.; "Optimizing Treatment Options"; Clinical and Experimental Allergy, Bd. 28, Nr. Suppl. 6, 1998, 54-59.

Simons, et al; "Optimum Pharmacological management of Chronic Rhinitis";, Drugs, Bd. 38, Nr. 2, 1989, 313-331.

Mon, et al; "Aerosol Therapy in Asthma"; Revue Des Maladies Respiratoires, Bd. 6, Nr. 3, 1989, 189-200.

Pavia, et al; "Preliminary Data From Phase II Studies With Respimat, A Propellant-Free Soft Mist Inhaler"; J. of Aerosol Medicine: the Official J. of the Int'l Soc. for Aerosols in Medicine. US 1999, Bd. 12 Suppl. 1 1999 S33-S39.

Chemical Abstract: CA 132:141964; DE 198 35 346 A1.

Naeije, R. et al; "Pulmonary Hypertension Associated With COPD"; Critical Care; 2001; 5 (6), pp. 286-289.

Channick, R. N. et al; "Endothelin Receptor Antagonism: A New Era In The Treatment Of Pulmonary Arterial Hypertension"; Advances in Pulmonary Hypertension; 2002.

* cited by examiner

*Primary Examiner*—Shengjun Wang
(74) *Attorney, Agent, or Firm*—Michael P. Morris; Mary-Ellen M. Devlin; Wendy A. Petka

(57) ABSTRACT

A pharmaceutical composition comprising an anticholinergic and at least one additional active ingredient selected from among corticosteroids, dopamine agonistes, PDE-IV inhibitors, NK1-antagonists, endothelin antagonists, antihistamines, and EGFR-kinase inhibitors, processes for preparing them and their use in the treatment of respiratory diseases.

28 Claims, 3 Drawing Sheets

PHARMACEUTICAL COMPOSITIONS BASED ON ANTICHOLINERGICS AND ADDITIONAL ACTIVE INGREDIENTS

RELATED APPLICATIONS

This application is a continuation-in-part of the following applications:

U.S. Ser. No. 10/776,757, filed Feb. 11, 2004, which application is a continuation of U.S. Ser. No. 10/086,145, filed Oct. 19, 2001, which claims benefit of U.S. Provisional Application Ser. No. 60/257,220, filed Dec. 21, 2000, and U.S. Provisional Application Ser. No. 60/253,613, filed Nov. 28, 2000, U.S. Ser. No. 10/775,901, filed Feb. 10, 2004, which application is a continuation of U.S. Ser. No. 10/027,662, filed Dec. 20, 2001, which claims benefit of U.S. Provisional Application Ser. No. 60/257,221, filed Dec. 21, 2000, U.S. Ser. No. 10/613,783, filed Jul. 3, 2003, which application is a continuation of U.S. Ser. No. 10/093,240, filed Mar. 7, 2002, which claims benefit of U.S. Provisional Application Ser. No. 60/281,857, filed Apr. 5, 2001, U.S. Ser. No. 10/763,894, filed Jan. 23, 2004, which application is a continuation of U.S. Ser. No. 10/419,358, filed Apr. 21, 2003 (now U.S. Pat. No. 6,696,042), which application is a continuation of U.S. Ser. No. 10/092,116, filed Mar. 6, 2002 (now U.S. Pat. No. 6,620,438), which claims benefit of U.S. Provisional Application Ser. No. 60/281,653, filed Apr. 5, 2001, U.S. Ser. No. 10,413,065, filed Apr. 14, 2003, which is a continuation of U.S. Ser. No. 10/100,659, filed Mar. 18, 2002, (now U.S. Pat. No. 6,608,054), which claims benefit of U.S. Provisional Application Ser. No. 60/281,874, filed Apr. 5, 2001, U.S. Ser. No. 10/824,391, filed Apr. 14, 2004, which application is a continuation of U.S. Ser. No. 10/007,182, filed Oct. 19, 2001, which claims benefit of U.S. Provisional Application Ser. No. 60/314,599, filed Aug. 24, 2001, and U.S. Provisional Application Ser. No. 60/253,613, filed Nov. 28, 2000, U.S. Ser. No. 10/465,921, filed Aug. 26, 2004, which claims benefit under 35 U.S.C. §365(c), of International Application No. PCT/EP01/14579, filed Dec. 12, 2001, U.S. Ser. No. 10/360,064, filed Feb. 7, 2003, which claims benefit of U.S. Provisional Application Ser. No. 60/369,213, filed Apr. 1, 2002, all of which are hereby claimed, and which applications are incorporated herein in their entirety.

SUMMARY OF THE INVENTION

The present invention relates to novel pharmaceutical compositions based on anticholinergics 1 and at least one additional active ingredient 2 seleceted from among corticosteroids (2a), dopamine agonistes (2b), PDE-IV inhibitors (2c), NK1-antagonists (2d), endothelin antagonists (2e), antihistamines (2f) and EGFR-kinase inhibitors (2g), processes for preparing them and their use in the treatment of respiratory diseases.

In a preferred embodiment the present invention relates to novel pharmaceutical compositions based on anticholinergics 1 and corticosteroids 2a, processes for preparing them and their use in the treatment of respiratory diseases.

In another preferred embodiment the present invention relates to novel pharmaceutical compositions based on anticholinergics 1 and dopamine agonists 2b, processes for preparing them and their use in the treatment of respiratory diseases.

In a yet another preferred embodiment the present invention relates to novel pharmaceutical compositions based on anticholinergics 1 and PDE-IV inhibitors 2c, processes for preparing them and their use in the treatment of respiratory diseases.

In a yet another preferred embodiment the present invention relates to novel pharmaceutical compositions based on anticholinergics 1 and NK1-antagonists 2d processes for preparing them and their use in the treatment of respiratory diseases.

In a yet another preferred embodiment the present invention relates to novel pharmaceutical compositions based on anticholinergics 1 and endothelin antagonists 2e, processes for preparing them and their use in the treatment of respiratory diseases. In a yet another preferred embodiment the present invention relates to novel pharmaceutical compositions based on anticholinergics 1 and antihistamines 2f, processes for preparing them and their use in the treatment of respiratory diseases.

In a yet another preferred embodiment the present invention relates to novel pharmaceutical compositions based on anticholinergics 1 and EGFR-kinase inhibitors 2g, processes for preparing them and their use in the treatment of respiratory diseases.

Surprisingly, it has been found that an unexpectedly beneficial therapeutic effect, partially a synergistic effect can be observed in the treatment of inflammatory or obstructive diseases of the respiratory tract if one or more anticholinergics are used with one or more corticosteroids, one or more dopamine agonists, one or more PDE-IV inhibitors, one or more NK1-antagonists, one or more endothelin antagonists, one or more antihistamines or one or more EGFR-kinase inhibitors. In view of this synergistic effect the pharmaceutical combinations according to the invention can be used in smaller doses than would be the case with the individual compounds used in monotherapy in the usual way. This reduces unwanted side effects such as may occur when corticosteroids, dopamine agonists, PDE-IV inhibitors, NK1-antagonists, endothelin antagonists, antihistamines or EGFR-kinase inhibitors are administered, for example.

The effects mentioned above are observed both when the two active substances are administered simultaneously in a single active substance formulation and when they are administered successively in separate formulations. According to the invention, it is preferable to administer the two active substance ingredients simultaneously in a single formulation.

DESCRIPTION OF THE DRAWINGS

FIGS. 2a and 2b herein are identical to FIGS. 6a and 6b of WO 97/12687.

DETAILED DESCRIPTION OF THE INVENTION

Figure 1:
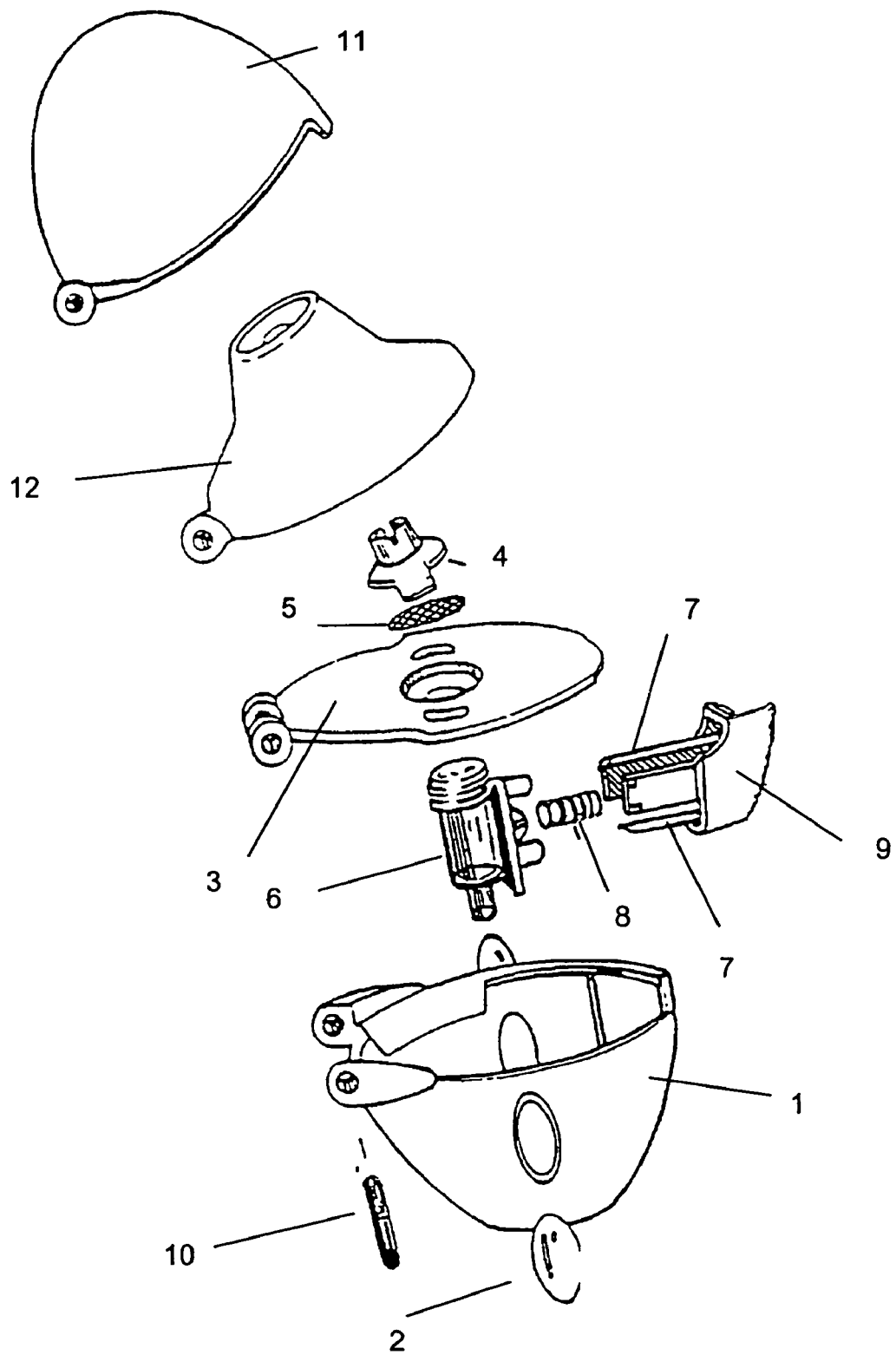
FIG. 1 shows an exploded view of the Handihaler® inhaler for administering the pharmaceutical combination according to the invention in inhalettes.

Within the scope of the present invention the term anticholinergics 1 denotes salts which are preferably selected from among tiotropium salts, oxitropium salts, and ipratropium salts, most preferably tiotropium salts. In the above-mentioned salts the cations tiotropium, oxitropium, and ipratropium are the pharmacologically active ingredients. Within the scope of the present patent application, an explicit reference to the above cations is indicated by the use of the number 1'. Any reference to compounds 1 naturally also includes a reference to the ingredients 1' (tiotropium, oxitropium, or ipratropium).

By the salts 1 which may be used within the scope of the present invention are meant the compounds which contain, in addition to tiotropium, oxitropium, or ipratropium as counterion (anion), chloride, bromide, iodide, sulfate, methanesulfonate, or p-toluenesulfonate. Within the scope of the present invention, the methanesulfonate, chloride, bromide, and iodide are preferred of all the salts 1, the methanesulfonate and bromide being of particular importance. Of outstanding importance according to the invention are salts 1 selected from among tiotropium bromide, oxitropium bromide, and ipratropium bromide. Tiotropium bromide is particularly preferred, preferably in form of the crystalline tiotropium bromide monohydrate.

Within the scope of the present invention, the word corticosteroids (hereinafter 2a) denotes compounds selected from among flunisolide, beclomethasone, triamcinolone, budesonide, fluticasone, mometasone, ciclesonide, rofleponide, GW 215864, KSR 592, ST-126, and dexamethasone. Preferably, compounds 2a is selected from among flunisolide, beclomethasone, triamcinolone, budesonide, fluticasone, mometasone, ciclesonide, and dexamethasone. Most preferably, compound 2a is selected from among budesonide, fluticasone, mometasone, and ciclesonide. In some cases, within the scope of the present patent application, the term steroids 2a may also be used on its own instead of the word corticosteroids 2a.

Any reference to steroids 2a within the scope of the present invention includes a reference to salts or derivatives 2a' which may be formed from the steroids. Examples of possible salts or derivatives 2a' include: sodium salts, sulfobenzoates, phosphates, isonicotinates, acetates, propionates, dihydrogen phosphates, palmitates, pivalates, or furoates. In some cases the compounds of formula 2a may also occur in the form of their hydrates.

Within the scope of the present invention, the word dopamine agonists (hereinafter 2b) denotes compounds selected from among bromocriptin, cabergolin, alpha-dihydroergocryptin, lisuride, pergolide, pramipexol, roxindol, ropinirol, talipexol, terguride and the 7-(2-aminoethyl)-benzothiazolones of general formula 2ba

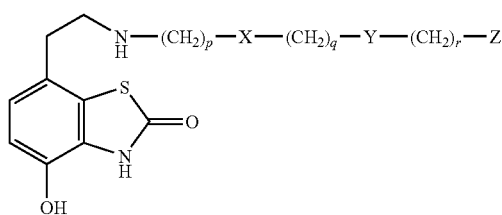

wherein
X and Y which may be identical or different denote —S(O)$_n$— or —O—;
n denotes 0, 1 or 2;
p, q and r which may be identical or different denote 2 or 3;

Z denotes phenyl, which may optionally be substituted by a group selected from among halogen, —OR$^1$, NO$_2$ or NR$^2$, R$^3$, or a 5- or 6-membered heterocycle containing N, O or S;

R$^1$, R$^2$ and R$^3$ which may be identical or different denote hydrogen or C$_1$-C$_6$-alkyl.

The abovementioned compounds of formula 3 are disclosed in WO 93/24473, to which reference is hereby made in its entirety.

Preferably, within the scope of the present invention, the dopamine agonists 2b are selected from among bromocriptin, cabergolin, alpha-dihydroergocryptin, lisuride, pergolide, pramipexol, roxindol, ropinirol, talipexol, terguride and the compound of formula 2ba'.

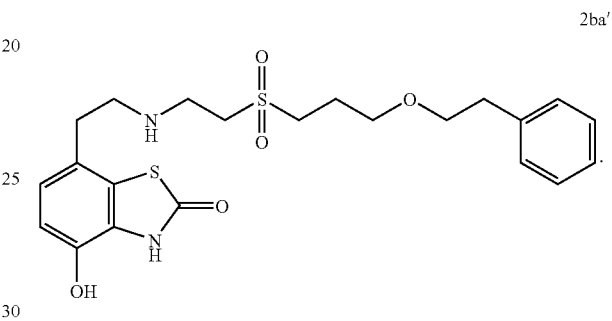

The abovementioned compound of formula 2ba' is also disclosed in WO 93/24473 and is hereinafter also referred to as viozan.

Preferably, the dopamine agonist 2b is selected from among pramipexol, talipexol and viozan, of which pramipexol and viozan, especially viozan, are of particular importance.

Other preferred dopamine agonists 2b in the pharmaceutical combinations according to the invention are those which do not overcome the blood-brain barrier and are primarily characterised by a peripheral activity. Particularly preferred are peripherally active dopamine agonists 2b selected from among dopamine, fenoldopam, dopexamine, CHF 1035, tolnaperisine and RU-40021, of which dopamine, fenoldopam, dopexamine and CHF 1035, especially dopamine, fenoldopam and dopexamine are of exceptional importance.

Any reference to the abovementioned dopamine agonists 2b within the scope of the present invention includes a reference to any pharmacologically acceptable acid addition salts thereof which may exist.

By the physiologically acceptable acid addition salts which may be formed from 2b are meant, for example, pharmaceutically acceptable salts selected from the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid.

Within the scope of the present invention, the word PDE-IV inhibitors (hereinafter 2c) denotes compounds selected from among enprofylline, roflumilast, ariflo, Bay-198004, CP-325,366, BY343, D-4396 (Sch-351591), V-11294A, AWD-12-281 and the tricyclic nitrogen heterocycles of general formula 2ca

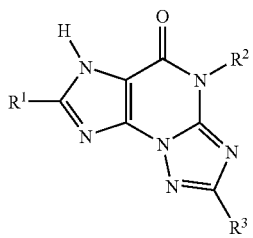

2ca wherein
R¹ denotes $C_1$-$C_5$-alkyl, $C_5$-$C_6$-cycloalkyl, phenyl, benzyl or a 5- or 6-membered, saturated or unsaturated heterocyclic ring which may contain one or two heteroatoms selected from among oxygen and nitrogen;
R² denotes $C_1$-$C_5$-alkyl or $C_2$-$C_4$-alkenyl;
R³ denotes $C_1$-$C_5$-alkyl which may optionally be substituted by $C_1$-$C_4$-alkoxy, $C_5$-$C_6$-cycloalkyl, phenoxy or a 5- or 6-membered, saturated or unsaturated heterocyclic ring which may contain one or two heteroatoms selected from among oxygen and nitrogen;
$C_5$-$C_6$-cycloalkyl or phenyl or benzyl optionally substituted by $C_1$-$C_4$-alkoxy, optionally in the form of their racemates, their enantiomers, in the form of the diastereomers and the mixtures thereof, optionally in the form of their tautomers and optionally the pharmacologically acceptable acid addition salts thereof.

Of the abovementioned compounds of 2ca those which are preferably used within the scope of the present invention are those compounds of formula 2ca wherein
R¹ denotes $C_1$-$C_4$-alkyl, $C_5$-$C_6$-cycloalkyl, tetrahydrofuranyl, tetrahydropyranyl, piperazinyl, morpholinyl or phenyl;
R² denotes $C_1$-$C_4$-alkyl or $C_2$-$C_4$-alkenyl;
R³ denotes $C_1$-$C_4$-alkyl which may optionally be substituted by $C_1$-$C_4$-alkoxy, $C_5$-$C_6$-cycloalkyl, phenoxy, ($C_1$-$C_4$-alkoxy)phenyloxy, piperazine or pyrrole, $C_5$-$C_6$-cycloalkyl or phenyl or benzyl optionally substituted by $C_1$-$C_4$-alkoxy,
optionally in the form of their racemates, their enantiomers, in the form of the diastereomers and the mixtures thereof, optionally in the form of their tautomers and optionally the pharmacologically acceptable acid addition salts thereof.

Of the compounds of formula 2ca those which are most preferably used within the scope of the present invention are those compounds of formula 2ca wherein
R¹ denotes ethyl, propyl, butyl, cyclopentyl, tetrahydrofuranyl, tetrahydropyranyl, N-morpholinyl or phenyl;
R² denotes ethyl, propyl, allyl or butenyl;
R³ denotes ethyl, propyl, butyl, cyclopentyl, cyclohexylmethyl, benzyl, phenylethyl, phenoxymethyl, methoxybenzyl or N-pyrolylmethyl, optionally in the form of their racemates, their enantiomers, in the form of the diastereomers and the mixtures thereof, optionally in the form of their tautomers and optionally the pharmacologically acceptable acid addition salts thereof.

Most preferably, the compounds used as component 2c are the compounds of formula 2ca wherein
R¹ denotes ethyl, n-propyl, tert-butyl, cyclopentyl, 3-tetrahydrofuryl, N-morpholinyl or phenyl;
R² denotes ethyl or n-propyl;
R³ denotes ethyl, i-propyl, n-propyl, n-butyl, t-butyl, cyclopentyl, cyclohexylmethyl, benzyl, phenylethyl, phenoxymethyl, 4-methoxybenzyl or N-pyrollylmethyl, optionally in the form of their racemates, their enantiomers, in the form of the diastereomers and the mixtures thereof, optionally in the form of their tautomers and optionally the pharmacologically acceptable acid addition salts thereof.

Examples of alkyl groups (including those which are part of other groups) are branched and unbranched alkyl groups with 1 to 5 carbon atoms, such as, for example: methyl, ethyl, n-propyl, isopropyl, n-butyl, isobutyl, sec. butyl, tert.butyl, n-pentyl, isopentyl or neopentyl. The abbreviations Me, Et, n-Pr, i-Pr, n-Bu, i-Bu, t-Bu, etc. may optionally be used for the abovementioned groups.

Examples of cycloalkyl groups with 5 or 6 carbon atoms include cyclopentyl or cyclohexyl. Examples of 5- or 6-membered, saturated or unsaturated heterocyclic rings which may contain one or two heteroatoms selected from among oxygen and nitrogen include: furan, tetrahydrofuran, tetrahydrofuranon, γ-butyrolactone, α-pyran, γ-pyran, dioxolan, tetrahydropyran, dioxan, pyrrole, pyrroline, pyrrolidine, pyrazole, pyrazoline, imidazole, imidazoline, imidazolidine, pyridine, piperidine, pyridazine, pyrimidine, pyrazine, piperazine, morpholine, oxazole, isoxazole, oxazine and pyrazolidine.

Table 1 lists the compounds of general formula 2ca which are most preferably used in conjunction with the compounds 1 within the scope of the invention.

TABLE 1

2ca

| No. | R¹ | R² | R³ |
|---|---|---|---|
| 1 | cyclopentyl | n-propyl | i-propyl |
| 2 | cyclopentyl | n-propyl | ethyl |
| 3 | t-butyl | ethyl | 4-methoxybenzyl |
| 4 | cyclopentyl | ethyl | —CH₂CH₂phenyl |
| 5 | 3-tetrahydrofuryl | ethyl | benzyl |
| 6 | cyclopentyl | n-propyl | n-propyl |
| 7 | t-butyl | ethyl | benzyl |
| 8 | phenyl | n-propyl | n-propyl |
| 9 | cyclopentyl | ethyl | benzyl |
| 10 | -n-propyl | -n-propyl | benzyl |
| 11 | cyclopentyl | ethyl | N-pyrrolylmethyl |
| 12 | cyclopentyl | -n-propyl | benzyl |
| 13 | cyclopentyl | -n-propyl | -t-butyl |
| 14 | cyclopentyl | n-propyl | n-butyl |
| 15 | cyclopentyl | ethyl | —CH₂-Ophenyl |
| 16 | N-morpholinyl | -n-propyl | benzyl |
| 17 | cyclopentyl | ethyl | cyclohexylmethyl |
| 18 | ethyl | ethyl | cyclohexylmethyl |
| 19 | n-propyl | n-propyl | cyclopentyl |

The compounds of general formula 2ca may be prepared analogously to the method described in the prior art for certain of the above-defined compounds of general formula (I) (Tenor et al., Chem. Ber. Vol. 97 (1964) p. 1373-1382), to which reference is hereby made.

Preferably, also, the compound 2c is selected from among enprofylline, roflumilast, ariflo and AWD-12-281, while AWD-12-281 and the abovementioned compounds of formula 2ca are particularly preferred as compound 2c according to the invention.

Any reference to the abovementioned PDE-IV inhibitors 2c within the scope of the present invention includes a reference to any pharmacologically acceptable acid addition salts thereof which may exist.

By the physiologically acceptable acid addition salts which may be formed from 2c are meant, for example, pharmaceutically acceptable salts selected from the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid. Particularly preferred salts of the compounds 2c according to the invention are those selected from among the acetate, hydrochloride, hydrobromide, sulphate, phosphate and methanesulphonate.

Within the scope of the present invention, the word $NK_1$-receptor antagonists (hereinafter 2d) denotes compounds selected from among N-[2-(3,5-bis-trifluoromethyl-phenyl)-ethyl]-2-{4-cyclopropylmethyl-piperazin-1-yl}-N-methyl-2-phenyl-acetamide (BIIF 1149), CP-122721, FK-888, NKP 608C, NKP 608A, CGP 60829, SR 48968(Saredutant), SR 140333 (Nolpitantium besilate/chloride), LY 303 870 (Lanepitant), MEN-11420 (Nepadutant), SB 223412, MDL-105172A, MDL-103896, MEN-11149, MEN-11467, DNK 333A, SR-144190, YM-49244, YM-44778, ZM-274773, MEN-10930, S-19752, Neuronorm, YM-35375, DA-5018, Aprepitant (MK-869), L-754030, CJ-11974, L-758298, DNK-33A, 6b-I, CJ-11974, TAK-637, GR 205171 and the arylglycinamide derivatives of general formula 2da

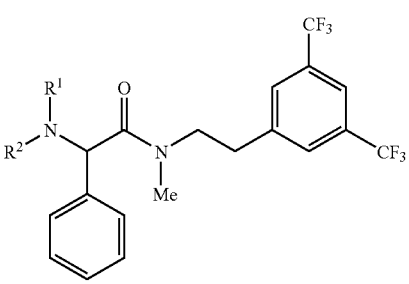

2da wherein
$R^1$ and $R^2$ together with the N to which they are bound form a ring of formula

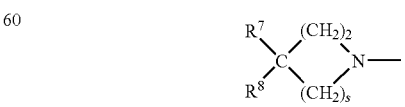

wherein r and s are 2 or 3;
$R^6$ denotes H, $—C_1$-$C_5$-alkyl, $C_3$-$C_5$-alkenyl, propynyl, hydroxy($C_2$-$C_4$)alkyl, methoxy($C_2$-$C_4$)alkyl, di($C_1$-$C_3$) alkylamino($C_2$-$C_4$)alkyl, amino($C_2$-$C_4$)alkyl, amino, di($C_1$-$C_3$)alkylamino, monofluoro to perfluoro($C_1$-$C_2$) alkyl, N-methylpiperidinyl, pyridyl, pyrimidinyl, pyrazinyl or pyridazinyl,
$R^7$ has one of the meanings (a) to (d),
(a) hydroxy
(b) 4-piperidinopiperidyl,
(c)

wherein $R^{16}$ and $R^{17}$ independently of each other denote H, ($C_1$-$C_4$)alkyl, ($C_3$-$C_6$)cycloalkyl, hydroxy($C_2$-$C_4$)alkyl, dihydroxy($C_2$-$C_4$)alkyl, ($C_1$-$C_3$)alkoxy($C_2$-$C_4$)alkyl, phenyl ($C_1$-$C_4$)alkyl or di($C_1$-$C_3$)alkylamino($C_2$-$C_4$)alkyl,
$R^8$ denotes H, optionally in the form of the enantiomers and mixtures of enantiomers thereof, optionally in the form of the racemates thereof.

The abovementioned compounds of formula 2da are known for example from International Patent Applications WO 96/32386 and WO 97/32865, to which reference is hereby made in their entirety.

Preferably, the compound 2d is selected from among BIIF 1149, CP-122721, CGP 60829, MK-869, CJ-11974, GR 205171 and the arylglycinamide derivatives of general formula 2da, wherein
$R^1$ and $R^2$ together with the N to which they are bound form a ring of formula

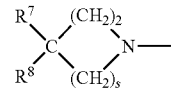

wherein s is 2 or 3;
$R^7$ denotes a group

wherein $R^{16}$ and $R^{17}$ independently of each other denote H, ($C_1$-$C_4$)alkyl, ($C_3$-$C_6$)cycloalkyl, hydroxy($C_2$-$C_4$)alkyl, dihydroxy($C_2$-$C_4$)alkyl, ($C_1$-$C_3$)alkoxy($C_2$-$C_4$)alkyl, phenyl ($C_1$-$C_4$)alkyl or di($C_1$-$C_3$)alkylamino($C_2$-$C_4$)alkyl,
$R^8$ denotes H, optionally in the form of the enantiomers and mixtures of enantiomers thereof and optionally in the form of the racemates thereof.

Particularly preferably, the compound 2d is selected from among BIIF1149 and the arylglycinamide derivatives of general formula 2da, wherein
$R^1$ and $R^2$ together with the N to which they are bound form a ring of formula wherein s is 2 and
$R^7$ denotes a group

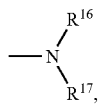

wherein $R^{16}$ and $R^{17}$ independently of each other denote H, $(C_1$-$C_4)$alkyl, $(C_3$-$C_6)$cycloalkyl, hydroxy$(C_2$-$C_4)$alkyl or dihydroxy$(C_2$-$C_4)$alkyl, $R^8$ denotes H, optionally in the form of the enantiomers and mixtures of enantiomers thereof and optionally in the form of the racemates thereof.

Most particularly preferred as compounds of formula 2d are N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide, N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide, N-[2-(3,5-bis-trifluoromethyl-phenyl)-ethyl]-2-[4-(cyclopropylmethyl-methyl-amino)-piperidin-1-yl]-N-methyl-2-phenyl-acetamide, N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide and N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide, optionally in the form of the enantiomers and mixtures of enantiomers thereof and optionally in the form of the racemates thereof.

Of particular importance is N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide, optionally in the form of its enantiomers, preferably in the form of its (S)-enantiomer, optionally in the form of the mixtures of enantiomers thereof, and optionally in the form of the racemates thereof.

Examples of alkyl groups (including those which are part of other groups), unless otherwise defined, are branched and unbranched alkyl groups with 1 to 5 carbon atoms, such as, for example: methyl, ethyl, propyl, 1-methylethyl (isopropyl), n-butyl, 1-methylpropyl, 2-methylpropyl, 1,1-dimethylethyl (tert.butyl), etc. The definitions propyl, butyl and pentyl always include the associated isomeric groups. Hydroxy or dihydroxyalkyl groups are alkyl groups substituted by one or two hydroxy groups.

Examples of alkenyl groups (including those which are part of other groups) are branched and unbranched alkenyl groups with 3 to 5 carbon atoms, provided that they have at least one double bond, such as, for example, propenyl, isopropenyl, butenyl, etc.

Cycloalkyl generally denotes a saturated cyclic hydrocarbon group having 3 to 6 carbon atoms. Examples include cyclopropyl, cyclobutyl, cyclopentyl, cyclohexyl, cyclopropylmethyl, cyclobutylmethyl, cyclopentylmethyl, cyclopropylethyl, cyclobutylethyl, etc.

Alkyloxy, which may optionally also be referred to as alkoxy, denotes a straight-chain or branched alkyl group bound via an oxygen atom. The methoxy group is particularly preferred.

Any reference to the abovementioned $NK_1$-receptor antagonists 2d within the scope of the present invention includes a reference to any pharmacologically acceptable acid addition salts thereof which may exist.

By the physiologically acceptable acid addition salts which may be formed from 2d are meant, for example, pharmaceutically acceptable salts selected from the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid. Particularly preferred salts of the compounds 2d according to the invention are those selected from among the acetate, hydrochloride, hydrobromide, sulphate, phosphate and methanesulphonate.

Within the scope of the present invention the term endothelin antagonists (hereinafter 2e) denotes compounds selected from among tezosentan, bosentan, enrasentan, sixtasentan, T-0201, BMS-193884, K-8794, PD-156123, PD-156707, PD-160874, PD-180988, S-0139 and ZD-1611. Preferred endothelin antagonists 2 within the scope of the present invention are those selected from among tezosentan, bosentan, enrasentan, sixtasentan, T-0201 and BMS-193884, the compounds tezosentan and bosentan being particularly preferred according to the invention.

Any reference to the abovementioned endothelin antagonists 2e within the scope of the present invention includes a reference to any pharmacologically acceptable acid addition salts thereof which may exist. By the physiologically or pharmacologically acceptable acid addition salts which may be formed from 2e are meant, according to the invention, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid.

Any reference to the abovementioned endothelin antagonists 2e within the scope of the present invention includes a reference to any alkali metal and alkaline earth metal salts thereof which may exist. If the compounds of formula 2e are present in the form of their basic salts, the sodium or potassium salts are particularly preferred.

Within the scope of the present invention the term antihistamines (hereinafter 2f denotes compounds selected from among epinastine, cetirizine, azelastine, fexofenadine, levocabastine, loratadine, mizolastine, ketotifen, emedastine, dimethindene, clemastine, bamipine, dexchlorpheniramine, pheniramine, doxylamine, chlorphenoxamine, dimenhydrinate, diphenhydramine, promethazine, ebastine, desloratadine and meclozine.

Preferably, compound 2f is selected from among epinastine, cetirizine, azelastine, fexofenadine, levocabastine, loratadine, ebastine, desloratadine and mizolastine, while epinastine and desloratadine are particularly preferred as compound 2 according to the invention. Most preferably, epinastine is used as compound 2f within the scope of the present invention. Any reference to the abovementioned antihistamines 2f within the scope of the present invention includes a reference to any pharmacologically acceptable acid addition salts thereof which may exist.

By the physiologically acceptable acid addition salts which may be formed from 2f are meant, according to the invention, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid or maleic acid. Preferred salts of the compounds 2f are those selected from among the acetate, hydrochloride, hydrobromide, sulfate, phosphate and methanesulfonate. In this context, hydrochlorides and hydrobromides are particularly preferred. In the case of epinastine, which is particularly preferred according to the invention, epinastine hydrochloride is of exceptional importance.

Within the scope of the present invention the term EGFR kinase inhibitors (hereinafter 2g) preferably denotes those compounds which are selected from among 4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl) amino]-quinazoline, 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, 4-[(3-chloro-4-fluoro-phenyl)amino]-7-[4-((R)-6-methyl-2-oxo-morpholin-4-yl)-butyloxy]-6-[(vinylcarbonyl)amino]-quinazoline, 4-[(3-chloro-4-fluoro-phenyl)amino]-7-[4-((S)-6-methyl-2-oxo-morpholin-4-yl)-butyloxy]-6-[(vinylcarbonyl)amino]-quinazoline, 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3 -chloro-4-fluorophenyl)amino]-6-{[4-(N,N-dimethylamino)-1-oxo-2-buten-1-yl]amino}-7-cyclopropylmethoxy-quinazoline, 4-[(3-chloro-4-fluorophenyl)amino]-6-[(4-{N-[2-(ethoxycarbonyl)-ethyl]-N-[(ethoxycarbonyl) methyl]amino}-1-oxo-2-buten-1-yl)amino]-7-cyclopropylmethoxy-quinazoline, 4-[(R)-(1-phenyl-ethyl) amino]-6-{[4-(morpholin-4-yl)-1-oxo-2-buten-1-yl] amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl) amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl) methoxy]-quinazoline, 4-[(3-chloro-4-fluorophenyl)amino]-6-[3-(morpholin-4-yl)-propyloxy]-7-methoxy-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl) quinazoline, Cetuximab, Trastuzumab, ABX-EGF and Mab ICR-62.

Preferred EGFR kinase inhibitors 2g are selected from among 4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline, 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, 4-[(3-chloro-4-fluoro-phenyl)amino]-7-[4-((R)-6-methyl-2-oxo-morpholin-4-yl)-butyloxy]-6-[(vinylcarbonyl)amino]-quinazoline, 4-[(3-chloro-4-fluoro-phenyl)amino]-7-[4-((S)-6-methyl-2-oxo-morpholin-4-yl)-butyloxy]-6-[(vinylcarbonyl)amino]-quinazoline, 4-[(3-chloro-4-fluoro-phenyl)amino]-7-[4-(2,2-dimethyl-6-oxo-morpholin-4-yl)-butyloxy]-6-[(vinylcarbonyl)amino]-quinazoline, 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(3-chloro-4-fluorophenyl)amino]-6-[(4-{N-[2-(ethoxycarbonyl)-ethyl]-N-[(ethoxycarbonyl) methyl]amino}-1-oxo-2-buten-1-yl)amino]-7-cyclopropylmethoxy-quinazoline, 4-[(R)-(1-phenyl-ethyl) amino]-6-{[4-(morpholin-4-yl)-1-oxo-2-buten-1-yl]-amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluorophenyl)amino]-6-({4-[bis-(2-methoxyethyl)-amino]-1-oxo-2-buten-1-yl}amino)-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluorophenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4 -fluorophenyl)amino]-6-{[4-(N,N-dimethylamino)-1-oxo-2-buten-1-yl]amino}-7-cyclopentyloxy-quinazoline, 4-[(3-chloro-4-fluoro-phenyl)amino]-6-{[4-((S)-2-methoxymethyl-6-oxo-morpholin-4-yl)-1-oxo-2-buten-1-yl]amino}-7-cyclopropylmethoxy-quinazoline, 4-[(R)-(1-phenyl-ethyl) amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclo-propylmethoxy-quinazoline, 4-[(R)-(1-phenyl-ethyl) amino]-6-({4-[N-(2-methoxy-ethyl)-N-methyl-amino]-1-oxo-2-buten-1-yl}amino)-7-cyclopropylmethoxyquinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-chloro-4-fluoro-phenyl)amino]-6-[(4-dimethylamino-cyclohexyl)amino]-pyrimido[5,4-d]pyrimidine or 4-[(3-chloro-4-fluorophenyl)amino]-6-[3-(morpholin-4-yl)-propyloxy]-7-methoxy-quinazoline.

Particularly preferred EGFR kinase inhibitors 2g are selected from among 4-[(3-chloro-4-fluoro-phenyl)amino]-7-[4-((R)-6-methyl-2-oxo-morpholin-4-yl)-butyloxy]-6-[(vinylcarbonyl)amino]-quinazoline, 4-[(3-chloro-4-fluoro-phenyl)amino]-7-[4-((S)-6-methyl-2-oxo-morpholin-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline, 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, 4-[(3-chloro-4-fluorophenyl)amino]-6-[(4-{N-[2-(ethoxycarbonyl)-ethyl]-N-[(ethoxycarbonyl)methyl]amino}-1-oxo-2-buten-1-yl)amino]-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopropylmethoxy-quinazoline and 4-[(3-chloro-4-fluorophenyl)amino]-6-[3-(morpholin-4-yl)-propyloxy]-7-methoxy-quinazoline.

Any reference to the abovementioned EGFR kinase inhibitors 2g also includes within the scope of the present invention a reference to any pharmacologically acceptable acid addition salts thereof which may exist.

By physiologically or pharmacologically acceptable acid addition salts which may be formed from 2g are meant according to the invention pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid. According to the invention, the salts of the compounds 2g selected from among the salts of acetic acid, hydrochloric acid, hydrobromic acid, sulphuric acid, phosphoric acid and methanesulphonic acid are preferred.

The pharmaceutical combinations of 1 and 2 according to the invention are preferably administered by inhalation. In particular in case of combinations comprising 1 and 2f also nasal application is a suitable mode of administration. Suitable inhalable powders packed into suitable capsules (inhalettes) may be administered using suitable powder inhalers. Alternatively, the drug may be inhaled by the application of suitable inhalation aerosols. These include inhalation aerosols which contain HFA134a, HFA227, or a mixture thereof as propellant gas. The drug may also be inhaled using suitable solutions of the pharmaceutical combination consisting of 1 and 2.

If the pharmaceutical combination of 1 and 2f is administered nasally, suitable solutions which may be administered by appropriate pumps can be used. Alternatively, it may be administered nasally by the application of suitable powders.

In one aspect, therefore, the invention relates to a pharmaceutical composition which contains a combination of 1 and 2.

In another aspect the present invention relates to a pharmaceutical composition which contains one or more salts 1 and one or more compounds 2, optionally in the form of their solvates or hydrates. The active substances may be combined in a single preparation or contained in two separate formulations. Pharmaceutical compositions which contain the active substances 1 and 2 in a single preparation are preferred according to the invention. However, in case the component 2 can also be administered by oral modes of administration, the instant invention is also directed to free combinations of 1 with 2. As a non-limiting example may serve the combined administration of tiotropium bromide via inhalation with roflumilast via oral administration.

In another aspect the present invention relates to a pharmaceutical composition which contains, in addition to therapeutically effective quantities of 1 and 2, a pharmaceutically acceptable excipient. In another aspect the present invention relates to a pharmaceutical composition which does not contain any pharmaceutically acceptable excipient in addition to therapeutically effective quantities of 1 and 2.

The present invention also relates to the use of 1 and 2 for preparing a pharmaceutical composition containing therapeutically effective quantities of 1 and 2 for treating inflammatory or obstructive diseases of the upper or lower respiratory tract, particularly asthma or chronic obstructive pulmonary diseases (COPD) by simultaneous or successive administration, and complications thereof such as pulmonary hypertension, as well as allergic and non-allergic rhinitis. Moreover, the pharmaceutical combinations according to the invention may be used to prepare a drug for treating cystic fibrosis or allergic alveolitis (Farmer's Lung), for example, by simultaneous or successive administration. The only reason for not using the active substance combinations according to the invention is if treatment with the second active component 2 (e.g. steroids 2a) is contraindicated for therapeutic reasons.

The present invention further relates to the simultaneous or successive use of therapeutically effective doses of the combination of the above pharmaceutical compositions 1 and 2 for treating inflammatory or obstructive respiratory tract diseases, particularly asthma or chronic obstructive pulmonary diseases (COPD), provided that treatment with steroids is not contraindicated for therapeutic reasons, by simultaneous or successive administration. The present invention also relates to the simultaneous or successive use of therapeutically effective doses of the combination of the above pharmaceutical compositions 1 and 2 for treating cystic fibrosis or allergic alveolitis (Farmer's Lung), for example.

In the active substance combinations of 1 and 2 according to the invention, ingredients 1 and 2 may be present in the form of their enantiomers, mixtures of enantiomers, or in the form of racemates.

The proportions in which the two active substances 1 and 2 may be used in the active substance combinations according to the invention are variable. Active substances 1 and 2 may possibly be present in the form of their solvates or hydrates. Depending on the choice of the compounds 1 and 2, the weight ratios which may be used within the scope of the present invention vary on the basis of the different molecular weights of the various compounds and their different potencies.

As a rule, the pharmaceutical combinations according to the invention may contain compounds 1 and steroids 2a in ratios by weight ranging from 1:300 to 50:1, preferably from 1:250 to 40:1. In the particularly preferred pharmaceutical combinations which contain tiotropium salt as compound 1 and a compound selected from among budesonide, fluticasone, mometasone, and ciclesonide as the steroid 2a, the weight ratios of 1 to 2a are most preferably in a range in which tiotropium 1' and 2a are present in proportions of 1:150 to 30:1, more preferably from 1:50 to 20:1.

For example, without restricting the scope of the invention thereto, preferred combinations of 1 and 2a according to the invention may contain 1' and steroid 2a in the following weight ratios: 1:50; 1:49; 1:48; 1:47; 1:46; 1:45; 1:44; 1:43; 1:42; 1:41; 1:40; 1:39; 1:38; 1:37; 1:36; 1:35; 1:34; 1:33; 1:32; 1:31; 1:30; 1:29; 1:28; 1:27; 1:26; 1:25; 1:24; 1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1; 11:1; 12:1; 13:1; 14:1; 15:1; 16:1; 17:1; 18:1; 19:1; 20:1.

The pharmaceutical compositions according to the invention containing the combinations of 1 and 2a are normally administered so that 1 and 2a are present together in doses of 0.01 µg to 10000 µg, preferably from 0.1 µg to 2000 µg, more preferably from 1 µg to 1000 µg, better still from 5 µg to 500 µg, preferably, according to the invention, from 10 µg to 300 µg, better still 20 µg to 200 µg per single dose. For example, combinations of 1 and 2a according to the invention contain a quantity of tiotropium 1' and steroid 2a such that the total dosage per single dose is about 20 µg, 25 µg, 30 µg, 35 µg, 45 µg, 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, 260 µg, 265 µg, 270 µg, 275 µg, or similar. In these dosage ranges, active substances 1' and 2a may be present in the weight ratios mentioned earlier.

For example, without restricting the scope of the invention thereto, the combinations of 1 and 2a according to the invention may contain a quantity of tiotropium 1' and steroid 2a such that, for each single dose, 5 µg of 1' and 25 µg of 2a; 5 µg of 1' and 50 µg of 2a; 5 µg of 1' and 100 µg of 2a; 5 µg of 1' and 125 µg of 2a; 5 µg of 1' and 200 µg of 2a; 5 µg of 1' and 250 µg of 2a; 10 µg of 1' and 25 µg of 2a; 10 µg of 1' and 50 µg of 2a; 10 µg of 1' and 100 µg of 2a; 10 µg of 1' and 125 µg of 2a; 10 µg of 1' and 200 µg of 2a; 10 µg of 1' and 250 µg of 2a; 18 µg of 1' and 25 µg of 2a; 18 µg of 1' and 50 µg of 2a; 18 µg of 1' and 100 µg of 2a; 18 µg of 1' and 125 µg of 2a; 18 µg of 1' and 200 µg of 2a; 18 µg of 1' and 250 µg of 2a; 20 µg of 1' and 25 µg of 2a; 20 µg of 1' and 50 µg of 2a; 20 µg of 1' and 100 µg of 2a; 20 µg of 1' and 125 µg of 2a; 20 µg of 1' and 200 µg of 2a; 20 µg of 1' and 250 µg of 2a; 36 µg of 1' and 25 µg of 2a; 36 µg of 1' and 50 µg of 2a; 36 µg of 1' and 100 µg of 2a; 36 µg of 1' and 125 µg of 2a; 36 µg of 1' and 200 µg of 2a; 36 µg of 1' and 250 µg of 2a; 40 µg of 1' and 25 µg of 2a; 40 µg of 1' and 50 µg of 2a; 40 µg of 1' and 100 µg of 2a; 40 µg of 1' and 125 µg of 2a; 40 µg of 1' and 200 µg of 2a; or 40 µg of 1' and 250 µg of 2a are administered.

If the active substance combination in which 1 denotes tiotropium bromide is used as the preferred combination of 1 and 2a according to the invention, the quantities of active substance 1' and 2a administered per single dose mentioned by way of example correspond to the following quantities of 1 and 2a administered per single dose: 6 µg of 1 and 25 µg of 2a; 6 µg of 1 and 50 µg of 2a; 6 µg of 1 and 100 µg of 2a; 6 µg of 1 and 125 µg of 2a; 6 µg of 1 and 200 µg of 2a; 6 µg of 1 and 250 µg of 2a; 12 µg of 1 and 25 µg of 2a; 12 µg of 1 and 50 µg of 2a; 12 µg of 1 and 100 µg of 2a; 12 µg of 1 and 125 µg of 2a; 12 µg of 1 and 200 µg of 2a; 12 µg of 1 and 250 µg of 2a; 21.7 µg of 1 and 25 µg of 2a; 21.7 µg of 1 and 50 µg of 2a; 21.7 µg of 1 and 100 µg of 2a; 21.7 µg of 1 and 125 µg of 2a; 21.7 µg of 1 and 200 µg of 2a; 21.7 µg of 1 and 250 µg of 2a; 24.1 µg of 1 and 25 µg of 2a; 24.1 µg of 1 and 50 µg of 2a; 24.1 µg of 1 and 100 µg of 2a; 24.1 µg of 1 and 125 µg of 2a; 24.1 µg of 1 and 200 µg of 2a; 24.1 µg of 1 and 250 µg of 2a; 43.3 µg of 1 and 25 µg of 2a; 43.3 µg of 1 and 50 µg of 2a; 43.3 µg of 1 and 100 µg of 2a; 43.3 µg of 1 and 125 µg of 2a; 43.3 µg of 1 and 200 µg of 2a; 43.3 µg of 1 and 250 µg of 2a; 48.1 µg of 1 and 25 µg of 2a; 48.1 µg of 1 and 50 µg of 2a; 48.1 µg of 1 and 100 µg of 2a; 48.1 µg of 1 and 125 µg of 2a; 48.1 µg of 1 and 200 µg of 2a; or 48.1 µg of 1 and 250 µg of 2a.

If the active substance combination in which 1 is tiotropium bromide monohydrate is used as the preferred combination of 1 and 2a according to the invention, the quantities of 1' and 2a administered per single dose specified by way of example hereinbefore correspond to the following quantities of 1 and 2a administered per single dose: 6.2 µg of 1 and 25 µg of 2a; 6.2 µg of 1 and 50 µg of 2a; 6.2 µg of 1 and 100 µg of 2a; 6.2 µg of 1 and 125 µg of 2a; 6.2 µg of 1 and 200 µg of 2a; 6.2 µg of 1 and 250 µg of 2a; 12.5 µg of 1 and 25 µg of 2a; 12.5 µg of 1 and 50 µg of 2a; 12.5 µg of 1 and 100 µg of 2a; 12.5 µg of 1 and 125 µg of 2a; 12.5 µg of 1 and 200 µg of 2a; 12.5 µg of 1 and 250 µg of 2a; 22.5 µg of 1 and 25 µg of 2a; 22.5 µg of 1 and 50 µg of 2a; 22.5 µg of 1 and 100 µg of 2a; 22.5 µg of 1 and 125 µg of 2a; 22.5 µg of 1 and 200 µg of 2a; 22.5 µg of 1 and 250 µg of 2a; 25 µg of 1 and 25 µg of 2a; 25 µg of 1 and 50 µg of 2a; 25 µg of 1 and 100 µg of 2a; 25 µg of 1 and 125 µg of 2a; 25 µg of 1 and 200 µg of 2a; 25 µg of 1 and 250 µg of 2a; 45 µg of 1 and 25 µg of 2a; 45 µg of 1 and 50 µg of 2a; 45 µg of 1 and 100 µg of 2a; 45 µg of 1 and 125 µg of 2a; 45 µg of 1 and 200 µg of 2a; 45 µg of 1 and 250 µg of 2a; 50 µg of 1 and 25 µg of 2a; 50 µg of 1 and 50 µg of 2a; 50 µg of 1 and 100 µg of 2a; 50 µg of 1 and 125 µg of 2a; 50 µg of 1 and 200 µg of 2a; or 50 µg of 1 and 250 µg of 2a.

As a rule, the pharmaceutical combinations according to the invention may contain compounds 1 and 2b in ratios by weight ranging from 1:300 to 50:1, preferably from 1:250 to 40:1. In the particularly preferred pharmaceutical combinations which contain ipratropium salt or tiotropium salt as compound 1 and a compound selected from among pramipexol, talipexol and viozan as the dopamine agonist 2b, the weight ratios of 1 to 2b are most preferably in a range in which ipratropium or tiotropium 1' and 2b are present in proportions of 1:150 to 30:1, more preferably from 1:50 to 20:1.

For example, without restricting the scope of the invention thereto, preferred combinations of 1 and 2b according to the invention may contain ipratropium or tiotropium 1' and dopamine agonists 2b in the following weight ratios: 1:50; 1:49; 1:48; 1:47; 1:46; 1:45; 1:44; 1:43; 1:42; 1:41; 1:40; 1:39; 1:38; 1:37; 1:36; 1:35; 1:34; 1:33; 1:32; 1:31; 1:30; 1:29; 1:28; 1:27; 1:26; 1:25; 1:24; 1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1; 11:1; 12:1; 13:1; 14:1; 15:1; 16:1; 17:1; 18:1; 19:1; 20:1.

The pharmaceutical compositions according to the invention containing the combinations of 1 and 2b are normally administered so that 1 and 2b are present together in doses of 0.01 to 100000 µg, preferably from 0.1 to 2000 µg, more preferably from 1 to 1000 μg, better still from 5 to 600 μg, per single dose. For example, combinations of 1 and 2b according to the invention contain a quantity of 1' and dopamine agonist 2b such that the total dosage per single dose is about 20 μg, 25 μg, 30 μg, 35 μg, 45 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, 160 μg, 165 μg, 170 μg, 175 μg, 180 μg, 185 μg, 190 μg, 195 μg, 200 μg, 205 μg, 210 μg, 215 μg, 220 μg, 225 μg, 230 μg, 235 μg, 240 μg, 245 μg, 250 μg, 255 μg, 260 μg, 265 μg, 270 μg, 275 μg, 280 μg, 285 μg, 290 μg, 295 μg, 300 μg, 305 μg, 310 μg, 315 μg, 320 μg, 325 μg, 330 μg, 335 μg, 340 μg, 345 μg, 350 μg, 355 μg, 360 μg, 365 μg, 370 μg, 375 μg, 380 μg, 385 μg, 390 μg, 395 μg, 400 μg, 405 μg, 410 μg, 415 μg, 420 μg, 425 μg, 430 μg, 435 μg, 440 μg, 445 μg, 450 μg, 455 μg, 460 μg, 465 μg, 470 μg, 475 μg, 480 μg, 485 μg, 490 μg, 495 μg, 500 μg, 505 μg, 510 μg, 515 μg, 520 μg or similar. The suggested dosages per single dose specified above are not to be regarded as being limited to the numerical values actually stated, but are intended as dosages which are disclosed by way of example. Of course, dosages which may fluctuate about the abovementioned numerical values within a range of about +/−2.5 μg are also included in the values given above by way of example. In these dosage ranges, the active substances 1' and 2b may be present in the weight ratios given above.

For example, without restricting the scope of the invention thereto, the combinations of 1 and 2b according to the invention may contain a quantity of 1' and dopamine agonist 2b such that, for each single dose, 5 μg of 1' and 25 μg of 2b, 5 μg of 1' and 45 μg of 2b, 5 μg of 1' and 50 μg of 2b, 5 μg of 1' and 100 μg of 2b, 5 μg of 1' and 200 μg of 2b, 5 μg of 1' and 250 μg of 2b, 5 μg of 1' and 270 μg of 2b, 5 μg of 1' and 400 μg of 2b, 5 μg of 1' and 495 μg of 2b, 10 μg of 1' and 25 μg of 2b, 10 μg of 1' and 45 μg of 2b, 10 μg of 1' and 50 μg of 2b, 10 μg of 1' and 100 μof 2b, 10 μg of 1' and 200 μg of 2b, 10 μg of 1' and 250 μg of 2b, 10 μg of 1' and 270 μg of 2b, 101 μg of 1' and 400 μg of 2b, 10 μg of 1' and 495 μg of 2b, 18 μg of 1' and 25 μg of 2b, 18 μg of 1' and 45 μg of 2b, 18 μg of 1' and 50 μg of 2b, 18 μg of 1' and 1000 μg of 2b, 18 μg of 1' and 200 μg of 2b, 18 μg of 1' and 250 μg of 2b, 18 μg of 1' and 270 μg of 2b, 18 μg of 1' and 400 μg of 2b, 18 μg of 1' and 495 μg of 2b, 20 μg of 1' and 25 μg of 2b, 20 μg of 1' and 45 μg of 2b, 20 μg of 1' and 50 μg of 2b, 20 μg of 1' and 100 μg of 2b, 20 μg of 1' and 200 μg of 2b, 20 μg of 1' and 250 μg of 2b, 20 μg of 1' and 270 μg of 2b, 20 μg of 1' and 400 μg of 2b, 20 μg of 1' and 495 μg of 2b, 36 μg of 1' and 25 μg of 2b, 36 μg of 1' and 45 μg of 2b, 36 μg of 1' and 50 μg of 2b, 36 μg of 1' and 100 μg of 2b, 36 μg of 1' and 200 μg of 2b, 36 μg of 1' and 250 μg of 2b, 36 μg of 1' and 270 μg of 2b, 36 μg of 1' and 400 μg of 2b, 36 μg of 1' and 495 μg of 2b, 40 μg of 1' and 25 μg of 2b, 40 μg of 1' and 45 μg of 2b, 40 μg of 1' and 50 μg of 2b, 40 μg of 1' and 100 μg of 2b, 40 μg of 1' and 200 μg of 2b, 40 μg of 1' and 250 μg of 2b, 40 μg of 1' and 270 μg of 2b, 40 μg of 1' and 400 μg of 2b or 40 μg of 1' and 495 μg of 2b are administered.

If the active substance combination in which 1 denotes tiotropium bromide is used as the preferred combination of 1 and 2b according to the invention, the quantities of active substance 1' and 2b administered per single dose mentioned by way of example correspond to the following quantities of 1 and 2b administered per single dose: 6 μg of 1 and 25 μg of 2b, 6 μg of 1 and 45 μg of 2b, 6 μg of 1 and 50 μg of 2b, 6 μg of 1 and 100 μg of 2b, 6 μg of 1 and 200 μg of 2b, 6 μg of 1 and 250 μg of 2b, 6 μg of 1 and 270 μg of 2b, 6 μg of 1 and 400 μg of 2b, 6 μg of 1 and 495 μg of 2b, 12 μg of 1 and 25 μg of 2b, 12 μg of 1 and 45 μg of 2b, 12 μg of 1 and 50 μg of 2b, 12 μg of 1 and 1000 μg of 2b, 12 μg of 1 and 200 μg of 2b, 12 μg of 1 and 250 μg of 2b, 12 μg of 1 and 270 μg of 2b, 12 μg of 1 and 400 μg of 2b, 12 μg of 1 and 495 μg of 2b, 21.7 μg of 1 and 25 μg of 2b, 21.7 μg of 1 and 45 μg of 2b, 21.7 μg of 1 and 50 μg of 2b, 21.7 μg of 1 and 1001 μg of 2b, 21.7 μg of 1 and 200 μg of 2b, 21.7 μg of 1 and 250 μg of 2b, 21.7 μg of a and 270 μg of 2b, 21.7 μg of 1 and 400 μg of 2b, 21.7 μg of 1 and 495 μg of 2b, 24.1 μg of 1 and 25 μg of 2b, 24.1 μg of 1 and 45 μg of 2b, 24.1 μg of 1 and 50 μg of 2b, 24.1 μg of 1 and 1000 μg of 2b, 24.1 μg of 1 and 200 μg of 2b, 24.1 μg of 1 and 250 μg of 2b, 24.1 μg of 1 and 270 μg of 2b, 24.1 μg of 1 and 400 μg of 2b, 24.1 μg of 1 and 495 μg of 2b, 43.3 μg of 1 and 25 μg of 2b, 43.3 μg of 1 and 45 μg of 2b, 43.3 μg of 1 and 50 μg of 2b, 43.3 μg of 1 and 100 μg of 2b, 43.3 μg of 1 and 200 μg of 2b, 43.3 μg of 1 and 250 μg of 2b, 43.3 μg of 1 and 270 μg of 2b, 43.3 μg of 1 and 400 μg of 2b, 43.3 μg of 1 and 495 μg of 2b, 48.1 μg of 1 and 25 μg of 2b, 48.1 μg of 1 and 45 μg of 2b, 48.1 μg of 1 and 50 μg of 2b, 48.1 μg of 1 and 10 μg of 2b, 48.1 μg of 1 and 200 μg of 2b, 48.1 μg of 1 and 250 μg of 2b, 48.1 μg of 1 and 270 μg of 2b, 48.1 μg of 1 and 400 μg of 2b, 48.1 μg of 1 and 495 μg of 2b.

If the active substance combination in which 1 is tiotropium bromide monohydrate is used as the preferred combination of 1 and 2b according to the invention, the quantities of 1' and 2b administered per single dose specified by way of example hereinbefore correspond to the following quantities of 1 and 2b administered per single dose: 6,2 μg of 1 and 25 μg of 2b, 6,2 μg of 1 and 45 μg of 2b, 6,2 μg of 1 and 50 μg of 2b, 6,2 μg of 1 and 100 μg of 2b, 6,2 μg of 1 and 200 μg of 2b, 6,2 μg of 1 and 250 μg of 2b, 6,2 μg of 1 and 270 μg of 2b, 6,21 μg of 1 and 400 μg of 2b, 6,2 μg of 1 and 495 μg of 2b, 12,5 μg of 1 and 25 μg of 2b, 12,51 μg of 1 and 45 μg of 2b, 12,5 μg of 1 and 50 μg of 2b, 12,5 μg of 1 and 100 μg of 2b, 12,5 μg of 1 and 200 μg of 2b, 12,5 μg of 1 and 250 μg of 2b, 12,5 μg of 1 and 270 μg of 2b, 12,5 μg of 1 and 400 μg of 2b, 12,5 μg of 1 and 495 μg of 2b, 22,5 μg of 1 and 25 μg of 2b, 22,5 μg of 1 and 45 μg of 2b, 22,5 μg of 1 and 50 μg of 2b, 22,5 μg of 1 and 100 μg of 2b, 22,5 μg of 1 and 200 μg of 2b, 22,5 μg of 1 and 250 μg of 2b, 22,5 μg of 1 and 270 μg of 2b, 22,5 μg of 1 and 400 μg of 2b, 22,5 μg of 1 and 495 μg of 2b, 25 μg of 1 and 25 μg of 2b, 25 μg of 1 and 45 μg of 2b, 25 μg of 1 and 50 μg of 2b, 25 μg of 1 and 100 μg of 2b, 25 μg of 1 and 200 μg of 2b, 25 μg of 1 and 250 μg of 2b, 25 μg of 1 and 270 μg of 2b, 25 μg of 1 and 400 μg of 2b, 25 μg of 1 and 495 μg of 2b, 45 μg of 1 and 25 μg of 2b, 45 μg of 1 and 45 μg of 2b, 45 μg of 1 and 50 μg of 2b, 45 μg of 1 and 1001 μg of 2b, 45 μg of 1 and 200 μg of 2b, 45 μg of 1 and 250 μg of 2b, 45 μg of 1 and 270 μg of 2b, 45 μg of 1 and 400 μg of 2b, 45 μg of 1 and 495 μg of 2b, 50 μg of 1 and 25 μg of 2b, 50 μg of 1 and 45 μg of 2b, 50 μg of 1 and 50 μg of 2b, 50 μg of 1 and 100 μg of 2b, 50 μg of 1 and 200 μg of 2b, 50 μg of 1 and 250 μg of 2b, 50 μg of 1 and 270 μg of 2b, 50 μg of 1 and 400 μg of 2b, 501 μg of 1 and 495 μg of 2b. The pharmaceutical combinations according to the invention may contain compounds 1 and 2c in ratios by weight ranging from 1:300 to 50:1, preferably from 1:250 to 40:1. In the particularly preferred pharmaceutical combinations which contain tiotropium salt as compound 1, the weight ratios of 1 to 2c are most preferably in a range in which ipratropium or tiotropium 1' and 2c are present in proportions of 1:150 to 30:1, more preferably from 1:50 to 20:1.

For example, without restricting the scope of the invention thereto, preferred combinations of 1 and 2c according to the invention may contain tiotropium 1' and PDE-IV inhibitor 2c in the following weight ratios: 1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1:62, 1:61, 1:60, 1:59, 1:58, 1:57, 1:56, 1:55, 1:54, 1:53, 1:52, 1:51, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24;

1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1; 11:1; 12:1; 13:1; 14:1; 15:1; 16:1; 17:1; 18:1; 19:1; 20:1.

The pharmaceutical compositions according to the invention containing the combinations of 1 and 2c are normally administered so that 1 and 2c are present together in doses of 0.01 to 10000 µg, preferably from 0.1 to 2000 µg, more preferably from 1 to 1500 µg, better still from 50 to 1200 µg per single dose. For example, combinations of 1 and 2c according to the invention contain a quantity of tiotropium 1' and PDE-IV inhibitor 2c such that the total dosage per single dose is about 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, 260 µg, 265 µg, 270 µg, 275 µg, 280 µg, 2851 µg, 290 µg, 295 µg, 300 µg, 305 µg, 310 µg, 315 µg, 320 µg, 325 µg, 330 µg, 335 µg, 340 µg, 345 µg, 350 µg, 355 µg, 360 µg, 365 µg, 370 µg, 375 µg, 380 µg, 385 µg, 390 µg, 395 µg, 400 µg, 405 µg, 410 µg, 415 µg, 420 µg, 425 µg, 430 µg, 435 µg, 440 µg, 445 µg, 450 µg, 455 µg, 460 µg, 465 µg, 470 µg, 475 µg, 480 µg, 485 µg, 490 µg, 495 µg, 500 µg, 505 µg, 510 µg, 515 µg, 520 µg, 525 µg, 530 µg, 535 µg, 540 µg, 545 µg, 550 µg, 555 µg, 560 µg, 565 µg, 570 µg, 575 µg, 580 µg, 585 µg, 590 µg, 595 µg, 600 µg, 605 µg, 610 µg, 615 µg, 620 µg, 625 µg, 630 µg, 635 µg, 640 µg, 645 µg, 650 µg, 655 µg, 660 µg, 665 µg, 670 µg, 675 µg, 680 µg, 685 µg, 690 µg, 695 µg, 700 µg, 705 µg, 710 µg, 715 µg, 720 µg, 725 µg, 730 µg, 735 µg, 740 µg, 745 µg, 750 µg, 755 µg, 760 µg, 765 µg, 770 µg, 775 µg, 780 µg, 785 µg, 790 µg, 795 µg, 800 µg, 805 µg, 810 µg, 815 µg, 820 µg, 825 µg, 830 µg, 835 µg, 840 µg, 845 µg, 850 µg, 855 µg, 860 µg, 865 µg, 870 µg, 875 µg, 880 µg, 885 µg, 890 µg, 895 µg, 900 µg, 905 µg, 910 µg, 915 µg, 920 µg, 925 µg, 930 µg, 935 µg, 940 µg, 945 µg, 950 µg, 955 µg, 960 µg, 965 µg, 970 µg, 975 µg, 980 µg, 985 µg, 990 µg, 995 µg, 1000 µg, 1005 µg, 1010 µg, 1015 µg, 1020 µg, 1025 µg, 1030 µg, 1035 µg, 1040 µg, 1045 µg, 1050 µg, 1055 µg, 1060 µg, 1065 µg, 1070 µg, 1075 µg, 1080 µg, 1085 µg, 1090 µg, 1095 µg, 1110 µg or similar. The suggested dosages per single dose specified above are not to be regarded as being limited to the numerical values actually stated, but are intended as dosages which are disclosed by way of example. Of course, dosages which may fluctuate about the above-mentioned numerical values within a range of about +/−2.5 µg are also included in the values given above by way of example. In these dosage ranges, the active substances 1' and 2c may be present in the weight ratios given above.

For example, without restricting the scope of the invention thereto, the combinations of 1 and 2c according to the invention may contain a quantity of tiotropium 1' and PDE-IV inhibitor 2c such that, for each single dose, 5 µg of 1' and 25 µg of 2c, 5 µg of 1' and 50 µg of 2c, 5 µg of 1' and 100 µg of 2c, 51 µg of 1' and 200 µg of 2c, 5 µg of 1' and 300 µg of 2c, 5 µg of 1' and 400 µg of 2c, 5 µg of 1' and 500 µg of 2c, 51 µg of 1' and 600 µg of 2c, 5 µg of 1' and 700 µg of 2c, 51 µg of 1' and 800 µg of 2c, 5 µg of 1' and 900 µg of 2c, 5 µg of 1' and 1000 µg of 2c, 10 µg of 1' and 25 µg of 2c, 10 µg of 1' and 50 µg of 2c, 10 µg of 1' and 100 µg of 2c, 10 µg of 1' and 200 µg of 2c, 10 µg of 1' and 300 µg of 2c, 10 µg of 1' and 400 µg of 2c, 10 µg of 1' and 500 µg of 2c, 10 µg of 1' and 600 µg of 2c, 10 µg of 1' and 700 µg of 2c, 10 µg of 1' and 800 µg of 2c, 10 µg of 1' and 900 µg of 2c, 10 µg of 1' and 1000 µg of 2c, 18 µg of 1' and 25 µg of 2c, 18 µg of 1' and 50 µg of 2c, 18 µg of 1' and 100 µg of 2c, 18 µg of 1' and 200 µg of 2c, 18 µg of 1' and 300 µg of 2c, 18 µg of 1' and 400 µg of 2c, 18 µg of 1' and 500 µg of 2c, 18 µg of 1' and 600 µg of 2c, 18 µg of 1' and 700 µg of 2c, 18 µg of 1' and 800 µg of 2c, 18 µg of 1' and 900 µg of 2c, 18 µg of 1' and 1000 µg of 2c, 20 µg of 1' and 25 µg of 2c, 20 µg of 1' and 50 µg of 2c, 20 µg of 1' and 50 µg of 2c, 20 µg of 1' and 100 µg of 2c, 20 µg of 1' and 200 µg of 2c, 20 µg of 1' and 300 µg of 2c, 20 µg of 1' and 400 µg of 2c, 20 µg of 1' and 500 µg of 2c, 20 µg of 1' and 600 µg of 2c, 20 µg of 1' and 700 µg of 2c, 20 µg of 1' and 800 µg of 2c, 20 µg of 1' and 900 µg of 2c, 20 µg of 1' and 1000 µg of 2c, 36 µg of 1' and 25 µg of 2c, 36 µg of 1' and 50 µg of 2c, 36 µg of 1' and 100 µg of 2c, 36 µg of 1' and 200 µg of 2c, 36 µg of 1' and 300 µg of 2c, 36 µg of 1' and 400 µg of 2c, 36 µg of 1' and 500 µg of 2c, 36 µg of 1' and 600 µg of 2c, 36 µg of 1' and 700 µg of 2c, 36 µg of 1' and 800 µg of 2c, 36 µg of 1' and 900 µg of 2c, 36 µg of 1' and 1000 µg of 2c, 40 µg of 1' and 25 µg of 2c, 40 µg of 1' and 50 µg of 2c, 40 µg of 1' and 100 µg of 2c, 40 µg of 1' and 200 µg of 2c, 40 µg of 1' and 300 µg of 2c, 40 µg of 1' and 400 µg of 2c, 40 µg of 1' and 500 µg of 2c, 40 µg of 1' and 600 µg of 2c or 40 µg of 1' and 700 µg of 2c, 40 µg of 1' and 800 µg of 2c, 40 µg of 1' and 900 µg of 2c, 40 µg of 1' and 10000 µg of 2c are administered.

If the active substance combination in which 1 denotes tiotropium bromide is used as the preferred combination of 1 and 2c according to the invention, the quantities of active substance 1' and 2c administered per single dose mentioned by way of example correspond to the following quantities of 1 and 2c administered per single dose: 6 µg of 1 and 25 µg of 2c, 6 µg of 1 and 50 µg of 2c, 6 µg of 1 and 100 µg of 2c, 6 µg of 1 and 200 µg of 2c, 6 µg of 1 and 300 µg of 2c, 6 µg of 1 and 400 µg of 2c, 6 µg of 1 and 500 µg of 2c, 6 µg of 1 and 600 µg of 2c, 6 µg of 1 and 700 µg of 2c, 6 µg of 1 and 800 µg of 2c, 6 µg of 1 and 900 µg of 2c, 6 µg of 1 and 1000 µg of 2c, 12 µg of 1 and 25 µg of 2c, 12 µg of 1 and 50 µg of 2c, 121 µg of 1 and 100 µg of 2c, 12 µg of 1 and 200 µg of 2c, 12 µg of 1 and 300 µg of 2c, 12 µg of 1 and 400 µg of 2c, 12 µg of 1 and 500 µg of 2c, 12 µg of 1 and 600 µg of 2c, 12 µg of 1 and 700 µg of 2c, 12 µg of 1 and 800 µg of 2c, 12 µg of 1 and 900 µg of 2c, 12 µg of 1 and 1000 µg of 2c 21.7 µg of 1 and 25 µg of 2c, 21.7 µg of 1 and 50 µg of 2c, 21.7 µg of 1 and 100 µg of 2c, 21.71 µg of 1 and 200 µg of 2c, 21.7 µg of 1 and 300 µg of 2c, 21.7 µg of 1 and 400 µg of 2c, 21.7 µg of 1 and 500 µg of 2c, 21.7 µg of 1 and 600 µg of 2c, 21.71 µg of 1 and 700 µg of 2c, 21.7 µg of 1 and 800 µg of 2c, 21.7 µg of 1 and 900 µg of 2c, 21.7 µg of 1 and 1000 µg of 2c, 24.1 µg of 1 and 25 µg of 2c, 24.1 µg of 1 and 50 µg of 2c, 24.1 µg of 1 and 100 µg of 2c, 24.1 µg of 1 and 200 µg of 2c, 24.1 µg of 1 and 300 µg of 2c, 24.1 µg of 1 and 400 µg of 2c, 24.1 µg of 1 and 500 µg of 2c, 24.1 µg of 1 and 600 µg of 2c, 24.1 µg of 1 and 700 µg of 2c, 24.1 µg of 1 and 800 µg of 2c, 24.1 µg of 1 and 900 µg of 2c, 24.1 µg of 1 and 1000 µg of 2c, 43.3 µg of 1 and 25 µg of 2c, 43.3 µg of 1 and 50 µg of 2c, 43.3 µg of 1 and 100 µg of 2c, 43.3 µg of 1 and 200 µg of 2c, 43.3 µg of 1 and 300 µg of 2c, 43.3 µg of 1 and 400 µg of 2c, 43.3 µg of 1 and 500 µg of 2c, 43.3 µg of 1 and 600 µg of 2c, 43.3 µg of 1 and 700 µg of 2c, 43.3 µg of 1 and 800 µg of 2c, 43.3 µg of 1 and 900 µg of 2c, 43.3 µg of 1 and 1000 µg of 2c, 48.1 µg of 1 and 25 µg of 2c, 48.1 µg of 1 and 50 µg of 2c, 48.1 µg of 1 and 100 µg of 2c, 48.1 µg of 1 and 200 µg of 2c, 48.1 µg of 1 and 300 µg of 2c, 48.1 µg of 1 and 400 µg of 2c, 48.1 µg of 1 and 500 µg of 2c, 48.1 µg of 1 and 600 µg of 2c, 48.1 µg of 1 and 700 µg of 2c, 48.1 µg of 1 and 800 µg of 2c, 48.1 µg of 1 and 900 µg of 2c, 48.1 µg of 1 and 1000 µg of 2c.

If the active substance combination in which 1 is tiotropium bromide monohydrate is used as the preferred combination of 1 and 2c according to the invention, the quantities of 1' and 2c administered per single dose specified by way of example hereinbefore correspond to the following quantities of 1 and 2c administered per single dose: 6.2 µg of 1 and 25 µg of 2c, 6.2 µg of 1 and 50 µg of 2c, 6.2 µg of 1 and 100 µg of 2c, 6.2 µg of 1 and 200 µg of 2c, 6.2 µg of 1 and 300 µg of 2c, 6.2 µg of 1 and 400 µg of 2c, 6.2 µg of 1 and 500 µg of 2c, 6.2 µg of 1 and 600 µg of 2c, 6.2 µg of 1 and 700 µg of 2c, 6.2 µg of 1 and 800 µg of 2c, 6.2 µg of 1 and 900 µg of 2c, 6.2 µg of 1 and 1000 µg of 2c, 12.5 µg of 1 and 25 µg of 2c, 12.5 µg of 1 and 50 µg of 2c, 12.5 µg of 1 and 100 µg of 2c, 12.5 µg of 1 and 200 µg of 2c, 12.5 µg of 1 and 300 µg of 2c, 12.5 µg of 1 and 400 µg of 2c, 12.5 µg of 1 and 500 µg of 2c, 12.5 µg of 1 and 600 µg of 2c, 12.51 µg of 1 and 700 µg of 2c, 12.5 µg of 1 and 800 µg of 2c, 12.5 µg of 1 and 900 µg of 2c, 12.5 µg of 1 and 1000 µg of 2c, 22.5 µg of 1 and 25 µg of 2c, 22.5 µg of 1 and 50 µg of 2c, 22.5 µg of 1 and 100 µg of 2c, 22.5 µg of 1 and 200 µg of 2c, 22.5 µg of 1 and 300 µg of 2c, 22.5 µg of 1 and 400 µg of 2c, 22.5 µg of 1 and 500 µg of 2c, 22.5 µg of 1 and 600 µg of 2c, 22.5 µg of 1 and 700 µg of 2c, 22.5 µg of 1 and 800 µg of 2c, 22.5 µg of 1 and 900 µg of 2c, 22.5 µg of 1 and 1000 µg of 2c, 25 µg of 1 and 25 µg of 2c, 25 µg of 1 and 50 µg of 2c, 25 µg of 1 and 100 µg of 2c, 25 µg of 1 and 200 µg of 2c, 25 µg of 1 and 300 µg of 2c, 25 µg of 1 and 400 µg of 2c, 25 µg of 1 and 500 µg of 2c, 25 µg of 1 and 600 µg of 2c, 25 µg of 1 and 700 µg of 2c, 25 µg of 1 and 800 µg of 2c, 25 µg of 1 and 900 µg of 2c, 25 µg of 1 and 1000 µg of 2c, 45 µg of 1 and 25 µg of 2c, 45 µg of 1 and 50 µg of 2c, 45 µg of 1 and 100 µg of 2c, 45 µg of 1 and 200 µg of 2c, 45 µg of 1 and 300 µg of 2c, 45 µg of 1 and 400 µg of 2c, 45 µg of 1 and 500 µg of 2c, 45 µg of 1 and 600 µg of 2c, 45 µg of 1 and 700 µg of 2c, 45 µg of 1 and 800 µg of 2c, 45 µg of 1 and 900 µg of 2c, 45 µg of 1 and 1000 µg of 2c, 50 µg of 1 and 25 µg of 2c, 50 µg of 1 and 50 µg of 2c, 50 µg of 1 and 100 µg of 2c, 50 µg of 1 and 200 µg of 2c, 50 µg of 1 and 300 µg of 2c, 50 µg of 1 and 400 µg of 2c, 50 µg of 1 and 500 µg of 2c, 50 µg of 1 and 600 µg of 2c, 50 µg of 1 and 700 µg of 2c, 50 µg of 1 and 800 µg of 2c, 50 µg of 1 and 900 µg of 2c or 50 µg of 1 and 1000 µg of 2c.

As a rule, the pharmaceutical combinations according to the invention may contain compounds 1 and 2d in ratios by weight ranging from 1:300 to 50:1, preferably from 1:250 to 40:1. In the particularly preferred pharmaceutical combinations which contain tiotropium salt as compound 1 and a compound selected from among BIIF 1149, CGP 60829, MK-869, CJ-11974, GR 205171, N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide, N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide, N-[2-(3,5-bis-trifluoromethyl-phenyl)-ethyl]-2-[4-(cyclopropylmethyl-methyl-amino)-piperidin-1-yl]-N-methyl-2-phenyl-acetamide, N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide and N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide and the arylglycinamide derivatives of formula 3 as $NK_1$-receptor antagonist 2d, the weight ratios of 1 to 2d are most preferably in a range in which tiotropium 1' and 2d are present in proportions of 1:150 to 30:1, more preferably from 1:50 to 20:1.

For example, without restricting the scope of the invention thereto, preferred combinations of 1 and 2d according to the invention may contain tiotropium 1' and $NK_1$-receptor antagonist 2d in the following weight ratios:

1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1:62, 1:61, 1:60, 1:59, 1:58, 1:57, 1:56, 1:55, 1:54, 1:53, 1:52, 1:51, 1:50; 1:49; 1:48; 1:47; 1:46; 1:45; 1:44; 1:43; 1:42; 1:41; 1:40; 1:39; 1:38; 1:37; 1:36; 1:35; 1:34; 1:33; 1:32; 1:31; 1:30; 1:29; 1:28; 1:27; 1:26; 1:25; 1:24; 1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1; 11:1; 12:1; 13:1; 14:1; 15:1; 16:1; 17:1; 18:1; 19:1; 20:1.

The pharmaceutical compositions according to the invention containing the combinations of 1 and 2d are normally administered so that 1 and 2d are present together in doses of 0.01 to 10000 µg, preferably from 0.1 to 2000 µg, more preferably from 1 to 1500 µg, better still from 50 to 1200 µg per single dose. For example, combinations of 1 and 2d according to the invention contain a quantity of tiotropium 1' and $NK_1$-receptor antagonist 2d such that the total dosage per single dose is about 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, 260 µg, 265 µg, 270 µg, 275 µg, 280 µg, 285 µg, 290 µg, 295 µg, 300 µg, 305 µg, 310 µg, 315 µg, 320 µg, 325 µg, 330 µg, 335 µg, 340 µg, 345 µg, 350 µg, 355 µg, 360 µg, 365 µg, 370 µg, 375 µg, 380 µg, 385 µg, 390 µg, 395 µg, 400 µg, 405 µg, 410 µg, 415 µg, 420 µg, 425 µg, 430 µg, 435 µg, 440 µg, 445 µg, 450 µg, 455 µg, 460 µg, 465 µg, 470 µg, 475 µg, 480 µg, 485 µg, 490 µg, 495 µg, 500 µg, 505 µg, 510 µg, 515 µg, 520 µg, 525 µg, 530 µg, 535 µg, 540 µg, 545 µg, 550 µg, 555 µg, 560 µg, 565 µg, 570 µg, 575 µg, 580 µg, 585 µg, 590 µg, 595 µg, 600 µg, 605 µg, 610 µg, 615 µg, 620 µg, 625 µg, 630 µg, 635 µg, 640 µg, 645 µg, 650 µg, 655 µg, 660 µg, 665 µg, 670 µg, 675 µg, 680 µg, 685 µg, 690 µg, 695 µg, 700 µg, 705 µg, 710 µg, 715 µg, 720 µg, 725 µg, 730 µg, 735 µg, 740 µg, 745 µg, 750 µg, 755 µg, 760 µg, 765 µg, 770 µg, 775 µg, 780 µg, 785 µg, 790 µg, 795 µg, 800 µg, 805 µg, 810 µg, 815 µg, 820 µg, 825 µg, 830 µg, 835 µg, 840 µg, 845 µg, 850 µg, 855 µg, 860 µg, 865 µg, 870 µg, 875 µg, 880 µg, 885 µg, 890 µg, 895 µg, 900 µg, 905 µg, 910 µg, 915 µg, 920 µg, 925 µg, 930 µg, 935 µg, 940 µg, 945 µg, 950 µg, 955 µg, 960 µg, 965 µg, 970 µg, 975 µg, 980 µg, 985 µg, 990 µg, 995 µg, 1000 µg, 1005 µg, 1010 µg, 1015 µg, 1020 µg, 1025 µg, 1030 µg, 1035 µg, 1040 µg, 1045 µg, 1050 µg, 1055 µg, 1060 µg, 1065 µg, 1070 µg, 1075 µg, 1080 µg, 1085 µg, 1090 µg, 1095 µg, 1100 µg or similar. The suggested dosages per single dose specified above are not to be regarded as being limited to the numerical values actually stated, but are intended as dosages which are disclosed by way of example. Of course, dosages which may fluctuate about the abovementioned numerical values within a range of about +/−2.5 µg are also included in the values given above by way of example. In these dosage ranges, the active substances 1' and 2d may be present in the weight ratios given above.

For example, without restricting the scope of the invention thereto, the combinations of 1 and 2d according to the invention may contain a quantity of tiotropium 1' and $NK_1$-receptor antagonist 2d such that, for each single dose, 5 µg of 1' and 25 µg of 2d, 5 µg of 1' and 50 µg of 2d, 5 µg of 1' and 100 µg of 2d, 5 µg of 1' and 200 µg of 2d, 5 µg of 1' and 300 µg of 2d, 5 µg of 1' and 400 µg of 2d, 5 µg of 1' and 500 µg of 2d, 5 µg of 1' and 600 µg of 2d, 5 µg of 1' and 700 µg of 2d, 5 µg of 1' and 800 µg of 2d, 5 µg of 1' and 900 µg of 2d, 5 µg of 1' and 1000 µg of 2d, 10 µg of 1' and 25 µg of 2d, 10 µg of 1' and 50 µg of 2d, 10 µg of 1' and 100 µg of 2d, 10 µg of 1' and 200 µg of 2d, 10 µg of 1' and 300 µg of 2d, 10 µg of 1' and 400 µg of 2d, 10 µg of 1' and 500 µg of 2d, 10 µg of 1' and 600 µg of 2d, 10 µg of 1' and 700 µg of 2d, 10 µg of 1' and 800 µg of 2d, 10 µg of 1' and 900 µg of 2d, 10 µg of 1' and 1000 µg of 2d, 18 µg of 1' and 25 µg of 2d, 18 µg of 1' and 50 µg of 2d, 18 µg of 1' and 1000 µg of 2d, 18 µg of 1' and 200 µg of 2d, 18 µg of 1' and 300

μg of 2d, 18 μg of 1' and 400 μg of 2d, 18 μg of 1' and 500 μg of 2d, 18 μg of 1' and 600 μg of 2d, 18 μg of 1' and 700 μg of 2d, 18 μg of 1' and 800 μg of 2d, 18 μg of 1' and 900 μg of 2d, 18 μg of 1' and 1000 μg of 2d, 20 μg of 1' and 25 μg of 2d, 20 μg of 1' and 50 μg of 2d, 20 μg of 1' and 50 μg of 2d, 20 μg of 1' and 100 μg of 2d, 20 μg of 1' and 200 μg of 2d, 20 μg of 1' and 300 μg of 2d, 20 μg of 1' and 400 μg of 2d, 20 μg of 1' and 500 μg of 2d, 20 μg of 1' and 600 μg of 2d, 20 μg of 1' and 700 μg of 2d, 20 μg of 1' and 800 μg of 2d, 20 μg of 1' and 900 μg of 2d, 20 μg of 1' and 1000 μg of 2d, 36 μg of 1' and 25 μg of 2d, 36 μg of 1' and 50 μg of 2d, 36 μg of 1' and 10 μg of 2d, 36 μg of 1' and 200 μg of 2d, 36 μg of 1' and 300 μg of 2d, 36 μg of 1' and 400 μg of 2d, 36 μg of 1' and 500 μg of 2d, 36 μg of 1' and 600 μg of 2d, 36 μg of 1' and 700 μg of 2d, 36 μg of 1' and 800 μg of 2d, 36 μg of 1' and 900 μg of 2d, 36 μg of 1' and 1000 μg of 2d, 40 μg of 1' and 25 μg of 2d, 40 μg of 1' and 50 μg of 2d, 40 μg of 1' and 100 μg of 2d, 40 μg of 1' and 200 μg of 2d, 40l1 μg of 1' and 300 μg of 2d, 40 μg of 1' and 400 μg of 2d, 40 μg of 1' and 500 μg of 2d, 40l μg of 1' and 600 μg of 2d or 40 μg of 1' and 700 μg of 2d, 40 μg of 1' and 800 μg of 2d, 40 μg of 1' and 900 μg of 2d, 40 μg of 1' and 1000 μg of 2d are administered.

If the active substance combination in which 1 denotes tiotropium bromide is used as the preferred combination of 1 and 2d according to the invention, the quantities of active substance 1' and 2d administered per single dose mentioned by way of example correspond to the following quantities of 1 and 2d administered per single dose: 6 μg of 1 and 25 μg of 2d, 6 μg of 1 and 50 μg of 2d, 6 μg of 1 and 100 μg of 2d, 6 μg of 1 and 200 μg of 2d, 6 μg of 1 and 300 μg of 2d, 6 μg of 1 and 400 μg of 2d, 6 μg of 1 and 500 μg of 2d, 6 μg of 1 and 600 μg of 2d, 6 μg of 1 and 700 μg of 2d, 6 μg of 1 and 800 μg of 2d, 6 μg of 1 and 900 μg of 2d, 6 μg of 1 and 1000 μg of 2d, 12 μg of 1 and 25 μg of 2d, 12 μg of 1 and 50 μg of 2d, 12 μg of 1 and 100 μg of 2d, 12 μg of 1 and 200 μg of 2d, 12 μg of 1 and 300 μg of 2d, 12 μg of 1 and 400 μg of 2d, 12 μg of 1 and 500 μg of 2d, 12 μg of 1 and 600 μg of 2d, 12 μg of 1 and 700 μg of 2d, 12 μg of 1 and 800 μg of 2d, 12 μg of 1 and 900 μg of 2d, 12 μg of 1 and 1000 μg of 2d, 21.7 μg of 1 and 25 μg of 2d, 21.7 μg of 1 and 50 μg of 2d, 21.7 μg of 1 and 100 μg of 2d, 21.7 μg of 1 and 200 μg of 2d, 21.7 μg of 1 and 300 μg of 2d, 21.7 μg of 1 and 400 μg of 2d, 21.7 μg of 1 and 500 μg of 2d, 21.7 μg of 1 and 600 μg of 2d, 21.7 μg of 1 and 700 μg of 2d, 21.7 μg of 1 and 800 μg of 2d, 21.7 μg of 1 and 900 μg of 2d, 21.7 μg of 1 and 1000 μg of 2d, 24.1 μg of 1 and 25 μg of 2d, 24.1 μg of 1 and 50 μg of 2d, 24.1 μg of 1 and 100 μg of 2d, 24.1 μg of 1 and 200 μg of 2d, 24.1 μg of 1 and 300 μg of 2d, 24.1 μg of 1 and 400 μg of 2d, 24.1 μg of 1 and 500 μg of 2d, 24.1 μg of 1 and 600 μg of 2d, 24.1 μg of 1 and 700 μg of 2d, 24.1 μg of 1 and 800 μg of 2d, 24.1 μg of 1 and 900 μg of 2d, 24.1 μg of 1 and 1000 μg of 2d, 43.3 μg of 1 and 25 μg of 2d, 43.3 μg of 1 and 50 μg of 2d, 43.3 μg of 1 and 100 μg of 2d, 43.3 μg of 1 and 200 μg of 2d, 43.3 μg of 1 and 300 μg of 2d, 43.3 μg of 1 and 400 μg of 2d, 43.3 μg of 1 and 500 μg of 2d, 43.3 μg of 1 and 600 μg of 2d, 43.3 μg of 1 and 700 μg of 2d, 43.3 μg of 1 and 800 μg of 2d, 43.3 μg of 1 and 900 μg of 2d, 43.3 μg of 1 and 1000 μg of 2d, 48.1 μg of 1 and 25 μg of 2d, 48.1 μg of 1 and 50 μg of 2d, 48.1 μg of 1 and 100 μg of 2d, 48.1 μg of 1 and 200 μg of 2d, 48.1 μg of 1 and 300 μg of 2d, 48.1 μg of 1 and 400 μg of 2d, 48.1 μg of 1 and 500 μg of 2d, 48.1 μg of 1 and 600 μg of 2d, 48.1 μg of 1 and 700 μg of 2d, 48.1 μg of 1 and 800 μg of 2d, 48.1 μg of 1 and 900 μg of 2d, 48.1 μg of 1 and 1000 μg of 2d.

If the active substance combination in which 1 is tiotropium bromide monohydrate is used as the preferred combination of 1 and 2d according to the invention, the quantities of 1' and 2d administered per single dose specified by way of example hereinbefore correspond to the following quantities of 1 and 2d administered per single dose: 6.2 μg of 1 and 25 μg of 2d, 6.2 μg of 1 and 50 μg of 2d, 6.2 μg of 1 and 100 μg of 2d, 6.2 μg of 1 and 200 μg of 2d 6.2 μg of 1 and 300 μg of 2d, 6.2 μg of 1 and 400 μg of 2d, 6.2 μg of 1 and 500 μg of 2d 6.2 μg of 1 and 600 μg of 2d, 6.2 μg of 1 and 700 μg of 2d, 6.2 μg of 1 and 800 μg of 2d 6.2 μg of 1 and 900 μg of 2d, 6.2 μg of 1 and 100 μg of 2d, 12.5 μg of 1 and 25 μg of 2d, 12.5 μg of 1 and 50 μg of 2d, 12.5 μg of 1 and 100 μg of 2d, 12.5 μg of 1 and 200 μg of 2d, 12.5 μg of 1 and 300 μg of 2d, 12.5 μg of 1 and 400 μg of 2d, 12.5 μg of 1 and 500 μg of 2d, 12.5 μg of 1 and 600 μg of 2d, 12.5 μg of 1 and 700 μg of 2d, 12.5 μg of 1 and 800 μg of 2d, 12.5 μg of 1 and 900 μg of 2d, 12.5 μg of 1 and 1000 μg of 2d, 22.5 μg of 1 and 25 μg of 2d, 22.5 μg of 1 and 50 μg of 2d, 22.5 μg of 1 and 100 μg of 2d, 22.5 μg of 1 and 200 μg of 2d, 22.5 μg of 1 and 300 μg of 2d, 22.5 μg of 1 and 400 μg of 2d, 22.5 μg of 1 and 500 μg of 2d, 22.5 μg of 1 and 600 μg of 2d, 22.5 μg of 1 and 700 μg of 2d, 22.5 μg of 1 and 800 μg of 2d, 22.5 μg of 1 and 900 μg of 2d, 22.5 μg of 1 and 1000 μg of 2d, 25 μg of 1 and 25 μg of 2d, 25 μg of 1 and 50 μg of 2d, 25 μg of 1 and 100 μg of 2d, 25 μg of 1 and 200 μg of 2d, 25 μg of 1 and 300 μg of 2d, 25 μg of 1 and 400 μg of 2d, 25 μg of 1 and 500 μg of 2d, 25 μg of 1 and 600 μg of 2d, 25 μg of 1 and 700 μg of 2d, 25 μg of 1 and 800 μg of 2d, 25 μg of 1 and 900 μg of 2d, 25 μg of 1 and 1000 μg of 2d, 45 μg of 1 and 25 μg of 2d, 45 μg of 1 and 50 μg of 2d, 45 μg of 1 and 100 μg of 2d, 45 μg of 1 and 200 μg of 2d, 45 μg of 1 and 300 μg of 2d, 45 μg of 1 and 400 μg of 2d, 45 μg of 1 and 500 μg of 2d, 45 μg of 1 and 600 μg of 2d, 45 μg of 1 and 700 μg of 2d, 45 μg of 1 and 800 μg of 2d, 45 μg of 1 and 900 μg of 2d, 45 μg of 1 and 1000 μg of 2d, 50 μg of 1 and 25 μg of 2d, 50 μg of 1 and 50 μg of 2d, 50 μg of 1 and 100 μg of 2d, 50 μg of 1 and 200 μg of 2d, 50 μg of 1 and 300 μg of 2d, 50 μg of 1 and 400 μg of 2d 50 μg of 1 and 500 μg of 2d, 50 μg of 1 and 600 μg of 2d, 50 μg of 1 and 700 μg of 2d, 50 μg of 1 and 800 μg of 2d, 50 μg of 1 and 900 μg of 2d or 50 μg of 1 and 1000 μg of 2d.

As a rule, the pharmaceutical combinations according to the invention may contain compounds 1 and 2e in ratios by weight ranging from 1:300 to 50:1, preferably from 1:250 to 40:1. In the particularly preferred pharmaceutical combinations which contain ipratropium salt or tiotropium salt as compound 1 and a compound selected from among tezosentan, bosentan, enrasentan, sixtasentan, T-0201 and BMS-193884 as endothelin antagonist 2e, the weight ratios of 1 to 2e are most preferably in a range in which ipratropium or tiotropium 1' and 2e are present in proportions of 1:150 to 30:1, more preferably from 1:50 to 20:1.

For example, without restricting the scope of the invention thereto, preferred combinations of 1 and 2e according to the invention may contain ipratropium or tiotropium 1' and endothelin antagonist 2e in the following weight ratios: 1:80; 1:79; 1:78; 1:77; 1:76; 1:75; 1:74; 1:73; 1:72; 1:71; 1:70; 1:69; 1:68; 1:67; 1:66; 1:65; 1:64; 1:63 1:62; 1:61; 1:60; 1:59; 1:58; 1:57; 1:56; 1:55; 1:54; 1:53; 1:52; 1:51; 1:50; 1:49; 1:48; 1:47; 1:46; 1:45; 1:44; 1:43; 1:42; 1:41; 1:40; 1:39; 1:38; 1:37; 1:36; 1:35; 1:34; 1:33; 1:32; 1:31; 1:30; 1:29; 1:28; 1:27; 1:26; 1:25; 1:24; 1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1.

The pharmaceutical compositions according to the invention containing the combinations of 1 and 2e are normally administered so that 1 and 2e are present together in doses of 0.01 to 10,000 μg, preferably from 0.1 to 8000 μg, more preferably from 1 to 5000 μg, better still from 2.5 to 2500 μg, more preferably from 10 to 1500 μg per single dose. For example, combinations of 1 and 2e according to the invention contain a quantity of 1' and endothelin antagonist 2e such that the total dosage per single dose is about 200 μg, 210 μg, 220 μg, 230 μg, 240 μg, 250 μg, 260 μg, 270 μg, 280 μg, 290 μg, 300 μg, 310 μg, 320 μg, 330 μg, 340 μg, 350 μg, 360 μg, 370 μg, 380 μg, 390 μg, 400 μg, 410 μg, 420 μg, 430 μg, 440 μg, 450 μg, 460 μg, 470 μg, 480 μg, 490 μg, 500 μg, 510 μg, 520 μg, 530 μg, 540 μg, 550 μg, 560 μg, 570 μg, 580 μg, 590 μg, 600 μg, 610 μg, 620 μg, 630 μg, 640 μg, 650 μg, 660 μg, 670 μg, 680 μg, 690 μg, 700 μg, 710 μg, 720 μg, 730 μg, 740 μg, 750 μg, 760 μg, 770 μg, 780 μg, 790 μg, 800 μg, 810 μg, 820 μg, 830 μg, 840 μg, 850 μg, 860 μg, 870 μg, 880 μg, 890 μg, 900 μg, 910 μg, 920 μg, 930 μg, 940 μg, 950 μg, 960 μg, 970 μg, 980 μg, 990 μg, 1000 μg, 1010 μg, 1020 μg, 1030 μg, 1040 μg, 1050 μg, 1060 μg, 1070 μg, 1080 μg, 190 μg, 1100 μg, 1110 μg, 1120 μg, 1130 μg, 1140 μg, 1150 μg, 1160 μg, 1170 μg, 1180 μg, 1190 μg, 1200 μg, 1210 μg, 1220 μg, 1230 μg, 1240 μg, 1250 μg, 1260 μg, 1270 μg, 1280 μg, 1290 μg, 1300 μg, 1310 μg, 1320 μg, 1330 μg, 1340 μg, 1350 μg, 1360 μg, 1370 μg, 1380 μg, 1390 μg, 1400 μg, 1410 μg, 1420 μg, 1430 μg, 1440 μg, 1450 μg, 1460 μg, 1470 μg, 1480 μg, 1490 μg, 1500 μg, 1510 μg, 1520 μg, 1530 μg, 1540 μg, 1550 μg, 1560 μg, 1570 μg, 1580 μg, 1590 μg, 1600 μg, 1610 μg, 1620 μg, 1630 μg, 1640 μg, 1650 μg, 1660 μg, 1670 μg, 1680 μg, 1690 μg, 1700 μg, 1710 μg, 1720 μg, 1730 μg, 1740 μg, 1750 μg, 1760 μg, 1770 μg, 1780 μg, 1790 μg, 1800 μg, 1810 μg, 1820 μg, 1830 μg, 1840 μg, 1850 μg, 1860 μg, 1870 μg, 1880 μg, 1890 μg, 1900 μg, 1910 μg, 1920 μg, 1930 μg, 1940 μg, 1950 μg, 1960 μg, 1970 μg, 1980 μg, 1990 μg, 2000 μg or the like. The proposed dosages per single dose suggested above are not to be regarded as being restricted to the numerical values actually stated, but are intended only as examples of dosages. Of course, dosages which fluctuate around the above values in a range of about +/−5 μg are also covered by the values given above by way of example. In these dosage ranges the active substances 1' and 2e may be present in the weight ratios specified above.

For example, without restricting the scope of the invention thereto, the combinations of 1 and 2e according to the invention may contain a quantity of tiotropium 1' and endothelin antagonist 2e such that, in each individual dose, 5 μg of 1' and 100 μg of 2e, 5 μg of 1' and 200 μg of 2e, 5 μg of 1' and 300 μg of 2e, 5 μg of 1' and 400 μg of 2e, 5 μg of 1' and 500 μg of 2e, 5 μg of 1' and 600 μg of 2e, 5 μg of 1' and 700 μg of 2e, 5 μg of 1' and 800 μg of 2e, 5 μg of 1' and 900 μg of 2e, 5 μg of 1' and 10000 μg of 2e, 5 μg of 1' and 1500 μg of 2e, 5 μg of 1' and 2000 μg of 2e, 10 μg of 1' and 100 μg of 2e, 10 μg of 1' and 200 μg of 2e, 10 μg of 1' and 300 μg of 2e, 10 μg of 1' and 400 μg of 2e, 10 μg of 1' and 500 μg of 2e, 10 μg of 1' and 600 μg of 2e, 10 μg of 1' and 700 μg of 2e, 10 μg of 1' and 800 μg of 2e, 10 μg of 1' and 900 μg of 2e, 10 μg of 1' and 1000 μg of 2e, 10 μg of 1' and 1500 μg of 2e, 01 μg of 1' and 2000 μg of 2e, 18 μg of 1' and 100 μg of 2e, 18 μg of 1' and 200g of 2e, 18 μg of 1' and 300 μg of 2e, 18 μg of 1' and 4000 μg of 2e, 18 μg of 1' and 500 μg of 2e, 18 μg of 1' and 600 μg of 2e, 18 μg of 1' and 700 μg of 2e, 18 μg of 1' and 800 μg of 2e, 18 μg of 1' and 900 μg of 2e, 18 μg of 1' and 1000 μg of 2e, 18 μg of 1' and 1500 μg of 2e, 18 μg of 1' and 2000 μg of 2e, 20 μg of 1' and 100 μg of 2e, 20 μg of 1' and 200 μg of 2e, 20 μg of 1' and 300 μg of 2e, 20 μg of 1' and 400 μg of 2e, 20 μg of 1' and 500 μg of 2e, 20 μg of 1' and 600 μg of 2e, 20 μg of 1' and 700 μg of 2e, 20 μg of 1' and 800 μg of 2e, 20 μg of 1' and 900 μg of 2e, 20 μg of 1' and 1000 μg of 2e, 20 μg of 1' and 1500 μg of 2e, 20 μg of 1' and 2000 μg of 2e, 36 μg of 1' and 100 μg of 2e, 36 μg of 1' and 200 μg of 2e, 36 μg of 1' and 300 μg of 2e, 36 μg of 1' and 400 μg of 2e, 36 μg of 1' and 500 μg of 2e, 36 μg of 1' and 600 μg of 2e, 36 μg of 1' and 700 μg of 2e, 36 μg of 1' and 800 μg of 2e, 36 μg of 1' and 900 μg of 2e, 36 μg of 1' and 1000 μg of 2e, 36 μg of 1' and 1500 μg of 2e, 36 μg of 1' and 2000 μg of 2e, 40 μg of 1' and 100 μg of 2e, 40 μg of 1' and 200 μg of 2e, 40 μg of 1' and 300 μg of 2e, 40 μg of 1' and 400 μg of 2e, 40 μg of 1' and 500 μg of 2e or 40 μg of 1' and 600 μg of 2e, 40 μg of 1' and 700 μg of 2e, 40 μg of 1' and 800 μg of 2e, 40 μg of 1' and 900 μg of 2e, 40 μg of 1' and 1000 μg of 2e, 40 μg of 1' and 1500 μg of 2e, 40 μg of 1' and 2000 μg of 2e are administered.

If the active substance combination in which 1 denotes tiotropium bromide is used as the preferred combination of 1 and 2e according to the invention, the quantities of active substance 1' and 2e administered per single dose mentioned by way of example correspond to the following quantities of 1 and 2e administered per single dose: 6 μg of 1 and 100 μg of 2e, 6 μg of 1 and 200 μg of 2e, 6 μg of 1 and 300 μg of 2e, 61 μg of 1 and 400 μg of 2e, 6 μg of 1 and 500 μg of 2e, 6 μg of 1 and 600 μg of 2e, 6 μg of 1 and 700 μg of 2e, 6 μg of 1 and 800 μg of 2e, 6 μg of 1 and 900 μg of 2e, 6 μg of 1 and 1000 μg of 2e, 6 μg of 1 and 1500 μg of 2e, 6 μg of 1 and 2000 μg of 2e, 12 μg of 1 and 100 μg of 2e, 12 μg of 1 and 200 μg of 2e, 12 μg of 1 and 300 μg of 2e, 12 μg of 1 and 400 μg of 2e, 12 μg of 1 and 500 μg of 2e, 12 μg of 1 and 600 μg of 2e, 12 μg of 1 and 700 μg of 2e, 12 μg of 1 and 800 μg of 2e, 12 μg of 1 and 900 μg of 2e, 12 μg of 1 and 1000 μg of 2e, 12 μg of 1 and 1500 μg of 2e, 12 μg of 1 and 2000 μg of 2e, 21.7 μg of 1 and 100 μg of 2e, 21.7 μg of 1 and 200 μg of 2e, 21.7 μg of 1 and 300 μg of 2e, 21.7 μg of 1 and 400 μg of 2e, 21.7 μg of 1 and 500 μg of 2e, 21.7 μg of 1 and 600 μg of 2e, 21.7 μg of 1 and 700 μg of 2e, 21.7 μg of 1 and 800 μg of 2e, 21.7 μg of 1 and 900 μg of 2e, 21.7 μg of 1 and 1000 μg of 2e, 21.7 μg of 1 and 1500 μg of 2e, 21.7 μg of 1 and 2000 μg of 2e, 24.1 μg of 1 and 100 μg of 2e, 24.1 μg of 1 and 200 μg of 2e, 24.1 μg of 1 and 300 μg of 2e, 24.1 μg of 1 and 400 μg of 2e, 24.1 μg of 1 and 500 μg of 2e, 24.1 μg of 1 and 600 μg of 2e, 24.1 μg of 1 and 700 μg of 2e, 24.1 μg of 1 and 800 μg of 2e, 24.1 μg of 1 and 900 μg of 2e, 24.1 μg of 1 and 1000 μg of 2e, 24.1 μg of 1 and 1500 μg of 2e, 24.1 μg of 1 and 2000 μg of 2e, 43.3 μg of 1 and 100 μg of 2e, 43.3 μg of 1 and 200 μg of 2e, 43.3 μg of 1 and 300 μg of 2e, 43.3 μg of 1 and 400 μg of 2e, 43.3,1 μg of 1 and 500 μg of 2e, 43.3 μg of 1 and 600 μg of 2e, 43.3 μg of 1 and 700 μg of 2e, 43.3 μg of 1 and 800 μg of 2e, 43.3 μg of 1 and 900 μg of 2e, 43.3 μg of 1 and 1000 μg of 2e, 43.3 μg of 1 and 1500 μg of 2e, 43.3 μg of 1 and 2000 μg of 2e, 48.1 μg of 1 and 100 μg of 2e, 48.1 μg of 1 and 200 μg of 2e, 48.1 μg of 1 and 300 μg of 2e, 48.1 μg of 1 and 400 μg of 2e, 48.1 μg of 1 and 500 μg of 2e, 48.1 μg of 1 and 600 μg of 2e, 48.1 μg of 1 and 700 μg of 2e, 48.1 μg of 1 and 800 μg of 2e, 48.1 μg of 1 and 900 μg of 2e, 48.1 μg of 1 and 1000 μg of 2e, 48.1 μg of 1 and 1500 μg of 2e or 48.1 μg of 1 and 2000 μg of 2e.

If the active substance combination in which 1 is tiotropium bromide monohydrate is used as the preferred combination of 1 and 2e according to the invention, the quantities of 1' and 2e administered per single dose specified by way of example hereinbefore correspond to the following quantities of 1 and 2e administered per single dose: 6.2 μg of 1 and 100 μg of 2e, 6.2 μg of 1 and 200 μg of 2e, 6.2 μg of 1 and 300 μg of 2e, 6.2 μg of 1 and 400 μg of 2e, 6.2 μg of 1 and 500 μg of 2e, 6.2 μg of 1 and 600 μg of 2e, 6.2 μg of 1 and 700 μg of 2e, 6.2 μg of 1 and 800 μg of 2e, 6.2 μg of 1 and 900 μg of 2e, 6.2 μg of 1 and 1000 μg of 2e, 6.2 μg of 1 and 1500 μg of 2e, 6.2 μg of 1 and 2000 μg of 2e, 12.5 μg of 1 and 100 μg of 2e, 12.5 μg of 1 and 200 μg of 2e, 12.5 μg of 1 and 300 μg of 2e, 12.5 μg of 1 and 400 μg of 2e, 12.5 μg of 1 and 500 μg of 2e, 12.5 μg of 1 and 600 μg of 2e, 12.5 μg of 1 and 700 μg of 2e, 12.5 μg of 1 and 800 μg of 2e, 12.5 μg of 1 and 900 μg of 2e, 12.5 μg of 1 and 1000 μg of 2e, 12.5 μg of 1 and 1500 μg of 2e, 12.5

µg of 1 and 2000 µg of 2e, 22.5 µg of 1 and 100 µg of 2e, 22.5 µg of 1 and 200 µg of 2e, 22.5 µg of 1 and 300 µg of 2e, 22.5 µg of 1 and 400 µg of 2e, 22.5 µg of 1 and 500 µg of 2e, 22.5 µg of 1 and 600 µg of 2e, 22.5 µg of 1 and 700 µg of 2e, 22.5 µg of 1 and 800 µg of 2e, 22.5 µg of 1 and 900 µg of 2e, 22.5 µg of 1 and 1000 µg of 2e, 22.5 µg of 1 and 1500 µg of 2e, 22.5 µg of 1 and 2000 µg of 2e, 25 µg of 1 and 100 µg of 2e, 25 µg of 1 and 200 µg of 2e, 25 µg of 1 and 300 µg of 2e, 25 µg of 1 and 400 µg of 2e, 25 µg of 1 and 500 µg of 2e, 25 µg of 1 and 600 µg of 2e, 25 µg of 1 and 700 µg of 2e, 25 µg of 1 and 800 µg of 2e, 25 µg of 1 and 900 µg of 2e, 25 µg of 1 and 1000 µg of 2e, 25 µg of 1 and 1500 µg of 2e, 25 µg of 1 and 2000 µg of 2e, 45 µg of 1 and 100 µg of 2e, 45 µg of 1 and 200 µg of 2e, 45 µg of 1 and 300 µg of 2e, 45 µg of 1 and 400 µg of 2e, 45 µg of 1 and 500 µg of 2e, 45 µg of 1 and 600 µg of 2e, 45 µg of 1 and 700 µg of 2e, 45 µg of 1 and 800 µg of 2e, 45 µg of 1 and 900 µg of 2e, 45 µg of 1 and 1000 µg of 2e, 45 µg of 1 and 1500 µg of 2e, 45 µg of 1 and 2000 µg of 2e, 50 µg of 1 and 100 µg of 2e, 50 µg of 1 and 200 µg of 2e, 50 µg of 1 and 300 µg of 2e, 50 µg of 1 and 400 µg of 2e, 50 µg of 1 and 500 µg of 2e, 50 µg of 1 and 600 µg of 2e, 50 µg of 1 and 700 µg of 2e, 50 µg of 1 and 800 µg of 2e, 50 µg of 1 and 900 µg of 2e, 50 µg of 1 and 1000 µg of 2e, 50 µg of 1 and 1500 µg of 2e or 50 µg of 1 and 2000 µg of 2e.

As a rule, the pharmaceutical combinations according to the invention may contain compounds 1 and 2f in ratios by weight ranging from 1:300 to 50:1, preferably from 1:250 to 40:1. In the particularly preferred pharmaceutical combinations which contain tiotropium salt as compound 1, the weight ratios of 1 to 2f are most preferably in a range in which tiotropium 1' and 2f are present in proportions of 1:150 to 30:1, more preferably from 1:50 to 20:1.

For example, without restricting the scope of the invention thereto, preferred combinations of 1 and 2f according to the invention may contain tiotropium 1' and antihistamine 2f in the following weight ratios: 1:80; 1:79; 1:78; 1:77; 1:76; 1:75; 1:74; 1:73; 1:72; 1:71; 1:70; 1:69; 1:68; 1:67; 1:66; 1:65; 1:64; 1:63 1:62; 1:61; 1:60; 1:59; 1:58; 1:57; 1:56; 1:55; 1:54; 1:53; 1:52; 1:51; 1:50; 1:49; 1:48; 1:47; 1:46; 1:45; 1:44; 1:43; 1:42; 1:41; 1:40; 1:39; 1:38; 1:37; 1:36; 1:35; 1:34; 1:33; 1:32; 1:31; 1:30; 1:29; 1:28; 1:27; 1:26; 1:25; 1:24; 1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1; 11:1; 12:1; 13:1; 14:1; 15:1; 16:1; 17:1; 18:1; 19:1; and 20:1.

The pharmaceutical compositions according to the invention containing the combinations of 1 and 2f are normally administered so that 1 and 2f are present together in doses of 0.01 µg to 10,000 µg, preferably from 0.1 µg to 2000 µg, more preferably from 1 µg to 1500 µg, better still from 50 µg to 1200 µg per single dose. For example, combinations of 1 and 2f according to the invention contain a quantity of tiotropium 1' and antihistamine 2f such that the total dosage per single dose is 100 µg; 105 µg; 110 µg; 115 µg; 120 µg; 125 µg; 130 µg; 135 µg; 140 µg; 145 µg; 150 µg; 155 µg; 160 µg; 165 µg; 170 µg; 175 µg; 180 µg; 185 µg; 190 µg; 195 µg; 200 µg; 205 µg; 210 µg; 215 µg; 220 µg; 225 µg; 230 µg; 235 µg; 240 µg; 245 µg; 250 µg; 255 µg; 260 µg; 265 µg; 270 µg; 275 µg; 280 µg; 285 µg; 290 µg; 295 µg; 300 µg; 305 µg; 310 µg; 315 µg; 320 µg; 325 µg; 330 µg; 335 µg; 340 µg; 345 µg; 350 µg; 355 µg; 360 µg; 365 µg; 370 µg; 375 µg; 380 µg; 385 µg; 390 µg; 395 µg; 400 µg; 405 µg; 410 µg; 415 µg; 420 µg; 425 µg; 430 µg; 435 µg; 440 µg; 445 µg; 450 µg; 455 µg; 460 µg; 465 µg; 470 µg; 475 µg; 480 µg; 485 µg; 490 µg; 495 µg; 500 µg; 505 µg; 510 µg; 515 µg; 520 µg; 525 µg; 530 µg; 535 µg; 540 µg; 545 µg; 550 µg; 555 µg; 560 µg; 565 µg; 570 µg; 575 µg; 580 µg; 585 µg; 590 µg; 595 µg; 600 µg; 605 µg; 610 µg; 615 µg; 620 µg; 625 µg; 630 µg; 635 µg; 640 µg; 645 µg; 650 µg; 655 µg; 660 µg; 665 µg; 670 µg; 675 µg; 680 µg; 685 µg; 690 µg; 695 µg; 700 µg; 705 µg; 710 µg; 715 µg; 720 µg; 725 µg; 730 µg; 735 µg; 740 µg; 745 µg; 750 µg; 755 µg; 760 µg; 765 µg; 770 µg; 775 µg; 780 µg; 785 µg; 790 µg; 795 µg; 800 µg; 805 µg; 810 µg; 815 µg; 820 µg; 825 µg; 830 µg; 835 µg; 840 µg; 845 µg; 850 µg; 855 µg; 860 µg; 865 µg; 870 µg; 875 µg; 880 µg; 885 µg; 890 µg; 895 µg; 900 µg; 905 µg; 910 µg; 915 µg; 920 µg; 925 µg; 930 µg; 935 µg; 940 µg; 945 µg; 950 µg; 955 µg; 960 µg; 965 µg; 970 µg; 975 µg; 980 µg; 985 µg; 990 µg; 995 µg; 1000 µg; 1005 µg; 1010 µg; 1015 µg; 1020 µg; 1025 µg; 1030 µg; 1035 µg; 1040 µg; 1045 µg; 1050 µg; 1055 µg; 1060 µg; 1065 µg; 1070 µg; 1075 µg; 1080 µg; 1085 µg; 1090 µg; 1095 µg; 1100 µg, or the like. The proposed dosages per single dose suggested above are not to be regarded as being restricted to the numerical values actually stated, but are intended only as examples of dosages. Of course, dosages which fluctuate around the above values in a range of about ±2.5 µg are also covered by the values given above by way of example. In these dosage ranges the active substances 1' and 2f may be present in the weight ratios specified above. For example, without restricting the scope of the invention thereto, the combinations of 1 and 2f according to the invention may contain a quantity of tiotropium 1' and antihistamine 2f such that, in each individual dose, 5 µg of 1' and 25 µg of 2f; 5 µg of 1' and 50 µg of 2f; 5 µg of 1' and 100 µg of 2f; 5 µg of 1' and 200 µg of 2f; 5 µg of 1' and 300 µg of 2f; 5 µg of 1' and 400 µg of 2f; 5 µg of 1' and 500 µg of 2f; 5 µg of 1' and 600 µg of 2f; 5 µg of 1' and 700 µg of 2f; 5 µg of 1' and 800 µg of 2f; 5 µg of 1' and 900 µg of 2f; 5 µg of 1' and 1000 µg of 2f; 10 µg of 1' and 25 µg of 2f; 10 µg of 1' and 50 µg of 2f; 10 µg of 1' and 100 µg of 2f; 10 µg of 1' and 200 µg of 2f; 10 µg of 1' and 300 µg of 2f; 10 µg of 1' and 400 µg of 2f; 10 µg of 1' and 500 µg of 2f; 10 µg of 1' and 600 µg of 2f; 10 µg of 1' and 700 µg of 2f; 10 µg of 1' and 800 µg of 2f; 10 µg of 1' and 900 µg of 2f; 10 µg of 1' and 1000 µg of 2f; 18 µg of 1' and 25 µg of 2f; 18 µg of 1' and 50 µg of 2f; 18 µg of 1' and 100 µg of 2f; 118 µg of 1' and 200 µg of 2f; 18 µg of 1' and 300 µg of 2f; 18 µg of 1' and 400 µg of 2f; 18 µg of 1' and 500 µg of 2f; 18 µg of 1' and 600 µg of 2f; 18 µg of 1' and 700 µg of 2f; 18 µg of 1' and 800 µg of 2f; 18 µg of 1' and 900 µg of 2f; 18 µg of 1' and 1000 µg of 2f; 20 µg of 1' and 25 µg of 2f; 20 µg of 1' and 50 µg of 2f; 20 µg of 1' and 100 µg of 2f; 20 µg of 1' and 200 µg of 2f; 20 µg of 1' and 300 µg of 2f; 20 µg of 1' and 400 µg of 2f; 20 µg of 1' and 500 µg of 2f; 20 µg of 1' and 600 µg of 2f; 20 µg of 1' and 700 µg of 2f; 20 µg of 1' and 800 µg of 2f; 20 µg of 1' and 900 µg of 2f; 20 µg of 1' and 1000 µg of 2f; 36 µg of 1' and 25 µg of 2f; 36 µg of 1' and 50 µg of 2f; 36 µg of 1' and 100 µg of 2f; 36 µg of 1' and 200 µg of 2f; 36 µg of 1' and 300 µg of 2f; 36 µg of 1' and 400 µg of 2f; 36 µg of 1' and 500 µg of 2f; 36 µg of 1' and 600 µg of 2f; 36 µg of 1' and 700 µg of 2f; 36 µg of 1' and 800 µg of 2f; 36 µg of 1' and 900 µg of 2f; 36 µg of 1' and 1000 µg of 2f; 40 µg of 1' and 25 µg of 2f; 40 µg of 1' and 50 µg of 2f; 40 µg of 1' and 100 µg of 2f; 40 µg of 1' and 200 µg of 2f; 40 µg of 1' and 300 µg of 2f; 40 µg of 1' and 400 µg of 2f; 40 µg of 1' and 500 µg of 2f or 40 µg of 1' and 600 µg of 2f; 40 µg of 1' and 700 µg of 2f; 40 µg of 1' and 800 µg of 2f; 40 µg of 1' and 900 µg of 2f; 40 µg of 1' and 1000 µg of 2f are administered.

If the active substance combination in which 1 denotes tiotropium bromide is used as the preferred combination of 1 and 2f according to the invention, the quantities of active substance 1' and 2f administered per single dose mentioned by way of example correspond to the following quantities of 1 and 2f administered per single dose: 6 µg of 1 and 25 µg of 2f; 6 µg of 1 and 50 µg of 2f; 6 µg of 1 and 100 µg of 2f; 6 µg of 1 and 200 µg of 2f; 6 µg of 1 and 300 µg of 2f; 6 µg of 1 and 400 μg of 2f; 6 μg of 1 and 500 μg of 2f; 6 μg of 1 and 600 μg of 2f; 6 μg of 1 and 700 μg of 2f; 6 μg of 1 and 800 μg of 2f; 6 μg of 1 and 900 μg of 2f; 6 μg of 1 and 1000 μg of 2f; 12 μg of 1 and 25 μg of 2f; 12 μg of 1 and 50 μg of 2f; 12 μg of 1 and 100 μg of 2f; 12 μg of 1 and 200 μg of 2f; 12 μg of 1 and 300 μg of 2f; 12 μg of 1 and 400 μg of 2f; 12 μg of 1 and 500 μg of 2f; 12 μg of 1 and 600 μg of 2f; 12 μg of 1 and 700 μg of 2f 12 μg of 1 and 800 μg of 2f; 12 μg of 1 and 900 μg of 2f; 12 μg of 1 and 1000 μg of 2f; 21.7 μg of 1 and 25 μg of 2f; 21.7 μg of 1 and 50 μg of 2f; 21.7 μg of 1 and 100 μg of 2f; 21.7 μg of 1 and 200 μg of 2f; 21.7 μg of 1 and 300 μg of 2f; 21.7 μg of 1 and 400 μg of 2f 21.7 μg of 1 and 500 μg of 2f; 21.7 μg of 1 and 600 μg of 2f; 21.7 μg of 1 and 700 μg of 2f; 21.7 μg of 1 and 800 μg of 2f 21.7 μg of 1 and 900 μg of 2f; 21.7 μg of 1 and 1000 μg of 2f; 24.1 μg of 1 and 25 μg of 2f 24.1 μg of 1 and 50 μg of 2f; 24.1 μg of 1 and 100 μg of 2f; 24.1 μg of 1 and 200 μg of 2f 24.1 μg of 1 and 300 μg of 2f; 24.1 μg of 1 and 400 μg of 2f; 24.1 μg of 1 and 500 μg of 2f; 24.1 μg of 1 and 600 μg of 2f; 24.1 μg of 1 and 700 μg of 2f; 24.1 μg of 1 and 800 μg of 2f; 24.1 μg of 1 and 900 μg of 2f; 24.1 μg of 1 and 1000 μg of 2f; 43.3 μg of 1 and 25 μg of 2f; 43.3 μg of 1 and 50 μg of 2f; 43.3 μg of 1 and 100 μg of 2f; 43.3 μg of 1 and 200 μg of 2f; 43.3 μg of 1 and 300 μg of 2f; 43.3 μg of 1 and 400 μg of 2f; 43.3 μg of 1 and 500 μg of 2f; 43.3 μg of 1 and 600 μg of 2f; 43.3 μg of 1 and 700 μg of 2f; 43.3 μg of 1 and 800 μg of 2f; 43.3 μg of 1 and 900 μg of 2f; 43.3 μg of 1 and 1000 μg of 2f 48.1 μg of 1 and 25 μg of 2f; 48.1 μg of 1 and 50 μg of 2f 48.1 μg of 1 and 100 μg of 2f 48.1 μg of 1 and 200 μg of 2f; 48.1 μg of 1 and 300 μg of 2f 48.1 μg of 1 and 400 μg of 2f; 48.1 μg of 1 and 500 μg of 2f 48.1 μg of 1 and 600 μg of 2f; 48.1 μg of 1 and 700 μg of 2f; 48.1 μg of 1 and 800 μg of 2f; 48.1 μg of 1 and 900 μg of 2f or 48.1 μg of 1 and 1000 μg of 2f.

If the active substance combination in which 1 is tiotropium bromide monohydrate is used as the preferred combination of 1 and 2f according to the invention, the quantities of 1' and 2f administered per single dose specified by way of example hereinbefore correspond to the following quantities of 1 and 2f administered per single dose: 6.2 μg 1 and 25 μg 2f; 6.2 μg 1 and 50 μg 2f; 6.2 μg 1 and 100 μg 2f; 6.2 μg 1 and 200 μg 2f; 6.2 μg 1 and 300 μg 2f; 6.2 μg 1 and 400 μg 2f; 6.2 μg 1 and 500 μg 2f; 6.2 μg 1 and 600 μg 2f; 6.2 μg 1 and 700 μg 2f; 6.2 μg 1 and 800 μg 2f; 6.2 μg 1 and 900 μg 2f; 6.2 μg 1 and 1000 μg 2f; 12.5 μg 1 and 25 μg 2f; 12.5 μg 1 and 50 μg 2f; 12.5 μg 1 and 100 μg 2f; 12.5 μg 1 and 200 μg 2f; 12.5 μg 1 and 300 μg 2f; 12.5 μg 1 and 400 μg 2f; 12.5 μg 1 and 500 μg 2f; 12.5 μg 1 and 600 μg 2f; 12.5 μg 1 and 700 μg 2f; 12.5 μg 1 and 800 μg 2f; 12.5 μg 1 and 900 μg 2f; 12.5 μg 1 and 1000 μg 2f; 22.5 μg 1 and 25 μg 2f; 22.5 μg 1 and 50 μg 2f; 22.5 μg 1 and 100 μg 2f; 22.5 μg 1 and 200 μg 2f; 22.5 μg 1 and 300 μg 2f; 22.5 μg 1 and 400 μg 2f; 22.5 μg 1 and 500 μg 2f; 22.5 μg 1 and 600 μg 2f; 22.5 μg 1 and 700 μg 2f; 22.5 μg 1 and 800 μg 2f; 22.5 μg 1 and 900 μg 2f; 22.5 μg 1 and 1000 μg 2f; 25 μg 1 and 25 μg 2f; 25 μg 1 and 50 μg 2f; 25 μg 1 and 100 μg 2f; 25 μg 1 and 200 μg 2f; 25 μg 1 and 300 μg 2f; 25 μg 1 and 400 μg 2f; 25 μg 1 and 500 μg 2f; 25 μg 1 and 600 μg 2f; 25 μg 1 and 700 μg 2f; 25 μg 1 and 800 μg 2f; 25 μg 1 and 900 μg 2f; 25 μg 1 and 1000 μg 2f; 45 μg 1 and 25 μg 2f; 45 μg 1 and 50 μg 2f; 45 μg 1 and 100 μg 2f; 45 μg 1 and 200 μg 2f; 45 μg 1 and 300 μg 2f; 45 μg 1 and 400 μg 2f; 45 μg 1 and 500 μg 2f; 45 μg 1 and 600 μg 2f; 45 μg 1 and 700 μg 2f; 45 μg 1 and 800 μg 2f; 45 μg 1 and 900 μg 2f; 45 μg 1 and 1000 μg 2f; 50 μg 1 and 25 g 2f; 50 μg 1 and 50 μg 2f; 50 μg 1 and 100 μg 2f; 50 μg 1 and 200 μg 2f; 50 μg 1 and 300 μg 2f; 50 μg 1 and 400 μg 2f; 50 μg 1 and 500 μg 2f; 50 μg 1 and 600 μg 2f; 50 μg 1 and 700 μg 2f; 50 μg 1 and 800 μg 2f; 50 μg 1 and 900 μg 2f or 50 μg 1 and 1000 μg 2f.

As a rule, the pharmaceutical combinations according to the invention may contain compounds 1 and 2g in ratios by weight ranging from 1:800 to 20:1, preferably from 1:600 to 10:1.

In the particularly preferred pharmaceutical combinations which contain tiotropium salt as compound 1 and a compound selected from among 4-[(3-chloro-4-fluoro-phenyl)amino]-7-[4-((R)-6-methyl-2-oxo-morpholin-4-yl)-butyloxy]-6-[(vinylcarbonyl)amino]-quinazoline, 4-[(3-chloro-4-fluoro-phenyl)amino]-7-[4-((S)-6-methyl-2-oxo-morpholin-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline, 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, 4-[(3-chloro-4-fluorophenyl)amino]-6-[(4-{N-[2-(ethoxycarbonyl)-ethyl]-N-[(ethoxycarbonyl)methyl]amino}-1-oxo-2-buten-1-yl)amino]-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopropylmethoxy-quinazoline and 4-[(3-chloro-4-fluorophenyl)amino]-6-[3-(morpholin-4-yl)-propyloxy]-7-methoxy-quinazoline as EGFR kinase inhibitors 29, the weight ratios of 1 to 2g are preferably in a range wherein tiotropium 1' and 22 is present in proportions ranging from 1:500 to 5:1, more preferably from 1:450 to 1:1, most preferably from 1:400 to 1:100.

For example and without restricting the scope of the invention thereto, preferred combinations of 1 and 2g according to the invention may contain tiotropium 1' and EGFR kinase inhibitors 2g in the following weight ratios: 1:200, 1:205, 1:210, 1:215, 1:220, 1:225, 1:230, 1:235, 1:240, 1:245, 1:250, 1:255, 1:260, 1:265, 1:270, 1:275, 1:280, 1:285, 1:290, 1:295, 1:300, 1:305, 1:310, 1:315, 1:320, 1:325, 1:330, 1:335, 1:340, 1:345, 1:350.

The pharmaceutical compositions according to the invention containing the combinations of 1 and 2g are normally used so that 1 and 2g may be present together in doses from 1000 to 100000 μg, preferably from 1500 to 50000 μg, more preferably from 2000 to 10000 μg, even more preferably from 2500 to 7500 μg per single dose. For example combinations of 1 and 2g according to the invention contain an amount of tiotropium 1' and EGFR kinase inhibitors 22 such that the total dosage per single dose is 2500 μg, 2550 μg, 2600 μg, 2650 μg, 2700 μg, 2750 μg, 2800 μg, 2850 μg, 2900 μg, 2950 μg, 3000 μg, 3050 μg, 3100 μg, 3150 μg, 3200 μg, 3250 μg, 3300 μg, 3350 μg, 3400 μg, 3450 μg, 3500 μg, 3550 μg, 3600 μg, 3650 μg, 3700 μg, 3750 μg, 3800 μg, 3850 μg, 3900 μg, 3950 μg, 4000 μg, 4050 μg, 4100 μg, 4150 μg, 4200 μg, 4250 μg, 4300 μg, 4350 μg, 4400 μg, 4450 μg, 4500 μg, 4550 μg, 4600 μg, 4650 μg, 4700 μg, 4750 μg, 4800 μg, 4850 μg, 4900 μg, 4950 μg, 5000 μg, 5050 μg, 5100 μg, 5150 μg, 5200 μg, 5250 μg, 5300 μg, 5350 μg, 5400 μg, 5450 μg, 5500 μg, 5550 μg, 5600 μg, 5650 μg, 5700 μg, 5750 μg, 5800 μg, 5850 μg, 5900 μg, 5950 μg, 6000 μg, 6050 μg, 6100 μg, 6150 μg, 6200 μg, 6250 μg, 6300 μg, 6350 μg, 6400 μg, 6450 μg, 6500 μg, 6550 μg, 6600 μg, 6650 μg, 6700 μg, 6750 μg, 6800 μg, 6850 μg, 6900 μg, 6950 μg, 7000 μg, 7050 μg, 7100 μg, 7150 μg, 7200 μg, 7250 μg, 7300 μg, 7350 μg, 7400 μg, 7450 μg, 7500 μg or the like. These proposed dosages per single dose are not to be regarded as being restricted to the numerical values explicitly mentioned but are merely disclosed by way of example. Obviously, dosages which fluctuate around these values within a range of about +/−25 μg are also covered by the values mentioned by way of example. In these dosage ranges the active substances 1' and 2g may be present in the weight ratios described above.

For example and without restricting the scope of the invention thereto, the combinations of 1 and 2g according to the invention may contain an amount of tiotropium 1' and EGFR kinase inhibitor 2g such that 5 μg of 1' and 2500 μg of 2g, 5 μg of 1' and 3000 μg of 1t, 5 μg of 1' and 3500 μg of 2g, 5 μg of 1' and 4000 μg of 2g, 5 μg of 1' and 4500 μg of 2g, 5 μg of 1' and 5000 μg of 2g, 5 μg of 1' and 5500 μg of 2g, 5 μg of 1' and 6000 μg of 2g, 5 μg of 1' and 6500 μg of 2g, 5μg of 1' and 7000 μg of 2g, 10 μg of 1' and 2500 μg of 2g, 10 μg of 1' and 3000 μg of 2g, 10 μg of 1' and 3500 μg of 2g, 10 μg of 1' and 4000 μg of 2g, 10 μg of 1' and 4500 μg of 2g, 10 μg of 1' and 5000 μg of 2g, 10 μg of 1' and 5500 μg of 2g, 10 μg of 1' and 6000 μg of 2g, 10 μg of 1' and 6500 μg of 2g, 10 μg of 1' and 7000 μg of 2g, 18 μg of 1' and 2500 μg of 2g, 18 μg of 1' and 3000 μg of 2g, 18 μg of 1' and 3500 μg of 2g, 18 μg of 1' and 4000 μg of 2g, 18 μg of 1' and 4500 μg of 2g, 18 μg of 1' and 5000 μg of 2g, 18 μg of 1' and 5500 μg of 2g, 18 μg of 1' and 6000 μg of 2g, 18 μg of 1' and 6500 μg of 2g, 18 μg of 1' and 7000 μg of 2g, 20 μg of 1' and 2500 μg of 2g, 20 μg of 1' and 3000 μg of 2g, 20 μg of 1' and 3500 μg of 2g, 20 μg of 1' and 4000 μg of 2g, 20 μg of 1' and 4500 μg of 2g, 20 μg of 1' and 5000 μg of 2g, 20 μg of 1' and 5500 μg of 2g, 20 μg of 1' and 6000 μg of 2g, 20 μg of 1' and 6500 μg of 2g, 20 μg of 1' and 7000 μg of 2g, 36 μg of 1' and 2500 μg of 2g, 36 μg of 1' and 3000 μg of 2g, 36 μg of 1' and 3500 μg of 2g, 36 μg of 1' and 4000 μg of 2g, 36 μg of 1' and 4500 μg of 2g, 36 μg of 1' and 5000 μg of 2g, 36 μg of 1' and 5500 μg of 2g, 36 μg of 1' and 6000 μg of 2g, 36 μg of 1' and 6500 μg of 2g, 36 μg of 1' and 7000 μg of 2g, 40 μg of 1' and 2500 μg of 2g, 40 μg of 1' and 3000 μg of 2g, 40 μg of 1' and 3500 μg of 2g, 40 μg of 1' and 4000 μg of 2g, 40 μg of 1' and 4500 μg of 2g, 40 μg of 1' and 5000 μg of 2g, 40 μg of 1' and 5500 μg of 2g or 40 μg of 1' and 6000 μg of 2g, 40 μg of 1' and 6500 μg of 2g, 40 μg of 1' and 7000 μg of 2g are administered per single dose.

If the active substance combination wherein 1 denotes tiotropium bromide is used as the preferred combination of 1 and 2g according to the invention, the quantities of active substances 1' and 2g administered per single dose as specified by way of example correspond to the following quantities of 1 and 2g administered: 6 μg of 1 and 2500 μg of 2g, 6 μg of 1 and 3000 μg of 2g, 6 μg of 1 and 3500 μg of 2g, 6 μg of 1 and 4000 μg of 2g, 6 μg of 1 and 4500 μg of 2g, 6 μg of 1 and 5000 μg of 2g, 6 μg of 1 and 5500 μg of 2g, 6 μg of 1 and 6000 μg of 2g, 6 μg of 1 and 6500 μg of 2g, 61 μg of 1 and 7000 μg of 2g, 12 μg of 1 and 2500 μg of 2g, 12 μg of 1 and 3000 μg of 2g, 12 μg of 1 and 3500 μg of 1t, 12 μg of 1 and 4000 μg of 2g, 12 μg of 1 and 4500 μg of 2g, 12 μg of 1 and 5000 μg of 2g, 12 μg of 1 and 5500 μg of 2g, 12 μg of 1 and 6000 μg of 2g, 12 μg of 1 and 6500 μg of 2g, 12 μg of 1 and 7000 μg of 2g, 1.7 μg of 1 and 2500 μg of 2g, 21.7 μg of 1 and 3000 μg of 2g, 1.7 μg of 1 and 3500 μg of 2g, 21.7 μg of 1 and 4000 μg of 2g, 21.7 μg of 1 and 4500 μg of 2g, 21.7 μg of 1 and 5000 μg of 2g, 21.7 μg of 1 and 5500 μg of 2g, 21.7 μg of 1 and 6000 μg of 2g, 1.7 μg of 1 and 6500 μg of 2g, 21.7 μg of 1 and 7000 μg of 2g, 24.1 μg of 1 and 2500 μg of 2g, 24.1 μg of 1 and 3000 μg of 2g, 24.1 μg of 1 and 3500 μg of 2g, 24.1 μg of 1 and 4000 μg of 2g, 24.1 μg of 1 and 4500 μg of 2g, 24.1 μg of 1 and 5000 μg of 2g, 24.1 μg of 1 and 5500 μg of 2g, 24.1 μg of 1 and 6000 μg of 2g, 24.1 μg of 1 and 6500 μg of 2g, 24.1 μg of 1 and 7000 μg of 2g, 43.3 μg of 1 and 2500 μg of 2g, 43.3 μg of 1 and 3000 μg of 2g, 43.3 μg of 1 and 3500 μg of 2g, 43.3 μg of 1 and 4000 μg of 2g, 43.3 μg of 1 and 4500 μg of 2g, 43.3 μg of 1 and 5000 μg of 2g, 43.3 μg of 1 and 5500 μg of 2g, 43.3 μg of 1 and 6000 μg of 2g, 43.3 μg of 1 and 6500 μg of 2g, 43.3 μg of 1 and 7000 μg of 2g, 48.1 μg of 1 and 2500 μg of 2g, 48.1 μg of 1 and 3000 μg of 2g, 48.1 μg of 1 and 3500 μg of 2g, 48.1 μg of 1 and 4000 μg of 2g, 48.1 μg of 1 and 4500 μg of 2g, 48.1 μg of 1 and 5000 μg of 2g, 48.11 μg of 1 and 5500 μg of 2g, 48.1 μg of 1 and 6000 μg of 2g, 48.1 μg of 1 and 6500 μg of 2g or 48.11 μg of 1 and 7000 μg of 2g.

If the active substance combination wherein 1 denotes tiotropium bromide monohydrate is used as the preferred combination of 1 and 2g according to the invention, the quantities of active substances 1' and 2g administered per single dose as mentioned above by way of example correspond to the following quantities of 1 and 2g administered per single dose: 6.2 μg of 1 and 2500 μg of 2g, 6.2 μg of 1 and 3000 μg of 2g, 6.2 μg of 1 and 3500 μg of 2g, 6.2 μg of 1 and 4000 μg of 2g, 6.2 μg of 1 and 4500 μg of 2g, 6.2 μg of 1 and 5000 μg of 2g, 6.2 μg of 1 and 5500 μg of 2g, 6.2 μg of 1 and 6000 μg of 2g, 6.2 μg of 1 and 6500 μg of 2g, 6.2 μg of 1 and 7000 μg of 2g, 12.5 μg of 1 and 2500 μg of 2g, 12.5 μg of 1 and 3000 μg of 2g, 12.5 μg of 1 and 3500 μg of 2g, 12.5 μg of 1 and 4000 μg of 2g, 12.5 μg of 1 and 4500 μg of 2g, 12.5 μg of 1 and 5000 μg of 2g, 12.5 μg of 1 and 5500 μg of 2g, 12.5 μg of 1 and 6000 μg of 2g, 2.5 μg of 1 and 6500 μg of 2g, 12.5 μg of 1 and 7000 μg of 2g, 22.5 μg of 1 and 2500 μg of 2g, 2.5 μg of 1 and 3000 μg of 2g, 2.5 μg of 1 and 3500 μg of 2g, 2.5 μg of 1 and 4000 μg of 2g, 22.5 μg of 1 and 4500 μg of 2g, 22.5 μg of 1 and 5000 μg of 2g, 22.5 μg of 1 and 5500 μg of 2g, 22.5 μg of 1 and 6000 μg of 2g, 2.5 μg of 1 and 6500 μg of 2g, 22.5 μg of 1 and 7000 μg of 2g, 5 μg of 1 and 2500 μg of 2g, 25 μg of 1 and 3000 μg of 2g, 25 μg of 1 and 3500 μg of 2g, 25 μg of 1 and 4000 μg of 2g, 25 μg of 1 and 4500 μg of 2g, 25 μg of 1 and 5000 μg of 2g, 25 μg of 1 and 5500 μg of 2g, 5 μg of 1 and 6000 μg of 2g, 25 μg of 1 and 6500 μg of 2g, 5 μg of 1 and 7000 μg of 2g, 45 μg of 1 and 2500 μg of 2g, 45 μg of 1 and 3000 μg of 2g, 5 μg of 1 and 3500 μg of 2g, 5 μg of 1 and 4000 μg of 2g, 45 μg of 1 and 4500 μg of 2g, 45 μg of 1 and 5000 μg of 2g, 5 μg of 1 and 5500 μg of 2g, 45 μg of 1 and 6000 μg of 2g, 45 μg of 1 and 6500 μg of 2g, 45 μg of 1 and 7000 μg of 2g, 50 μg of 1 and 2500 μg of 2g, 50 μg of 1 and 3000 μg of 2g, 50 μg of 1 and 3500 μg of 2g, 50 μg of 1 and 4000 μg of 2g, 50 μg of 1 and 4500 μg of 2g, 50 μg of 1 and 5000 μg of 2g, 50 μg of 1 and 5500 μg of 2g, 50 μg of 1 and 6000 μg of 2g, 50 μg of 1 and 6500 μg of 2 or 50 μg of 1 and 7000 μg of 2g. hier weiter The active substance combinations of 1 and 2 according to the invention are preferably administered by inhalation. For this purpose, ingredients 1 and 2 have to be made available in forms suitable for inhalation. Inhalable preparations include inhalable powders, propellant-containing metering aerosols or propellant-free inhalable solutions. Inhalable powders according to the invention containing the combination of active substances 1 and 2 may consist of the active substances on their own or of a mixture of the active substances with physiologically acceptable excipients. Within the scope of the present invention, the term propellant-free inhalable solutions also includes concentrates or sterile inhalable solutions ready for use. The preparations according to the invention may contain the combination of active substances 1 and 2 either together in one formulation or in two separate formulations. These formulations which may be used within the scope of the present invention are described in more detail in the next part of the specification.

A. Inhalable Powder Containing the Combinations of Active Substances 1 and 2 According to the Invention The inhalable powders according to the invention may contain 1 and 2 either on their own or in admixture with suitable physiologically acceptable excipients.

If the active substances 1 and 2 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, maltose), oligo- and polysaccharides (e.g., dextran), polyalcohols (e.g., sorbitol, mannitol, or xylitol), salts (e.g., sodium chloride or calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 μm and 150 μm, most preferably between 15 μm and 80 μm. It may sometimes seem appropriate to add finer excipient fractions with an average particle size of 1 μm to 9 μm to the excipient mentioned above. These finer excipients are also selected from the group of possible excipients listed hereinbefore. Finally, in order to prepare the inhalable powders according to the invention, micronised active substance 1 and 2, preferably with an average particle size of 0.5 to 10 μm, more preferably from 1 to 5 μm, is added to the excipient mixture. Processes for producing the inhalable powders according to the invention by grinding and micronizing and by finally mixing the ingredients together are known from the prior art. The inhalable powders according to the invention may be prepared and administered either in the form of a single powder mixture which contains both 1 and 2 or in the form of separate inhalable powders which contain only 1 or 2.

The inhalable powders according to the invention may be administered using inhalers known from the prior art. Inhalable powders according to the invention which contain a physiologically acceptable excipient in addition to 1 and 2 may be administered, for example, by means of inhalers which deliver a single dose from a supply using a measuring chamber as described in U.S. Pat. No. 4,570,630, or by other means as described in DE 36 25 685 A. Preferably, the inhalable powders according to the invention which contain physiologically acceptable excipient in addition to 1 and 2 are packed into capsules (to produce so-called inhalettes) which are used in inhalers as described, for example, in WO 94/28958.

A particularly preferred inhaler for using the pharmaceutical combination according to the invention in inhalettes is shown in FIG. 1.

This inhaler (Handihaler®) for inhaling powdered pharmaceutical compositions from capsules is characterized by a housing 1 containing two windows 2, a deck 3 in which there are air inlet portions and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut.

If the inhalable powders according to the invention are packed into capsules (inhalers) for the preferred use described above, the quantities packed into each capsule should be 1 mg to 30 mg, preferably 3 mg to 20 mg, more particularly 5 mg to 10 mg of inhalable powder per capsule. These capsules contain, according to the invention, either together or separately, the doses of 1' and 2 mentioned hereinbefore for each single dose.

B. Propellant Gas-Driven Inhalation Aerosols Containing the Combinations of Active Substances 1 and 2

Inhalation aerosols containing propellant gas according to the invention may contain substances 1 and 2 dissolved in the propellant gas or in dispersed form. 1 and 2 may be present in separate formulations or in a single preparation, in which 1 and 2 are either both dissolved, both dispersed or only one component is dissolved and the other is dispersed.

The propellant gases which may be used to prepare the inhalation aerosols according to the invention are known from the prior art. Suitable propellant gases are selected from among hydrocarbons such as n-propane, n-butane, or isobutane and halohydrocarbons such as fluorinated derivatives of methane, ethane, propane, butane, cyclopropane, or cyclobutane. The propellant gases mentioned above may be used on their own or in mixtures thereof. Particularly preferred propellant gases are halogenated alkane derivatives selected from TG134a and TG227. Of the halogenated hydrocarbons mentioned above, TG134a (1,1,1,2-tetrafluoroethane) and TG227 (1,1,1,2,3,3,3-heptafluoropropane) and mixtures thereof are preferred according to the invention.

The propellant-driven inhalation aerosols according to the invention may also contain other ingredients such as cosolvents, stabilizers, surfactants, antioxidants, lubricants, and pH adjusters. All these ingredients are known in the art.

The inhalation aerosols containing propellant gas according to the invention may contain up to 5 wt. % of active substance 1 and/or 2. Aerosols according to the invention contain, for example, 0.002 wt. % to 5 wt. %, 0.01 wt. % to 3 wt. %, 0.015 wt. % to 2 wt. %, 0.1 wt. % to 2 wt. %, 0.5 wt. % to 2 wt. %, or 0.5 wt. % to 1 wt. % of active substance 1 and/or 2.

If the active substances 1 and/or 2 are present in dispersed form, the particles of active substance preferably have an average particle size of up to 10 μm, preferably from 0.1 μm to 5 μm, more preferably from 1 μm to 5 μm.

The propellant-driven inhalation aerosols according to the invention mentioned above may be administered using inhalers known in the art (MDIs: metered dose inhalers). Accordingly, in another aspect, the present invention relates to pharmaceutical compositions in the form of propellant-driven aerosols as hereinbefore described combined with one or more inhalers suitable for administering these aerosols. In addition, the present invention relates to inhalers which are characterized in that they contain the propellant gas-containing aerosols described above according to the invention. The present invention also relates to cartridges which are fitted with a suitable valve and can be used in a suitable inhaler and which contain one of the above-mentioned propellant gas-containing inhalation aerosols according to the invention. Suitable cartridges and methods of filling these cartridges with the inhalable aerosols containing propellant gas according to the invention are known from the prior art.

C. Propellant-Free Inhalable Solutions or Suspensions Containing the Combinations of Active Substances 1 and 2 According to the Invention It is particularly preferred to use the active substance combination according to the invention in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1 and 2, separately or together, are adjusted to a pH of 2 to 7, preferably 2 to 5, using suitable acids. The pH may be adjusted using acids selected from inorganic or organic acids. Examples of suitable inorganic acids include hydrochloric acid, hydrobromic acid, nitric acid, sulfuric acid and/or phosphoric acid. Examples of particularly suitable organic acids include ascorbic acid, citric acid, malic acid, tartaric acid, maleic acid, succinic acid, fumaric acid, acetic acid, formic acid, and/or propionic acid, etc. Preferred inorganic acids are hydrochloric and sulfuric acids. It is also possible to use the acids which have already formed an acid addition salt with one of the active substances. Of the organic acids, ascorbic acid, fumaric acid, and citric acid are preferred. If desired, mixtures of the above acids may be used, particularly in the case of acids which have other properties in addition to their acidifying qualities, e.g., as flavorings, antioxidants, or complexing agents, such as citric acid or ascorbic acid, for example. According to the invention, it is particularly preferred to use hydrochloric acid to adjust the pH.

According to the invention, the addition of edetic acid (EDTA) or one of the known salts thereof, sodium edetate, as stabilizer or complexing agent, is unnecessary in the present formulation. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions according to the invention. Preferred co-solvents are those which contain hydroxyl groups or other polar groups, e.g., alcohols, particularly isopropyl alcohol, glycols—particularly propylene glycol, polyethylene glycol, polypropylene glycol, glycol ether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants, and/or preservatives which guarantee or prolong the shelf life of the finished pharmaceutical formulation, flavorings, vitamins, and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those which are known in the art, particularly cetyl pyridinium chloride, benzalkonium chloride, or benzoic acid, or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the combination of active substances 1 and 2, only benzalkonium chloride and sodium edetate. In another preferred embodiment, no sodium edetate is present.

The propellant-free inhalable solutions according to the invention are administered in particular using inhalers of the kind which are capable of nebulizing a small amount of a liquid formulation in the therapeutic dose within a few seconds to produce an aerosol suitable for therapeutic inhalation. Within the scope of the present invention, preferred inhalers are those in which a quantity of less than 100 µL, preferably less than 50 mL, more preferably between 10 µL and 30 µL of active substance solution can be nebulized in preferably one spray action to form an aerosol with an average particle size of less than 20 µm, preferably less than 10 µm, in such a way that the inhalable part of the aerosol corresponds to the therapeutically effective quantity.

An apparatus of this kind for propellant-free delivery of a metered quantity of a liquid pharmaceutical composition for inhalation is described for example in International Patent Application WO 91/14468 and also in WO 97/12687 (cf. in particular FIGS. 6a and 6b), both of which are incorporated herein by reference in their entireties. The nebulizers (devices) described therein are known by the name Respimat®.

This nebulizer (Respimat®) can advantageously be used to produce the inhalable aerosols according to the invention containing the combination of active substances 1 and 2. Because of its cylindrical shape and handy size of less than 9 cm to 15 cm long and 2 cm to 4 cm wide, this device can be carried at all times by the patient. The nebulizer sprays a defined volume of pharmaceutical formulation using high pressures through small nozzles so as to produce inhalable aerosols.

The preferred atomizer essentially consists of an upper housing part, a pump housing, a nozzle, a locking mechanism, a spring housing, a spring and a storage container, characterized by
  a pump housing which is secured in the upper housing part and which comprises at one end a nozzle body with the nozzle or nozzle arrangement,
  a hollow plunger with valve body,
  a power takeoff flange in which the hollow plunger is secured and which is located in the upper housing part,
  a locking mechanism situated in the upper housing part,
  a spring housing with the spring contained therein, which is rotatably mounted on the upper housing part by means of a rotary bearing,
  a lower housing part which is fitted onto the spring housing in the axial direction.

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 MPa to 60 MPa (about 50 bar to 600 bar), preferably 10 MPa to 60 MPa (about 100 bar to 600 bar) on the fluid, the measured amount of active substance solution, at its high pressure end at the moment when the spring is actuated. Volumes of 10 to 50 microliters are preferred, while volumes of 10 to 20 microliters are particularly preferred and a volume of 15 microliters per spray is most particularly preferred. The valve body is preferably mounted at the end of the hollow plunger facing the valve body.

The nozzle in the nozzle body is preferably microstructured, i.e., produced by microtechnology. Microstructured valve bodies are disclosed for example in WO 94/07607;

reference is hereby made to the contents of this specification, particularly FIG. 1 therein and the associated description. WO 94/07607 is incorporated herein by reference in its entirety.

The valve body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20° to 160° to one another, preferably 60° to 150°, most preferably 80° to 1000°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

The liquid pharmaceutical preparation strikes the nozzle body with an entry pressure of up to 600 bar, preferably 200 bar to 300 bar, and is atomized into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g., a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomizer axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomizer; this causes the deformable ring to deform in the annual plane. Details of the construction of the locking mechanism are given in WO 97/20590.

The lower housing part is pushed axially over the spring housing and covers the mounting, the drive of the spindle and the storage container for the fluid.

When the atomizer is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360 degrees, e.g. 180 degrees. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomized may be pushed into the atomizer one after another and used in succession. The storage container contains the aqueous aerosol preparation according to the invention.

The atomizing process is initiated by pressing gently on the actuating button. As a result, the locking mechanism opens up the path for the power takeoff member. The biased spring pushes the plunger into the cylinder of the pump housing. The fluid leaves the nozzle of the atomizer in atomized form.

Further details of construction are disclosed in PCT Applications WO 97/12683 and WO 97/20590, to which reference is hereby made, and each of which is incorporated herein by reference in their entireties.

The components of the atomizer (nebulizer) are made of a material which is suitable for its purpose. The housing of the atomizer and, if its operation permits, other parts as well are preferably made of plastics, e.g., by injection moulding. For medicinal purposes, physiologically safe materials are used.

Figure 2A:
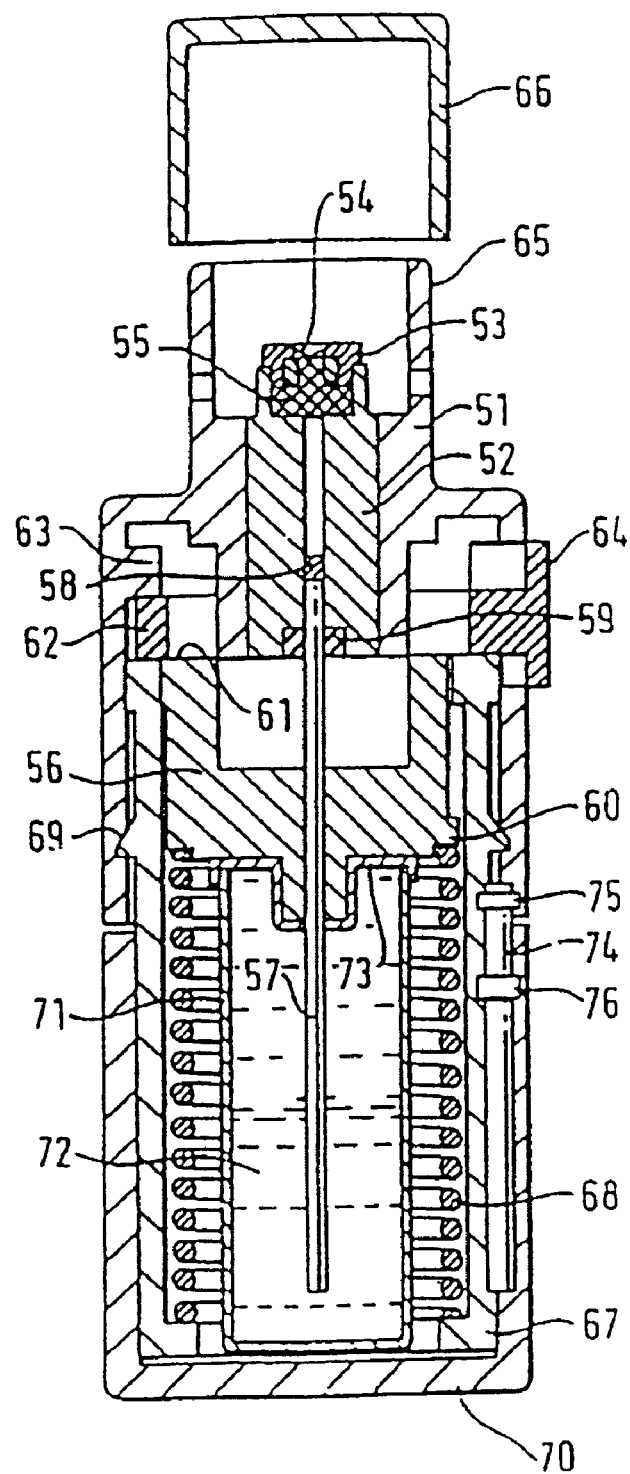
FIG. 2a shows a longitudinal section of the Respimat® nebulizer disclosed in WO 97/12687 through the atomizer with the spring under tension.

FIGS. 2*a/b* attached to this patent application, which are identical to FIGS. 6*a/b* of WO 97/12687, show the nebulizer (Respimat®) which can advantageously be used for inhaling the aqueous aerosol preparations according to the invention.

Figure 2B:
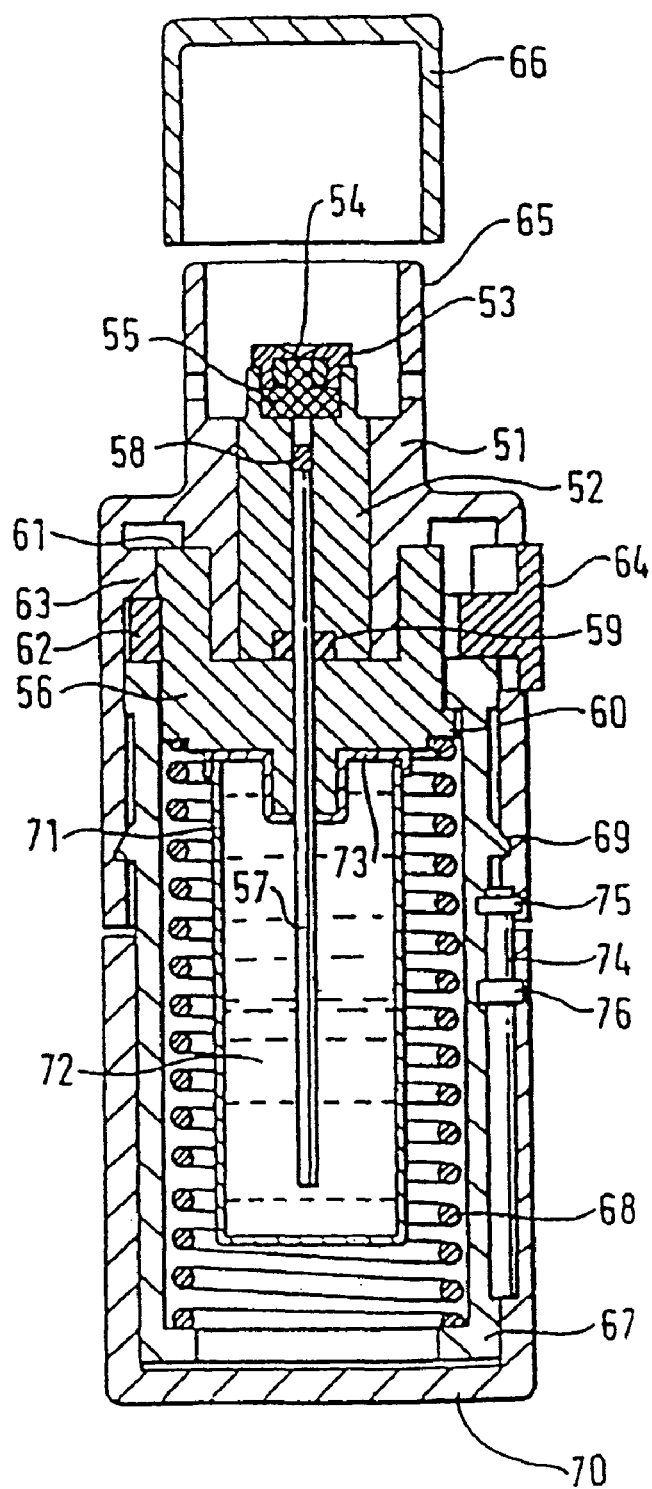
FIG. 2b shows a longitudinal section of the Respimat® nebulizer disclosed in WO 97/12687 through the atomizer with the spring released.

FIG. 2*a* shows a longitudinal section through the atomizer with the spring biased, while FIG. 2*b* shows a longitudinal section through the atomizer with the spring relaxed.

The upper housing part (51) contains the pump housing (52) on the end of which is mounted the holder (53) for the atomizer nozzle. In the holder is the nozzle body (54) and a filter (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomized. The storage container is sealed off by the stopper (73) through which the hollow plunger projects into the storage container and is immersed at its end in the fluid (supply of active substance solution).

The spindle (74) for the mechanical counter is mounted in the covering of the spring housing. At the end of the spindle facing the upper housing part is the drive pinion (75). The slider (76) sits on the spindle.

The nebulizer described above is suitable for nebulizing the aerosol preparations according to the invention to produce an aerosol suitable for inhalation.

If the formulation according to the invention is nebulized using the method described above (Respimat®) the quantity delivered should correspond to a defined quantity with a tolerance of not more than 25%, preferably 20% of this amount in at least 97%, preferably at least 98% of all operations of the inhaler (spray actuations). Preferably, between 5 and 30 mg of formulation, most preferably between 5 and 20 mg of formulation are delivered as a defined mass on each actuation. However, the formulation according to the invention may also be nebulized by means of inhalers other than those described above, e.g., jet stream inhalers or other stationary nebulizers.

Accordingly, in a further aspect, the invention relates to pharmaceutical formulations in the form of propellant-free inhalable solutions or suspensions as described above combined with a device suitable for administering these formulations, preferably in conjunction with the Respimat®. Preferably, the invention relates to propellant-free inhalable solutions or suspensions characterized by the combination of active substances 1 and 2 according to the invention in conjunction with the device known by the name Respimat®. In addition, the present invention relates to the above-mentioned devices for inhalation, preferably the Respimat®, characterized in that they contain the propellant-free inhalable solutions or suspensions according to the invention as described hereinbefore.

The propellant-free inhalable solutions or suspensions according to the invention may take the form of concentrates or sterile inhalable solutions or suspensions ready for use, as well as the above-mentioned solutions and suspensions designed for use in a Respimat®. Formulations ready for use may be produced from the concentrates, for example, by the addition of isotonic saline solutions. Sterile formulations ready for use may be administered using energy-operated fixed or portable nebulizers which produce inhalable aerosols by means of ultrasound or compressed air by the Venturi principle or other principles.

Accordingly, in another aspect, the present invention relates to pharmaceutical compositions in the form of propellant-free inhalable solutions or suspensions as described hereinbefore which take the form of concentrates or sterile formulations ready for use, combined with a device suitable for administering these solutions, characterized in that the device is an energy-operated free-standing or portable nebulizer which produces inhalable aerosols by means of ultrasound or compressed air by the Venturi principle or other methods.

The Examples which follow serve to illustrate the present invention in more detail without restricting the scope of the invention to the following embodiments by way of example.

Starting Materials

Tiotropium Bromide

The tiotropium bromide used in the following formulations examples may be obtained as described in European Patent Application 418 716 A1.

In order to prepare the inhalable powders according to the invention, crystalline tiotropium bromide monohydrate may also be used. This crystalline tiotropium bromide monohydrate may be obtained by the method described below.

15.0 µg of tiotropium bromide are placed in 25.7 µg of water in a suitable reaction vessel. The mixture is heated to 80° C.-90° C. and stirred at constant temperature until a clear solution is formed. Activated charcoal (0.8 µg) moistened with water is suspended in 4.4 µg of water, this mixture is added to the solution containing the tiotropium bromide and the resulting mixture is rinsed with 4.3 µg of water. The mixture thus obtained is stirred for at least 15 minutes at 80° C.-90° C. and then filtered through a heated filter into an apparatus preheated to an external temperature of 70° C. The filter is rinsed with 8.6 µg of water. The contents of the apparatus are cooled at 3° C.-5° C. for every 20 minutes to a temperature of between 20° C.-25° C. The apparatus is cooled further to 10-15° C. using cold water and crystallization is completed by stirring for at least another hour. The crystals are isolated using a suction filter dryer, the crystal slurry isolated is washed with 9 liters of cold water (10° C.-15° C.) and cold acetone (10° C.-15° C.). The crystals obtained are dried at 25° C. in a nitrogen current over a period of 2 hours. Yield: 13.4 µg of tiotropium bromide monohydrate (86% of theory).

The crystalline tiotropium bromide monohydrate thus obtained is micronised by known methods in order to prepare the active substance in the form of the average particle size corresponding to the specifications according to the invention.

In order to prepare the compounds 2d mentioned within the scope of the present invention and not known in the prior art:

N-[2-(3,5-bis-trifluoromethyl-phenyl)-ethyl]-2-14-[(3-hydroxy-propyl)-methyl-amino-piperidin-1-yl]-N-methyl-2-phenyl-acetamide a) 33 µg of 1-benzyl-4-piperidone and 15 µg of 3-aminopropanol are combined with a catalytic amount of p-toluenesulphonic acid in 300 ml of toluene and refluxed using the water separator until the calculated amount of water has been drawn off. Then the toluene is distilled off, the residue is dissolved in 250 ml of alcohol and cooled to about 5° C. A total of 6.6 g of sodium borohydride is added batchwise with stirring and the mixture is stirred for 30 hours at ambient temperature. It is combined with 50 ml of acetone, stirred for about half an hour and then the solvents are eliminated in vacuo. The residue is combined with 100 ml of water and extracted twice with 150 ml of methylene chloride. The combined organic phases are dried. The mixture is filtered, the solvent is eliminated in vacuo, the residue is taken up in 80 ml of alcohol, combined with 40 ml of 32% hydrochloric acid, diluted with acetone and stirred for about an hour. The crystals then precipitated are suction filtered and dried. 1-Benzyl-4-(3-hydroxypropylamino)-piperidine is obtained as the dihydrochloride.

b) From 47.4 µg of 1-benzyl-4-(3-hydroxypropylamino)-piperidine-dihydrochloride the base is liberated, combined with 63 ml of 85% formic acid and 22 ml of 37% formaldehyde solution and stirred for two hours at about 90-100° C. The mixture is left to cool, 37 ml of formic acid and 11 ml of formaldehyde solution are added and it is stirred for another hour at about 100-110° C. It is left to cool, combined with 150 ml of methanol, made alkaline with about 270 ml of 32% sodium hydroxide solution with cooling and stirred for about another 30 minutes at 40-50° C. and then the methanol is distilled off. The residue is extracted with twice 100 ml of methylene chloride, the combined methylene chloride phases are dried, filtered and freed from solvent in vacuo. The residue is taken up in 80 ml Ethanol, acidified with 34 ml of 32% hydrochloric acid, combined with 100 ml of acetone and stirred. As soon as crystals have been precipitated more acetone is added. The precipitate is suction filtered, washed with acetone and dried. 42.8 µg of 1-benzyl-4-[-(3-hydroxypropyl)-methylamino]-piperidine-dihydrochloride are obtained in the form of a solid.

c) 42.8 µg of 1-benzyl-4-[(3-hydroxypropyl)-methylamino]-piperidine-dihydrochloride are dissolved in 450 ml of methanol, combined with 5 µg of 5% palladium-charcoal and hydrogenated at about 50° C. with hydrogen at 4-5 bar. The catalyst is filtered off, the methanol is distilled off and the residue is stirred in acetone. Ether is added, the mixture is left to stand for about two hours and then the crystals are suction filtered. 28.7 μg of 4-[-(3-hydroxypropyl)-methylamino]-piperidine-dihydrochloride are obtained in the form of a solid.

d) 9 μg of 4-[-(3-hydroxypropyl)-methylamino]-piperidine-dihydrochloride are dissolved together with 14.5 g of N-[2-(3,5-bis-trifluoromethyl-phenyl)-ethyl]-2-methanesulphonyloxy-N-methyl-2-phenyl-acetamide (prepared analogously to the method described in WO 99/62893) in 125 ml DMF, combined with 20.5 g of potassium carbonate and stirred for about four hours at 80-90° C. After cooling the mixture is poured onto ice, extracted twice with 150 ml of ethyl acetate, the combined organic phases are twice washed with water and dried. The desiccant is filtered off, the solvent is eliminated in vacuo and the residue is chromatographed with methylene chloride/methanol/conc. ammonia solution 95:5:0.5 over silica gel. The uniform fractions according to TLC are combined and freed from solvent in vacuo. The residue of 9.5 g is taken up in methanol and combined with 3.4 g of fumaric acid. Then the methanol is distilled off apart from a small residue, acetone is added and the resulting mixture is stirred for about 30 minutes. The crystals precipitated are suction filtered, washed with acetone and ether and dried. 9 g of N-2-N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide are obtained as the colourless sesquifulmarate, m.p. 139-144° C.

$^1$H-NMR (250 MHz, CD$_3$OD) δ=7,85-7,26 (8H, m); 6,71 (3H, s); 4,50; 4,49 (1H, 2s); 3,67 (2H, t, J=6,0 Hz); 3,89-3,09 (7H, m); 3,21; 3,00 (4H, m); 2,69; 2,94 (3H,); 2,77 (3H, s); 2,49-1,63 (6H, m); most of the signals are cleaved as a result of amide rotation.

N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide a) 2.75 μg of 2-aminopropan-1,3-diol and 5.9 μg of 1-benzyl-4-piperidone are dissolved in 60 ml of methylene chloride and while cooling with ice a total of 9.9 g of sodium triacetoxyborohydride are added batchwise. The mixture is left to stand overnight at ambient temperature. 60 ml of methylene chloride and some water are added, then conc. hydrochloric acid is added while cooling with ice until an acid reaction is obtained. The mixture is stirred for about another 15 min. with cooling and then made clearly alkaline with 4 N sodium hydroxide solution. The aqueous phase is separated off, the organic phase is washed with a very little water, dried over sodium sulphate and freed from solvent in vacuo. 8 g of substance are obtained which are chromatographed with methylene chloride/methanol 8:2 over 150 g of silica gel. The uniform fractions according to TLC are combined and freed from solvent in vacuo. 7.3 μg of 1-benzyl-4-(1,3-dihydroxyprop-2-ylamino)-piperidine are obtained.

b) 34.5 μg of 1-benzyl-4-(1,3-dihydroxyprop-2-ylamino)-piperidine are dissolved in 400 ml of methanol, combined with 3.4 μg of 20% palladium-charcoal and hydrogenated with hydrogen at 24-28° C. under 2.2 bar. Then the catalyst is filtered off and the solvent is eliminated in vacuo. 22.7 μg of 4-(1,3 -dihydroxyprop-2-ylamino)-piperidine are obtained as an oil, which is used for the next reaction without any further purification.

c) 9 μg of 4-(1,3-dihydroxyprop-2-ylamino)-piperidine are reacted with 22.7 g of N-[2-(3,5-bis-trifluoromethyl-phenyl)-ethyl]-2-methanesulphonyloxy-N-methyl-2-phenyl-acetamide in 110 ml DMF with 7.2 ml of triethylamine as base analogously to Example 1, reaction time 5 h at 60-70° C. The crude product is chromatographed over silica gel with methylene chloride/methanol 9:1. The uniform fractions according to TLC are combined. The oily residue is taken up in ethyl acetate and a little water, the aqueous phase is made alkaline with conc. sodium hydroxide solution. The aqueous phase is separated off, the organic phase is dried and freed from solvent in vacuo. The residue is brought to crystallisation in acetone with methanesulphonic acid. 11 g of N-2-(3,5-N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide are obtained as the colourless methanesulphonate.

$^1$H-NMR (250 MHz, CD$_3$OD) δ=7.95-7.31 (8H, m); 4.37; 4.31 (1H, 2s); 3.77 (5H, m); 3.28 (1H, m); 3.05; 3.01 (4H, m); 2.74 (3H, s); 3.45-2.08 (4H, m); 2.07-1.52 (4H, m). Most of the signals are cleaved as a result of amide rotation.

N-[2-(3,5-bis-trifluoromethyl-phenyl)-ethyl]-2-[4-(cyclopropylmethyl-methyl-amino)-piperidin-1-yl]-N-methyl-2-phenyl-acetamide a) 19 μg of 1-benzyl-4-piperidone are combined with 10 g Raney nickel (moistened by rinsing with a little methanol) and 40 g of methylamine in 150 ml of water and hydrogenated for eight hours at ambient temperature under 5 bars of hydrogen. Then the catalyst is filtered off, methanol and excess methylamine are eliminated in vacuo. The mixture is extracted with ethyl acetate, the organic phase is dried over sodium sulphate, filtered and evaporated down in vacuo. 19.2 g of a yellow oil are obtained, which is used for the next reaction without any further purification.

b) 18.9 μg of 1-benzyl-4-methylaminopiperidine as the oil prepared according to a) are taken up in 250 ml of methanol and combined with 8.3 g of cyclopropanecarboxaldehyde and 11.3 g of sodium cyanoborohydride. The mixture is stirred for 5 hours at 40-50° C., then for about another 16 hours at ambient temperature. It is then acidified with 2 N hydrochloric acid, evaporated to dryness in vacuo and the residue is taken up in water. It is washed with ether, made alkaline with concentrated sodium hydroxide solution and extracted with ether/ethyl acetate. The organic extract is dried over sodium sulphate and freed from the solvents in vacuo. 22.7 g 1-benzyl-4-(cyclopropylmethyl-methyl-amino)-piperidine are obtained as a yellowish oil.

c) 21.5 g of the oil prepared according to b) are taken up in 230 ml of methanol, combined with 2.5 μg of 10% palladium-charcoal and hydrogenated at 60° C. under 5 bars of hydrogen. After 3.5 hours the catalyst is renewed and the mixture is hydrogenated for a further five hours at 80° C. under 5 bars of hydrogen. Then the catalyst is filtered off and the solvent is eliminated in vacuo. 4-(Cyclopropylmethyl-methyl-amino)-piperidine is precipitated from the residue as the dihydrochloride with ethanolic hydrochloric acid. It is washed with ether, dried in vacuo and 12.5 g of colourless crystals are obtained.

d) 11.9 μg of 4-(Cyclopropylmethyl-methyl-amino)-piperidine-dihydrochloride are taken up in 400 ml of acetone and combined with 21.7 g of N-[2-(3,5-bis-trifluoromethyl-phenyl)-ethyl]-2-methanesulphonyloxy-N-methyl-2-phenyl-acetamide and 21 ml of triethylamine. The mixture is refluxed for 16 hours, then the solvent is eliminated in vacuo and the residue is taken up in 10% sodium hydrogen carbonate solution. It is extracted with ether, the combined organic phases are dried over sodium sulphate and freed from solvent in vacuo. The residue is filtered with ethyl acetate/methanol/conc. ammonia solution 70:30:1 over silica gel, freed from the solvents in vacuo and brought to crystallisation in methanol with fumaric acid. The precipitate is suction filtered, washed with methanol and dried in vacuo. 9.3 g of N-[2-(3,5-bis-trifluoromethyl-phenyl)-ethyl]-2-[4-(cyclopropylmethyl-methyl-amino)-piperidin-1-yl]-N-methyl-2-phenyl-acetamide are obtained as the sesquifumarate.

$^1$H-NMR (250 MHz, CDCl$_3$) δ=7.71-7.14 (8H, m); 4.14 (1H, s); 3.81-2.46 (11H, m); 2.90; 2.82 (3H, 2s); 2.36 (3H, s); 2.23-1.48 (4H, m); 0.82 (1H, m); 0.48; 0.07 (4H, 2m). Most of the signals are cleaved as a result of amide rotation.

N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide a) 6 μg of 2-hydroxyethyl-3-hydroxypropylamine and 18.9 μg of 1-benzyl-4-piperidone are taken up in 250 ml methylene chloride and at 0° C. combined with 21.2 g of sodium triacetoxyborohydride. The mixture is stirred overnight at ambient temperature, then acidified with 2 N hydrochloric acid and made alkaline with concentrated sodium hydroxide solution. It is extracted with methylene chloride, the extract is dried over sodium sulphate and the solvent is eliminated in vacuo. The residue is chromatographed over silica gel with ethyl acetate/methanol/conc. ammonia solution 20:80:1. The uniform fractions according to TLC are combined and freed from solvent in vacuo. 2.3 μg of 1-benzyl-4-[(2-hydroxy-ethyl)-(3-hydroxy-propyl)-amino]-piperidine are obtained as an oil.

b) 13.3 μg of 1-benzyl-4-[(2-hydroxy-ethyl)-(3-hydroxy-propyl)-amino]-piperidine are combined with 1.5 μg of 10% palladium-charcoal in 150 ml of methanol and hydrogenated at ambient temperature for 18 hours under 5 bars of hydrogen. The catalyst is renewed after 8 hours and 15 hours. Then the catalyst is filtered off and the filtrate is freed from solvent in vacuo. 4-[(2-Hydroxy-ethyl)-(3-hydroxy-propyl)-amino]-piperidine are obtained as an oil, which is used for the next reaction without any further purification.

c) 6.4 g of the oil of 4-[(2-hydroxy-ethyl)-(3-hydroxy-propyl)-amino]-piperidine prepared according to b) are taken up in 300 ml of acetone, combined with 13.8 g of N-[2-(3,5-bis-trifluoromethyl-phenyl)-ethyl]-2-methanesulphonyloxy-N-methyl-2-phenyl-acetamide and 33 ml of triethylamine and refluxed for 6 hours. The mixture is cooled, the solvent is eliminated in vacuo, the residue is stirred into 10% sodium hydrogen carbonate solution and extracted with ethyl acetate. The combined organic phases are dried over sodium sulphate, the solvent is eliminated in vacuo and the residue is chromatographed over silica gel with ethyl acetate/methanol/conc. ammonia solution 20:80:1. The uniform fractions according to TLC are combined and freed from the solvents in vacuo. 8.4 g of N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide are obtained as a yellowish-brown oil.

$^1$H-NMR (250 MHz, CDCl$_3$) δ=7.78-7.24 (8H, m); 4.24 (1H, s); 3.78 (2H, m); 3.61 (2H, m); 3.64 (1H, m); 2.98; 2.87 (3H, 2s); 2.93 (4H, m); 2.74; 2.65 (4H, 2m); 2.88-1.77 (4H, m); 1.67 (2H, m); 1.76-1.45 (4H, m). Most of the signals are cleaved as a result of amide rotation.

(S)-N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide a) 16.5 μg of 3-aminopropanol and 41.7 μg of 1-benzyl-4-piperidone are dissolved in 350 ml methylene chloride and at about 10C 56 g of sodium triacetoxy-borohydride are slowly added. The mixture is stirred overnight at ambient temperature, then acidified with dilute hydrochloric acid with cooling and subsequently made alkaline with conc. sodium hydroxide solution. The organic phase is separated off, the aqueous phase is washed once again with 150 ml of methylene chloride. The combined organic phases are dried over sodium sulphate and freed from solvent in vacuo. 32 g 1-benzyl-4-(3-hydroxy-propylamino)-piperidine are obtained as a yellow oil which is used in the next reaction step without any further purification.

b) 13.4 μg of 1-benzyl-4-(3-hydroxy-propylamino)-piperidine from the previous reaction are dissolved together with 3.8 g of cyclopropanecarboxaldehyde in 250 ml of methanol and at 0° C. combined with 5.1 g of sodium cyanoborohydride. The mixture is stirred overnight at ambient temperature, then acidified with dilute hydrochloric acid with cooling and evaporated down in vacuo. The mixture is then made alkaline with conc. sodium hydroxide solution and extracted three times with 40 ml of methylene chloride. The combined organic phases are dried over sodium sulphate, filtered and freed from solvent in vacuo. The residue is filtered over silica gel with ethyl acetate/methanol/conc. ammonia solution 20:80:1. After the solvent has been eliminated 10.2 μg of 1-benzyl-4-[cyclopropylmethyl-(3-hydroxy-propyl)-amino]-piperidine are obtained as a yellow oil.

c) 10.2 μg of 1-benzyl-4-[cyclopropylmethyl-(3-hydroxy-propyl)-amino]-piperidine are combined with 2 μg of 20% palladium-charcoal in 100 ml of methanol and hydrogenated at 60° C. for 4 h under 5 bars of hydrogen. The catalyst is separated off, the solvent is eliminated in vacuo and 7.3 μg of 4-[cyclopropylmethyl-(3-hydroxy-propyl)-amino]-piperidine are obtained as a yellow oil.

d) 4.7 μg of 4-[cyclopropylmethyl-(3-hydroxy-propyl)-amino]-piperidine are stirred together with 9.6 g of (R)-N-[2-(3,5-bis-trifluoromethyl-phenyl)-ethyl]-2-methanesulphonyloxy-N-methyl-2-phenyl-acetamide (prepared from D-(−)-mandelic acid) and 3.4 ml of triethylamine in 200 ml of acetone for four hours at 65° C. The mixture is evaporated down in vacuo, combined with 100 ml of saturated sodium hydrogen carbonate solution and extracted with ethyl acetate. The combined organic fractions are dried over sodium sulphate and freed from solvent in vacuo. The residue is chromatographed with methylene chloride/methanol 1:1 over silica gel. The uniform fractions according to TLC are collected and the solvents are eliminated in vacuo. 5.5 g of (S)-N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide are obtained as a yellowish-brown oil, [α]D$^{20}$=+29.6°.

$^1$H-NMR (250 MHz, CDCl$_3$) δ=7.78-7.26 (8H, m), 4.24 (1H, s), 3.78 (2H, m); 3,63 (2H, m); 3.50 (1H, m); 2.96; 2.88 (3H, 2s); 2.93 (4H, m); 2.88-1.77 (5H, m); 2.37 (2H, d, J=6.0 Hz); 1.79-1.45 (6H, m); 0.87 (1H, m); 0.52; 0.12 (4H, 2m).

Most of the signals are cleaved as a result of amide rotation.

In order to prepare compounds 22 mentioned within the scope of the present invention and not yet known in the art:

I.) 4-[(3-chloro-4-fluoro-phenyl)amino]-7-{3-[4-(2-oxo-tetrahydrofuran-4-yl)-piperazin-1-yl]-propyloxy}-6-[(vinylcarbonyl)amino]-quinazoline A mixture of 166 mg acrylic acid and 0.77 ml triethylamine in 10 ml of tetrahydrofuran is cooled to −50° C. in a dry ice/acetone cooling bath and combined with a solution of 175 μl acrylic acid chloride in 4 ml of tetrahydrofuran. The reaction mixture is stirred at this temperature for 45 minutes. Then a solution of 427 mg of 6-amino-4-[(3-chloro-4-fluoro-phenyl)amino]-7-{3-[4-(2-oxo-tetrahydrofuran-4-yl)-piperazin-1-yl]-propyloxy}-quinazoline in 10 ml of tetrahydrofuran is added dropwise within 20 minutes. The reaction mixture is then slowly allowed to warm up to 0° C. and stirred at this temperature until the reaction is complete. It is then combined with ice water whereupon a viscous precipitate is formed. This is extracted thoroughly several times with ethyl acetate/methanol. The combined organic phases are washed with saturated sodium chloride solution, dried over magnesium sulphate and evaporated down. The yellowish, resinous crude product is purified by chromatography over a silica gel column with methylene chloride/methanol (95:5) as eluant.

Yield: 148 mg (31% of theory),
$R_f$ value: 0.45 (silica gel, methylene chloride/methanol/concentrated aqueous ammonia solution=90:10:0.1)
Mass spectrum (ESI$^+$): m/z=567, 569 [M−H]$^+$ The following compound is obtained analogously to I.):
4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline
$R_f$ value: 0.46 (silica gel, methylene chloride/methanol/concentrated aqueous ammonia solution=90:10:0.1)
Mass spectrum (ESI$^+$): m/z=581, 583 [M−H]$^+$

II.) 4-[(3-chloro-4-fluoro-phenyl)amino]-7-[3-(2,2-dimethyl-6-oxo-morpholin-4-yl)-propyloxy]-6-[(vinylcarbonyl)amino]-quinazoline 0.47 ml triethylamine are added to 101 mg of acrylic acid in 5 ml of tetrahydrofuran under a nitrogen atmosphere. This mixture is cooled to about −50° C. in a dry ice/acetone cooling bath and combined with 119 mg acrylic acid chloride in 3 ml of tetrahydrofuran, whereupon a colourless precipitate is formed. The suspension is stirred for about another hour at this temperature. Then 240 mg of 6-amino-4-[(3-chloro-4-fluoro-phenyl)amino]-7-[3-(2,2-dimethyl-6-oxo-morpholin-4-yl)-propyloxy]-quinazoline in 7 ml of tetrahydrofuran are added dropwise at −55° C. The reaction mixture is allowed to heat up slowly to −30° C. After about an hour the dry ice/acetone cooling bath is exchanged for an ice/sodium chloride cooling bath. The reaction mixture is then allowed to come up to 0° C. therein. As soon as the reaction is complete, the reaction mixture is combined with water and methylene chloride and made alkaline with sodium hydroxide solution. The aqueous phase separated off is extracted again with methylene chloride and a little methanol. The combined organic extracts are washed with water, dried and evaporated down. A yellow resin remains which is chromatographed through a silica gel column with methylene chloride/methanol (98:2) as eluant. The desired product is stirred with a little tert.butylmethyl ether, the fine crystalline precipitate is suction filtered, washed again with tert.butylmethyl ether and dried in vacuo at 50° C.

Yield: 160 mg (60% of theory),
$R_f$ value: 0.42 (silica gel, methylene chloride/methanol=95:5)
Mass spectrum (ESI$^+$): m/z=526, 528 [M−H]$^+$ The following compounds are obtained analogously to II.):
(1)  4-[(3-chloro-4-fluoro-phenyl)amino]-7-[2-((S)-6-methyl-2-oxo-morpholin-4-yl)-ethoxy]-6-[(vinylcarbonyl)amino]-quinazoline
$R_f$ value: 0.32 (silica gel, methylene chloride/methanol=95:5)
Mass spectrum (ESI$^+$): m/z=498, 500 [M−H]$^+$
(2)  4-[(3-chloro-4-fluoro-phenyl)amino]-7-[4-((R)-6-methyl-2-oxo-morpholin-4-yl)-butyl-oxy]-6-[(vinylcarbonyl) amino]-quinazoline $R_f$ value: 0.30 (silica gel, methylene chloride/methanol=95:5)
Mass spectrum (ESI$^+$): m/z=550, 552 [M+Na]$^+$
(3)  4-[(3-chloro-4-fluoro-phenyl)amino]-7-[4-((S)-6-methyl-2-oxo-morpholin-4-yl)-butyl-oxy]-6-[(vinylcarbonyl) amino]-quinazoline
Mass spectrum (ESI$^+$): m/z=526, 528 [M−H]$^+$

III.) 4-[(3-chloro-4-fluorophenyl)amino]-6-{[4-(N,N-diethylamino)-1-oxo-2-buten-1-yl]amino}-7-cyclopropylmethoxy-quinazoline 0.67 ml oxalyl chloride and one drop of dimethylformamide are added at ambient temperature to a solution of 640 mg of 4-bromo-2-butenoic acid in 10 ml methylene chloride. The reaction mixture is stirred for about another half hour at ambient temperature until the development of gas has ended. The acid chloride produced is largely freed from solvent using the rotary evaporator in vacuo. Then the crude product is dissolved in 10 ml of methylene chloride and added dropwise while cooling with an ice bath to a mixture of 1.00 μg of 6-amino-4-[(3-chloro-4-fluorophenyl)amino]-7-cyclopropylmethoxy-quinazoline and 1.60 ml of Hünig base in 50 ml of tetrahydrofuran. The reaction mixture is stirred for 1.5 hours in the ice bath and for a further 2 hours at ambient temperature. Then 2.90 ml of diethylamine are added and the mixture is stirred for 2.5 days at ambient temperature. For working up, the reaction mixture is filtered and the filtrate is evaporated down. The flask residue is purified by chromatography over a silica gel column with ethyl acetate/methanol (19:1).

Yield: 550 mg (40% of theory)
melting point: 114° C.
Mass spectrum (ESI$^+$): m/z=498, 500 [M+H]$^+$ The following compounds are obtained analogously to III.):
(1) 4-[(3-chloro-4-fluoro-phenyl)amino]-6-{[4-(morpholin-4-yl)-1-oxo-2-buten-1-yl]-amino}-7-cyclopropylmethoxy-quinazoline
$R_f$ value: 0.53 (silica gel, ethyl acetate/methanol=9:1)
Mass spectrum (ESI$^+$): m/z=510, 512 [M−H]$^+$
(2)  4-[(3-chloro-4-fluorophenyl)amino]-6-{[4-(N,N-dimethylamino)-1-oxo-2-buten-1-yl]-amino}-7-cyclopropylmethoxy-quinazoline
melting point: 137° C.
Mass spectrum (ESI$^+$): m/z=470, 472 [M+H]$^+$
(3)  4-[(R)-(1-phenyl-ethyl)amino]-6-{[4-(morpholin-4-yl)-1-oxo-2-buten-1-yl]amino}-7-cyclopropylmethoxy-quinazoline
$R_f$ value: 0.37 (silica gel, ethyl acetate/methanol=9:1)
Mass spectrum (ESI$^+$): m/z=488 [M+H]$^+$
(4)  4-[(R)-(1-phenyl-ethyl)amino]-6-{[4-(morpholin-4-yl)-1-oxo-2-buten-1-yl]amino}-7-cyclopentyloxy-quinazoline
$R_f$ value: 0.35 (silica gel, ethyl acetate/methanol=9:1)
Mass spectrum (ESI$^+$): m/z=502 [M+H]$^+$

IV.) 4-[(3-methylphenyl)amino]-6-[(4-{N-[(ethoxy-carbonyl)methyl]-N-methylamino}-1-oxo-2-buten-1-yl)amino]-7-methoxy-quinazoline 0.86 ml of oxalyl chloride and one drop of dimethylformamide are added to a solution of 842 mg of 4-bromo-2-butenoic acid in 15 ml methylene chloride at ambient temperature. The reaction mixture is stirred for about another hour at ambient temperature until the development of gas has ended. The acid chloride formed is largely freed from solvent in vacuo using the rotary evaporator. Then the crude product is taken up in 10 ml methylene chloride and added dropwise within five minutes to a mixture of 1.0 µg of 6-amino-4-[(3-methylphenyl)amino]-7-methoxy-quinazoline and 2.0 ml of Hünig base in 50 ml of tetrahydrofuran while cooling with an ice bath. The reaction mixture is stirred for two hours while cooling with an ice bath and then for another two hours at ambient temperature. Then 6.7 ml Hünig base, 5.48 g sarcosine ethylester hydrochloride and 3 ml of dimethylformamide are added and the whole is stirred overnight at ambient temperature. For working up the reaction mixture is evaporated down in vacuo using the rotary evaporator and the flask residue is distributed between 75 ml ethyl acetate and 75 ml of water. The organic phase is washed with water and saturated sodium chloride solution, dried over magnesium sulphate and evaporated down. The crude product is purified by chromatography over a silica gel column with methylene chloride/methanol (20:1).

Yield: 326 mg (20% of theory)

melting point: 122-124° C.

Mass spectrum (ESI$^+$): m/z=464 [M+H]$^+$

The following compound is obtained analogously to IV.):

4-[(3-chloro-4-fluorophenyl)amino]-6-[(4-{N-[2-(ethoxycarbonyl)-ethyl]-N-[(ethoxycarbonyl)methyl]amino}-1-oxo-2-buten-1-yl)amino]-7-cyclopropylmethoxy-quinazoline R$_f$ value: 0.62 (aluminium oxide, cyclohexane/ethyl acetate=1:1)

Mass spectrum (EI): m/z=627, 629 [M]$^+$

V.) 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 950 mg of 4-[(3-chloro-4-fluoro-phenyl)amino]-6-[(4-{N-[(ethoxycarbonyl)methyl]-N-((R)-2-hydroxy-3-methoxy-propyl)-amino}-1-oxo-2-buten-1-yl)amino]-7-cyclopropylmethoxy-quinazoline and 195 µl of methanesulphonic acid in 10 ml acetonitrile are refluxed for about four hours. For working up the reaction mixture is cooled in a bath of ice water, combined with 75 ml ethyl acetate and 25 ml saturated sodium hydrogen carbonate solution and stirred vigorously for 10 minutes. The organic phase is separated off, washed with saturated sodium hydrogen carbonate solution and saturated sodium chloride solution and dried over magnesium sulphate. The solvent is distilled off in vacuo, leaving a brownish foam.

Yield: 610 mg (69% of theory),

R$_f$ value: 0.55 (silica gel, methylene chloride/methanol=9:1)

Mass spectrum (ESI$^+$): m/z=570, 572 [M+H]$^+$

VI.) 4-[(3-chloro-4-fluoro-phenyl)amino]-6-{[4-((S)-6-methyl-2-oxo-morpholin-4-yl)-1-oxo-2-buten-1-yl]amino}-7-cyclopropylmethoxy-quinazoline A mixture of 700 mg of 4-[(3-chloro-4-fluoro-phenyl)amino]-6-[(4-{N-[(tert.butyl-oxycarbonyl)methyl]-N-((S)-2-hydroxy-prop-1-yl)-amino}-1-oxo-2-buten-1-yl)amino]-7-cyclopropylmethoxy-quinazoline and 228 mg of p-toluenesulphonic acid hydrate in 20 ml of acetonitrile is refluxed for five hours. Then a further 200 mg of p-toluenesulphonic acid hydrate are added and the mixture is again refluxed for five hours. For working up the reaction mixture is evaporated to dryness. The flask residue is distributed between ethyl acetate and saturated sodium carbonate solution. The organic phase is separated off, washed with saturated sodium carbonate solution, water and saturated sodium chloride solution, dried over magnesium sulphate and evaporated down. The oily residue is brought to crystallisation by stirring with 15 ml diethyl ether.

Melting point: 173-175° C.

Mass spectrum (ESI$^+$): m/z=540, 542 [M+H]$^+$

The following compounds are obtained analogously to VI.):

(1) 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline R$_f$ value: 0.54 (silica gel, methylene chloride/methanol=9:1)

Mass spectrum (ESI$^+$): m/z=540, 542 [M+H]$^+$ (2) 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline (The reaction is carried out with methanesulphonic acid in acetonitrile)

R$_f$ value: 0.38 (silica gel, methylene chloride/methanol=9:1)

Mass spectrum (ESI$^+$): m/z=556, 558 [M+H]$^+$

VII.) 4-[(3-bromo-phenyl)amino]-6-[2-((S)-6-methyl-2-oxo-morpholin-4-yl)-ethoxy]-7-methoxy-quinazoline 90 µl methanesulphonic acid are added to 380 mg of 4-[(3-bromo-phenyl)amino]-6-(2-{N-[(tert.butyloxycarbonyl)methyl]-N-((S)-2-hydroxy-propyl)-amino}-ethoxy)-7-methoxy-quinazoline in 8 ml acetonitrile. The reaction mixture is refluxed for about three hours, then another equivalent of methanesulphonic acid is added and refluxing is continued until the reaction is complete. For working up the reaction mixture is diluted with ethyl acetate and washed with saturated sodium hydrogen carbonate solution and saturated sodium chloride solution. The organic phase is dried over magnesium sulphate and evaporated down in vacuo. The flask residue is stirred with diethyl ether and suction filtered. The title compound is obtained as a white solid.

Yield: 280 mg (85% of theory),

Melting point: 190° C.

Mass spectrum (ESI$^+$): m/z=485, 487 [M–H]$^+$

The following compound is obtained analogously to VII.):

4-[(3-chloro-4-fluoro-phenyl)amino]-6-[2-((S)-6-methyl-2-oxo-morpholin-4-yl)-ethoxy]-7-methoxy-quinazoline (The reaction is carried out with trifluoroacetic acid in acetonitrile)

melting point: 212-213° C.

Mass spectrum (ESI$^+$): m/z=461, 463 [M+H]$^+$

VIII.) 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4.70 ml of oxalyl chloride are added dropwise to a solution of 4.50 g of bromocrotonic acid in 60 ml of methylene chloride. Then one drop of N,N-dimethylformamide is added. After about 30 minutes the development of gas has ended and the reaction mixture is evaporated down in the rotary evaporator. The crude bromocrotonic acid chloride is taken up in 30 ml methylene chloride and added dropwise to a solution of 7.00 g 4-[(3-chloro-4-fluorophenyl)amino]-6-amino-7-cyclopropylmethoxy-quinazoline and 10.20 ml Hünig base in 150 ml of tetrahydrofuran while cooling with an ice bath. The reaction mixture is stirred for about 1.5 hours while cooling with an ice bath and for a further two hours at ambient temperature. Then 5.20 g of N-(2-methoxy-ethyl)-N-methyl-amine are added and the reaction mixture is stirred overnight at ambient temperature. For working up it is diluted with methylene chloride and washed thoroughly with water. The organic phase is dried over magnesium sulphate and evaporated down. The crude product is purified by chromatography over a silica gel column with ethyl acetate followed by ethyl acetate/methanol (19:1) as eluant.

Yield: 5.07 g (51% of theory)
Mass spectrum (ESI$^+$): m/z=512, 514 [M−H]$^+$
R$_f$ value: 0.25 (silica gel, ethyl acetate/methanol=9:1)

The following compounds are obtained analogously to VIII):

(1) 4-[(3-chloro-4-fluorophenyl)amino]-6-{[4-(N,N-dimethylamino)-1-oxo-2-buten-1-yl]-amino}-7-cyclopentyloxy-quinazoline
Mass spectrum (ESI$^+$): m/z=482, 484 [M−H]$^+$
R$_f$ value: 0.11 (silica gel, ethyl acetate/methanol=9:1)

(2) 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline
Mass spectrum (ESI$^+$): m/z=532 [M−H]$^+$
R$_f$ value: 0.40 (silica gel, ethyl acetate/methanol=9:1)

(3) 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline
Mass spectrum (ESI$^+$): m/z=502 [M−H]$^+$
R$_f$ value: 0.20 (silica gel, ethyl acetate/methanol=9:1)

(4) 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline
Mass spectrum (ESI$^+$): m/z=488 [M−H]$^+$
R$_f$ value: 0.25 (silica gel, ethyl acetate/methanol=9:1)

(5) 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline
Mass spectrum (ESI$^+$): m/z=514 [M−H]$^+$
R$_f$ value: 0.15 (silica gel, ethyl acetate/methanol=9:1)

(6) 4-[(3-chloro-4-fluorophenyl)amino]-6-{[4-(N,N-dimethylamino)-1-oxo-2-buten-1-yl]-amino}-7-((R)-tetrahydrofuran-3-yloxy)-quinazoline
Mass spectrum (ESI$^+$): m/z=486, 488 [M+H]$^+$ (7) 4-[(3-chloro-4-fluorophenyl)amino]-6-{[4-(N,N-dimethylamino)-1-oxo-2-buten-1-yl]-amino}-7-((S)-tetrahydrofuran-3-yloxy)-quinazoline
Mass spectrum (ESI$^+$): m/z=486, 488 [M+H]$^+$
R$_f$ value: 0.45 (silica gel, methylene chloride/methanol=5:1)

(8) 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline
Mass spectrum (ESI$^+$): m/z=528, 530 [M−H]$^+$
R$_f$ value: 0.25 (silica gel, ethyl acetate/methanol=9:1)

(9) 4-[(3-chloro-4-fluorophenyl)amino]-6-{[4-(N-cyclopropyl-N-methyl-amino)-1-oxo-2-buten-1-yl]amino}-7-cyclopentyloxy-quinazoline
Mass spectrum (ESI$^+$): m/z=508, 510 [M−H]$^+$
melting point: 140° C.

(10) 4-[(3-chloro-4-fluorophenyl)amino]-6-{[4-(N,N-dimethylamino)-1-oxo-2-buten-1-yl]-amino}-7-[(R)-(tetrahydrofuran-2-yl)methoxy]-quinazoline
Mass spectrum (ESI$^+$): m/z=500, 502 [M+H]$^+$
melting point: 110-112° C.

(11) 4-[(3-chloro-4-fluorophenyl)amino]-6-{[4-(N,N-dimethylamino)-1-oxo-2-buten-1-yl]-amino}-7-[(S)-(tetrahydrofuran-2-yl)methoxy]-quinazoline
Mass spectrum (ESI$^+$): m/z=500, 502 [M+H]$^+$
R$_f$ value: 0.23 (silica gel, ethyl acetate/methanol/conc. aqueous ammonia=90:10:0.1)

Some particularly preferred formulations according to the invention containing the two components 1 and 2g are described hereinafter without restricting the core of the invention thereto.

Examples of Formulations

| A. Inhalable Powders | |
|---|---|
| Ingredients | μg per capsule |
| Tiotropium bromide | 21.7 |
| Budesonide | 200 |
| Lactose | 4778.3 |
| Total | 5000 |
| Tiotropium bromide | 21.7 |
| Fluticasone propionate | 125 |
| Lactose | 4853.3 |
| Total | 5000 |
| Tiotropium bromide × H$_2$O | 22.5 |
| Mometasone furoate | 250 |
| Lactose | 4727.5 |
| Total | 5000 |
| Tiotropium bromide | 21.7 |
| Ciclesonide | 250 |
| Lactose | 4728.3 |
| Total | 5000 |
| tiotropium bromide monohydrate | 22.5 |
| ciclesonide | 250 |
| lactose | 4727.5 |
| Total | 5000 |
| tiotropium bromide | 21.7 |
| ciclesonide | 250 |
| lactose | 4728.3 |
| Total | 5000 |
| Tiotropium bromide | 21.7 |
| Viozan | 270 |
| Lactose | 4708.3 |
| Total | 5000 |
| Tiotropium bromide | 21.7 |
| Viozan | 45 |
| Lactose | 4933.3 |
| Total | 5000 |

A. Inhalable Powders

| Ingredients | µg per capsule |
|---|---|
| Tiotropium bromide × H₂O | 22.5 |
| Viozan | 495 |
| Lactose | 4482.5 |
| Total | 5000 |
| Tiotropium bromide | 21.7 |
| Viozan | 400 |
| Lactose | 4578.3 |
| Total | 5000 |
| Ipratropium bromide | 40 |
| Viozan | 270 |
| Lactose | 4690 |
| Total | 5000 |
| Ipratropium bromide | 20 |
| Viozan | 45 |
| Lactose | 4935 |
| Total | 5000 |
| Tiotropium bromide | 21.7 |
| Pramipexol | 400 |
| Lactose | 4578.3 |
| Total | 5000 |
| Tiotropium bromide | 21.7 |
| Talipexol | 400 |
| Lactose | 4578.3 |
| Total | 5000 |
| Tiotropium bromide | 21.7 |
| AWD-12-281 | 200 |
| Lactose | 4778.3 |
| Total | 5000 |
| Tiotropium bromide | 21.7 |
| AWD-12-281 | 125 |
| Lactose | 4853.3 |
| Total | 5000 |
| Tiotropium bromide × H₂O | 22.5 |
| AWD-12-281 | 250 |
| Lactose | 4727.5 |
| Total | 5000 |
| Tiotropium bromide | 21.7 |
| AWD-12-281 | 250 |
| Lactose | 4728.3 |
| Total | 5000 |
| Tiotropium bromide × H₂O | 22.5 |
| AWD-12-281 | 495 |
| Lactose | 4482.5 |
| Total | 5000 |
| Tiotropium bromide | 21.7 |
| AWD-12-281 | 400 |
| Lactose | 4578.3 |
| Total | 5000 |
| Tiotropium bromide × H₂O | 22.5 |
| Compound of formula 2ca | 250 |
| Lactose | 4727.5 |
| Total | 5000 |
| Tiotropium bromide | 10.8 |
| NK₁-receptor antagonist | 27.9 |
| Lactose | 4961.3 |
| Total | 5000 |
| Tiotropium bromide | 21.7 |
| NK₁-receptor antagonist | 55.9 |
| Lactose | 4922.4 |
| Total | 5000 |
| Tiotropium bromide × H₂O | 22.5 |
| NK₁-receptor antagonist | 55.9 |
| Lactose | 4921.6 |
| Total | 5000 |
| Tiotropium bromide | 21.7 |
| NK₁-receptor antagonist | 55.9 |
| Lactose | 4922.4 |
| Total | 5000 |
| Tiotropium bromide | 21.7 |
| Endothelin antagonist 2e | 270 |
| Lactose | 4708.3 |
| Total | 5000 |
| Tiotropium bromide | 21.7 |
| Endothelin antagonist 2e | 450 |
| Lactose | 4528.3 |
| Total | 5000 |
| Tiotropium bromide × H₂O | 22.5 |
| Endothelin antagonist 2e | 495 |
| Lactose | 4482.5 |
| Total | 5000 |
| Tiotropium bromide | 21.7 |
| Endothelin antagonist 2e | 1400 |
| Lactose | 3578.3 |
| Total | 5000 |
| Ipratropium bromide | 40 |
| Endothelin antagonist 2e | 2000 |
| Lactose | 2960 |
| Total | 5000 |
| Ipratropium bromide | 20 |
| Endothelin antagonist 2e | 495 |
| Lactose | 4485 |
| Total | 5000 |
| Tiotropium bromide | 21.7 |
| Epinastine hydrochloride | 200 |
| Lactose | 4778.3 |
| Total | 5000 |
| Tiotropium bromide | 21.7 |
| Epinastine hydrochloride | 125 |
| Lactose | 4853.3 |
| Total | 5000 |
| Tiotropium bromide × H₂O | 22.5 |
| Epinastine hydrochloride | 250 |
| Lactose | 4727.5 |
| Total | 5000 |
| Tiotropium bromide | 21.7 |
| Epinastine hydrochloride | 250 |
| Lactose | 4728.3 |
| Total | 5000 |
| Tiotropium bromide × H₂O | 22.5 |
| Epinastine hydrochloride | 495 |
| Lactose | 4482.5 |
| Total | 5000 |
| Tiotropium bromide | 21.7 |
| Epinastine hydrochloride | 400 |
| Lactose | 4578.3 |
| Total | 5000 |
| tiotropium bromide | 10.8 |
| EGFR kinase inhibitor 2g | 3500 |
| Lactose | 3489.2 |
| Total | 7000 |

A. Inhalable Powders

| Ingredients | µg per capsule |
|---|---|
| tiotropium bromide | 21.7 |
| EGFR kinase inhibitor 2g | 3000 |
| Lactose | 3978.3 |
| Total | 7000 |
| tiotropium bromide × H$_2$O | 22.5 |
| EGFR kinase inhibitor 2g | 5000 |
| Lactose | 4022.5 |
| Total | 10000 |
| tiotropium bromide × H$_2$O | 22.5 |
| EGFR kinase inhibitor 2g | 5000 |
| Lactose | 1977.5 |
| Total | 7000 |
| tiotropium bromide × H$_2$O | 22.5 |
| EGFR kinase inhibitor 2g | 5000 |
| Total | 5022.5 |

B. Propellant Gas-Containing Aerosols for Inhalation

| Ingredients | wt. % |
|---|---|
| Tiotropium bromide | 0.029 |
| Budesonide | 0.4 |
| Soya lecithin | 0.2 |
| TG 134a:TG227 (2:3) | to 100 |
| Tiotropium bromide | 0.029 |
| Fluticasone-propionate | 0.3 |
| Isopropyl myristate | 0.1 |
| TG 227 | to 100 |
| Tiotropium bromide | 0.029 |
| Mometasone-furoate | 0.6 |
| Isopropyl myristate | 0.1 |
| TG 227 | to 100 |
| Tiotropium bromide | 0.029 |
| Ciclesonide | 0.4 |
| Isopropyl myristate | 0.1 |
| TG 227 | to 100 |
| tiotropium bromide | 0.029 |
| ciclesonide | 0.4 |
| isopropyl myristate | 0.1 |
| TG227 | ad 100 |
| Tiotropium bromide | 0.015 |
| Viozan | 0.3 |
| Soya lecithin | 0.2 |
| TG 134a:TG227 = 2:3 | ad 100 |
| Ipratropium bromide | 0.015 |
| Viozan | 0.3 |
| soya lecithin | 0.2 |
| TG 227 | ad 100 |
| Tiotropium bromide | 0.029 |
| Viozan | 0.45 |
| absolute ethanol | 0.5 |
| Isopropyl myristate | 0.1 |
| TG 227 | ad 100 |
| Ipratropium bromide | 0.029 |
| Viozan | 0.3 |
| absolute ethanol | 0.5 |
| Isopropyl myristate | 0.1 |
| TG 227 | ad 100 |
| Tiotropium bromide | 0.015 |
| AWD-12-281 | 0.066 |
| Soya lecithin | 0.2 |
| TG 134a:TG227 = 2:3 | ad 100 |
| Tiotropium bromide | 0.029 |
| AWD-12-281 | 0.033 |
| absolute ethanol | 0.5 |
| isopropyl myristate | 0.1 |
| TG 227 | ad 100 |
| Tiotropium bromide | 0.029 |
| AWD-12-281 | 0.033 |
| absolute ethanol | 0.5 |
| isopropyl myristate | 0.1 |
| TG 227 | ad 100 |
| Tiotropium bromide | 0.029 |
| Compound of formula 2ca | 0.033 |
| absolute ethanol | 0.5 |
| isopropyl myristate | 0.1 |
| TG 227 | ad 100 |
| Tiotropium bromide | 0.015 |
| NK$_1$-receptor antagonist | 0.066 |
| Soya lecithin | 0.2 |
| TG 11:TG12 = 2:3 | ad 100 |
| Tiotropium bromide | 0.029 |
| NK$_1$-receptor antagonist | 0.033 |
| absolute ethanol | 0.5 |
| isopropyl myristate | 0.1 |
| TG 227 | ad 100 |
| Tiotropium bromide | 0.029 |
| NK$_1$-receptor antagonist | 0.033 |
| absolute ethanol | 0.5 |
| isopropyl myristate | 0.1 |
| TG 227 | ad 100 |
| Tiotropium bromide | 0.029 |
| NK$_1$-receptor antagonist | 0.033 |
| absolute ethanol | 0.5 |
| isopropyl myristate | 0.1 |
| TG 227 | ad 100 |
| Tiotropium bromide | 0.015 |
| Endothelin antagonist 2e | 1.2 |
| Soya lecithin | 0.3 |
| TG 134a:TG227 = 2:3 | ad 100 |
| Ipratropium bromide | 0.015 |
| Endothelin antagonist 2e | 1.2 |
| soya lecithin | 0.3 |
| TG 134a:TG227 = 2:3 | ad 100 |
| Tiotropium bromide | 0.029 |
| Endothelin antagonist 2 | 1.4 |
| Absolute ethanol | 0.5 |
| Isopropyl myristate | 0.1 |
| TG 227 | ad 100 |
| Ipratropium bromide | 0.029 |
| Endothelin antagonist 2 | 1.4 |
| Absolute ethanol | 0.5 |
| Isopropyl myristate | 0.1 |
| TG 227 | ad 100 |
| Tiotropium bromide | 0.015 |
| Epinastine hydrochloride | 0.066 |
| Soya lecithin | 0.2 |
| TG 134a:TG227 (2:3) | to 100 |
| Tiotropium bromide | 0.029 |
| Epinastine hydrochloride | 0.33 |
| absolute ethanol | 0.5 |
| Isopropyl myristate | 0.1 |
| TG 227 | to 100 |

C. Forms for Nasal Administration

1. Solution 900 ml of purified water are placed in a suitable vessel and 285.7 mg of tiotropium monohydrate, 2000 mg of epinastine hydrochloride and 500 mg of disodium EDTA are dissolved therein with stirring. Then the pH of the solution is adjusted to 3 with 0.1 N hydrochloric acid and the solution is made up to a total volume of 1000 ml with purified water. The solution is transferred into a suitable pump for nasal use. With a spray volume of 70 µl per spray actuation, 20 µg of tiotropium bromide and 140 µg of epinastine hydrochloride are administered each time.

2. Powder 20 g of tiotropium bromide monohydrate and 140 g of epinastine hydrochloride with a particle size distribution for the two active substances containing about 90% of the active substance particles in the size range from 5 µm to 20 µm are placed in a suitable mixer. 5.34 µg of lactose (200 M) are added to the two active substances and they are mixed together until a homogeneous mixture is obtained. Then 5.5 mg of this mixture are transferred into a nasal spray system. When administered nasally, 20 µg of tiotropium bromide and 140 µg of epinastine hydrochloride are delivered per spray.

We claim:

1. A pharmaceutical composition comprising: (a) an anticholinergic which is a tiotropium salt; and (b) an antihistamine which is epinastine; optionally together with a pharmaceutically acceptable excipient, the anticholinergic and the antihistamine optionally in the form of their enantiomers, mixtures of their enantiomers, their racemates, or their hydrates.

2. The pharmaceutical composition according to claim 1, wherein the anticholinergic is a tiotropium salt with a counter-ion selected from chloride, bromide, iodide, p-toluene sulfonate, or methylsulfate.

3. The pharmaceutical composition of claim 2, wherein the counter-ion is bromide.

4. The pharmaceutical composition according to claim 1, wherein the weight ratio of the anticholinergic to the antihistamine is in the range of from 1:300 to 50:1.

5. The pharmaceutical composition according to claim 1, wherein the weight ratio of the tiotropium salt to the antihistamine is in the range of from 1:250 to 40:1.

6. The pharmaceutical composition according to claim 1, wherein the pharmaceutical composition is in a form suitable for inhalation.

7. The pharmaceutical composition according to claim 1, wherein the pharmaceutical composition is an inhalable powder, a propellant-containing metering aerosol, or a propellant-free inhalable solution or suspension.

8. A pharmaceutical composition according to claim 1, wherein the pharmaceutical composition is a propellant-containing inhalable aerosol and the anticholinergic and the antihistamine are in dissolved or dispersed form.

9. The pharmaceutical composition according to claim 8, wherein the propellant-containing inhalable aerosol comprises a propellant gas selected from hydrocarbons and halohydrocarbons.

10. The pharmaceutical composition according to claim 8, wherein the propellant-containing inhalable aerosol comprises a propellant gas selected from the group consisting of: n-propane; n-butane; isobutane; and chlorinated and/or fluorinated derivatives of methane, ethane, propane, butane, cyclopropane, and cyclobutane.

11. The pharmaceutical composition according to claim 10, wherein the propellant gas is TG134a, TG227, or a mixture thereof.

12. The pharmaceutical composition according to claim 8, further comprising at least one of a cosolvent, stabilizer, surfactant, antioxidant, lubricant, or means for adjusting the pH of the composition.

13. The pharmaceutical composition according to claim 8, wherein the amount of the anticholinergic or the antihistamine is up to 5 wt. % of the pharmaceutical composition.

14. A pharmaceutical composition according to claim 1, wherein the pharmaceutical composition is propellant-free inhalable solution or suspension that further comprises a solvent selected from water, ethanol, or a mixture of water and ethanol.

15. The pharmaceutical composition according to claim 14, wherein the pH is between 2 and 7.

16. The pharmaceutical composition according to claim 15, wherein the pH of the pharmaceutical composition is adjusted by means of one or more acids selected from the group consisting of: hydrochloric acid, hydrobromic acid, nitric acid, sulfuric acid, ascorbic acid, citric acid, malic acid, tartaric acid, maleic acid, succinic acid, fumaric acid, acetic acid, formic acid, and propionic acid.

17. The pharmaceutical composition according to claim 15, further comprising other co-solvents or excipients.

18. A method of treating inflammatory or obstructive diseases of the respiratory tract in a patient in need of such treatment, the method comprising administering to the patient a therapeutically effective amount of the pharmaceutical composition according to one of claims 1, 2, 3 or 4 to 6.

19. A pharmaceutical composition consisting essentially of: (a) an anticholinergic which is a tiotropium salt; and (b) an antihistamine which is epinastine; wherein the pharmaceutical composition is in the form of an inhalable powder.

20. The pharmaceutical composition according to claim 19, wherein the pharmaceutical composition further comprises a suitable physiologically acceptable excipient selected from the group consisting of: monosaccharides, disaccharides, oligo- and polysaccharides, polyalcohols, and salts.

21. The pharmaceutical composition of claim 20, wherein the excipient has a maximum average particle size of up to 250 µm.

22. The pharmaceutical composition of claim 21, wherein the excipient has a maximum average particle size of between 10 µm and 150 µm.

23. A pharmaceutical composition consisting essentially of: (a) an anticholinergic which is a tiotropium salt; (b) an antihistamine which is epinastine; (c) a solvent; (d) benzalkonium chloride; and (e) sodium edetate.

24. A pharmaceutical composition consisting essentially of: (a) an anticholinergic which is a tiotropium salt; (b) an antihistamine which is epinastine; (c) a solvent; and (d) benzalkonium chloride.

25. A kit comprising one or more unit dosage containers containing a pharmaceutical composition, each unit dosage container containing a pharmaceutical composition comprising: (a) an anticholinergic which is a tiotropium salt; and (b) an antihistamine which is epinastine, each optionally together with a pharmaceutically acceptable excipient, the anticholinergic and the antihistamine optionally in the form of their enantiomers, mixtures of their enantiomers, their racemates, or their hydrates.

26. The kit according to claim 25, further comprising instructions with directions for using the kit.

27. A kit comprising: (a) a first container containing a first pharmaceutical formulation comprising an anticholinergic which is a tiotropium salt; and (b) a second container containing a second pharmaceutical formulation comprising an antihistamine which is epinastine, each container each optionally further containing a pharmaceutically acceptable excipient, the anticholinergic and the antihistamine optionally in the form of their enantiomers, mixtures of their enantiomers, their racemates, or their hydrates.

28. The kit according to claim 27, further comprising instructions with directions for using the kit.

* * * * *